(12) United States Patent
King et al.

(10) Patent No.: US 7,074,810 B2
(45) Date of Patent: Jul. 11, 2006

(54) TRIAZOLONE AND TRIAZOLETHIONE DERIVATIVES AS INHIBITORS OF MATRIX METALLOPROTEINASES AND/OR TNF-α CONVERTING ENZYME

(75) Inventors: Bryan W. King, Blue Bell, PA (US); James Sheppeck, Newtown, PA (US); John L. Gilmore, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 285 days.

(21) Appl. No.: 10/678,331

(22) Filed: Oct. 3, 2003

(65) Prior Publication Data

US 2004/0116491 A1     Jun. 17, 2004

Related U.S. Application Data

(60) Provisional application No. 60/416,709, filed on Oct. 7, 2002.

(51) Int. Cl.
*A61K 31/44*    (2006.01)
*C07D 401/00*    (2006.01)

(52) U.S. Cl. .................................. 514/340; 546/272.4

(58) Field of Classification Search ............... 514/340; 546/272.4
See application file for complete search history.

(56) References Cited

U.S. PATENT DOCUMENTS

| 5,220,018 A | 6/1993 | Bock et al. |
| 5,438,063 A | 8/1995 | Osswald et al. |
| 5,641,796 A | 6/1997 | Dominianni et al. |
| 5,721,263 A | 2/1998 | Inada et al. |
| 5,750,549 A | 5/1998 | Caldwell et al. |
| 6,177,587 B1 | 1/2001 | Hashimoto et al. |
| 6,605,722 B1 | 8/2003 | Makovec et al. |

FOREIGN PATENT DOCUMENTS

| EP | 0 520 423 | 5/2003 |
| WO | WO 97/14671 | 4/1997 |
| WO | WO 01/87866 | 11/2001 |
| WO | WO 02/30930 | 4/2002 |

*Primary Examiner*—Deborah C. Lambkin
(74) *Attorney, Agent, or Firm*—Jing G. Sun

(57) ABSTRACT

The present application describes novel hydantoin derivatives of formula (I):

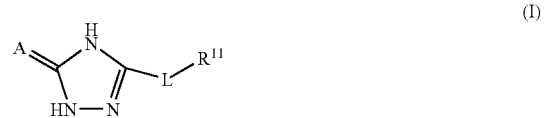

(I)

or pharmaceutically acceptable salt or prodrug forms thereof, wherein A, L, and $R^{11}$ are defined in the present specification, which are useful as inhibitors of matrix metalloproteinases (MMP), TNF-α converting enzyme (TACE), aggrecanase, or a combination thereof.

23 Claims, No Drawings

TRIAZOLONE AND TRIAZOLETHIONE DERIVATIVES AS INHIBITORS OF MATRIX METALLOPROTEINASES AND/OR TNF-α CONVERTING ENZYME

CROSS-REFERENCE TO RELATED APPLICATIONS

The present application claims the priority benefit of U.S. Provisional Application No. 60/416,709, filed Oct. 7, 2002, which is expressly incorporated fully herein by reference.

FIELD OF THE INVENTION

This invention relates generally to novel triazolone and triazolethione derivatives as inhibitors of matrix metalloproteinases (MMP), TNF-α converting enzyme (TACE), aggrecanase or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthritis Rheum.* 1978, 21, 761–766, Woessner et al. *Arthritis Rheum.* 1983, 26, 63–68 and Woessner et al. *Arthritis Rheum.* 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al. *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

Human macrophage elastase (MMP-12) is expressed primarily by alveolar macrophages and is responsible for tissue remodelling by proteolytically degrading elastin. MMP-12 knockout mice appear to have a diminished capacity to degrade elastin, particularly in lung tissue, and appear less susceptible to pulmonary diseases such as emphysema (Hautamaki et al. *Science* 1997, 277, 2002–2004; Lanone et al. *J. Clin. Invest.* 2002, 110, 463–474). This invention describes molecules that inhibit the activity of MMP-12 and may circumvent undesired tissue destruction found in a variety of human diseases. These novel molecules provide a means of mechanism based therapeutic intervention for diseases including but not restricted to: emphysema, asthma, chronic obstructive pulmonary disease, cystic fibrosis, cancer, metastatic disease, atherosclerosis, and aneurysm.

U.S. Pat. No. 5,220,018 depicts cholecystokinin antagonists of the following formula:

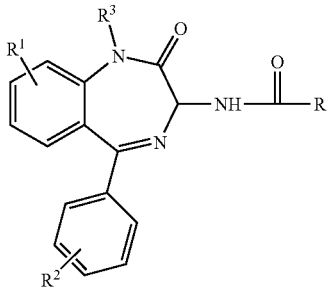

wherein R can be —NH-1,3-phenylene-triazolone; and $R^1$, $R^2$ and $R^3$ are a variety of groups.

U.S. Pat. No. 5,750,549 and WO97/14671 disclose tachykinin receptor antagonists of the following formula:

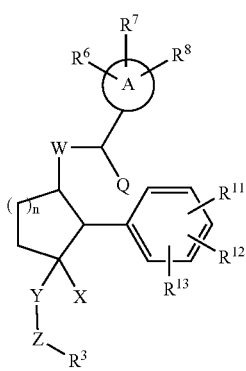

wherein A is phenyl or heteroaryl; Q and X are H or $C_{1-6}$ alkyl; W, Y and Z are linkers; $R^3$ can be triazolone or $C_{1-6}$ alkyl-triazolone; n is 1–3; and $R^6$, $R^7$, $R^8$, $R^{11}$, $R^{12}$, and $R^{13}$ are a variety of groups.

U.S. Pat. No. 5,438,063 discloses angiotensin II antagonists of the following formula:

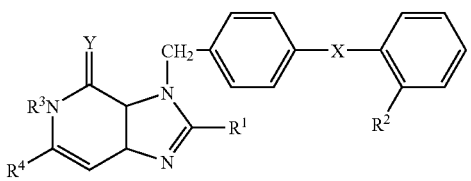

wherein $R^2$ can be triazolone; X is absent, —NHCO—, or —CONH—; Y is O or S; and $R^1$, $R^3$ and $R^4$ are a variety of groups.

U.S. Pat. No. 5,641,796 illustrates oral hypoglycemic agents of the following formula:

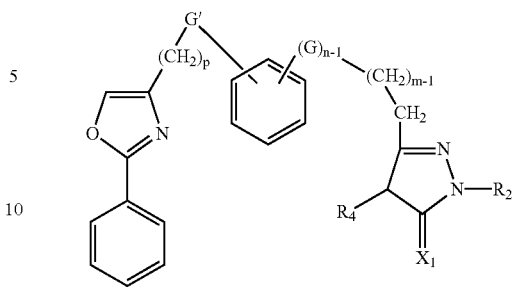

wherein $X_1$ is O or S; G and G' are O or S; $R_2$ and $R_4$ are a variety of groups; m is 1 or 2; n is 1 or 2; and p is an integer from 1 to 6.

U.S. Pat. No. 5,721,263 discloses a pharmaceutical composition containing compounds of the following formula:

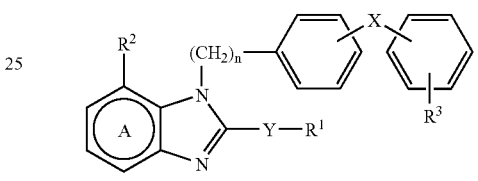

wherein A is a benzene ring; $R^3$ can be triazolone or triazolethione; X and Y are linkers; and $R^1$ and $R^2$ are a variety of groups.

U.S. Pat. No. 6,177,587 describes compounds of the following formula:

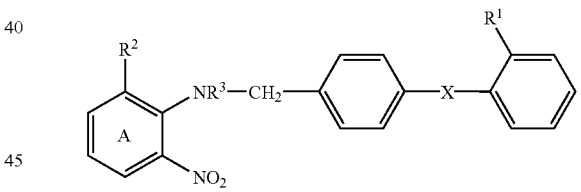

wherein A is a benzene ring; $R^1$ can be triazolone or triazolethione; X is a linker; and $R^2$ and $R^3$ are a variety of groups.

WO01/87866 describes neurokinin-1 receptor antagonists of the following formula:

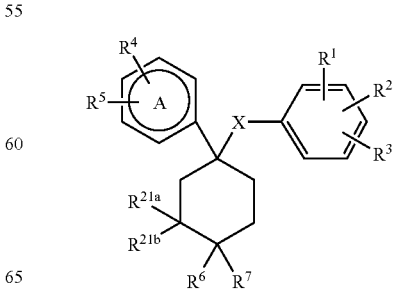

wherein A is a phenyl or pyridyl ring; X is a linker; $R^1$, $R^2$, $R^3$, $R^4$, $R^5$, $R^6$, $R^{21a}$, and $R^{21b}$ are a variety of groups; and $R^7$ can be a triazolone-terminated group.

WO02/30930 discloses HIV integrase inhibitors of the following formula:

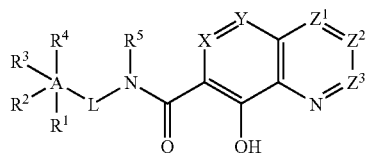

wherein A is phenyl or phenyl fused carbocycle; L is a bond or a linker; X is N or C—$Q^1$; Y is N or C—$Q^2$; $Z^1$ is N or C—$Q^3$; $Z^2$ is N or C—$Q^4$; $Z^3$ is N or CH; $Q^1$, $Q^2$ $Q^3$, and $Q^4$ can be a triazolone-terminated group; and $R^1$, $R^2$, $R^3$, $R^4$ and $R^5$ are a variety of groups.

EP 520423 illustrates angiotensin II antagonists of the following formula:

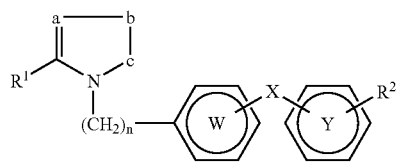

wherein $R^1$ is an optionally substituted hydrocarbon residue; $R^2$ can be triazolone or triazolethione; a and b forming the heterocyclic residue are independently one or two optionally substituted carbon or hetero atoms; and c is an optionally substituted carbon or hetero atom.

Compounds specifically described in the above mentioned patents or patent applications are not considered to be part of the present invention.

It is desirable to find new compounds with improved pharmacological characteristics compared with known MMP and/or TACE inhibitors. For example, it is preferred to find new compounds with improved MMP and/or TACE inhibitory activity and selectivity for an MMP and/or TACE versus other metalloproteases (e.g., specificity for one MMP versus another). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

The compounds of the present invention act as inhibitors of MPs, in particular TACE, MMPs, and/or aggrecanase. These novel molecules are provided as anti-inflammatory compounds and cartilage protecting therapeutics. The inhibition of aggrecanase, TACE, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, the present invention provides novel triazolone and triazolethione derivatives useful as MMP and/or TACE inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory disorders, comprising: administering to a host, in need of such treatment, a therapeutically effective amount of at least one of the compounds of the present invention or a pharmaceutically acceptable salt or prodrug form thereof.

The present invention provides a method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt or prodrug form thereof.

The present invention provides a method comprising: administering a compound of the present invention or a pharmaceutically acceptable salt or prodrug form thereof in an amount effective to treat a condition or disease mediated by MMPs, TACE, aggrecanase, or a combination thereof.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides novel compounds of the present invention for use in therapy.

The present invention provides the use of novel compounds of the present invention for the manufacture of a medicament for the treatment of a condition or disease mediated by MMPs, TACE, aggrecanase, or a combination thereof.

These and other features, which will become apparent during the following detailed description, have been achieved by the inventors' discovery that compounds of formula (I):

or pharmaceutically acceptable salt or prodrug forms thereof, wherein A, L, and $R^{11}$ are defined below, are effective as MMP and/or TACE inhibitors.

DETAILED DESCRIPTION OF PREFERRED EMBODIMENTS

In a first aspect, the present invention provides, inter alia, compounds of formula (I):

(I)

[Chemical structure diagram showing a five-membered ring with A, NH, HN, N atoms and L—R¹¹ substituent]

or a stereoisomer or pharmaceutically acceptable salt form thereof, wherein;

A is O or S;

L is —(CR²R³)—(CR⁴R⁵)$_n$—(CR⁶R⁷)$_{n1}$—;

alternatively, L is selected from the group:

[Chemical structures showing ring E and ring F with R¹ and R¹ᵃ substituents]

R¹ is, independently at each occurrence, H, C$_{1-6}$ alkyl, C$_{2-6}$ alkenyl, or C$_{2-6}$ alkynyl;

R¹ᵃ is, independently at each occurrence, H, C$_{1-6}$ alkyl, C$_{2-6}$ alkenyl, or C$_{2-6}$ alkynyl;

R² is Q¹, C$_{1-6}$ alkylene-Q¹, C$_{2-6}$ alkenylene-Q¹, C$_{2-6}$ alkynylene-Q¹, —(CRᵃRᵃ¹)$_r$O(CRᵃRᵃ¹)$_s$—Q¹, —(CRᵃRᵃ¹)$_r$NRᵃ(CRᵃRᵃ¹)$_s$—Q¹, —(CRᵃRᵃ¹)$_r$C(O)(CRᵃRᵃ¹)$_s$—Q¹, —(CRᵃRᵃ¹)$_r$C(O)O(CRᵃRᵃ¹)$_s$—Q¹, —(CRᵃRᵃ¹)$_r$OC(O)(CRᵃRᵃ¹)$_s$—Q¹, —(CRᵃRᵃ¹)$_r$C(O)NRᵃRᵃ¹, —(CRᵃRᵃ¹)$_r$C(O)NRᵃ(CRᵃRᵃ¹)$_s$—Q¹, —(CRᵃRᵃ¹)$_r$NRᵃC(O)(CRᵃRᵃ¹)$_s$—Q¹, —(CRᵃRᵃ¹)$_r$OC(O)O(CRᵃRᵃ¹)$_s$—Q¹, —(CRᵃRᵃ¹)$_r$OC(O)NRᵃ(CRᵃRᵃ¹)$_s$—Q¹, —(CRᵃRᵃ¹)$_r$NRᵃC(O)NRᵃ(CRᵃRᵃ¹)$_s$—Q¹, —(CRᵃRᵃ¹)$_r$S(O)$_p$(CRᵃRᵃ¹)$_s$—Q¹, —(CRᵃRᵃ¹)$_r$SO$_2$NRᵃ(CRᵃRᵃ¹)$_s$—Q¹, —(CRᵃRᵃ¹)$_r$NRᵃSO$_2$(CRᵃRᵃ¹)$_s$—Q¹, or (CRᵃRᵃ¹)$_r$NRᵃSO$_2$NRᵃ(CRᵃRᵃ¹)$_s$—Q¹;

R³ is Q, C$_{1-6}$ alkylene-Q, C$_{2-6}$ alkenylene-Q, C$_{2-6}$ alkynylene-Q, —(CRᵃRᵃ¹)$_r$O(CRᵃRᵃ¹)$_s$—Q, —(CRᵃRᵃ¹)$_r$NRᵃ(CRᵃRᵃ¹)$_s$—Q, —(CRᵃRᵃ¹)$_r$C(O)(CRᵃRᵃ¹)$_s$—Q, —(CRᵃRᵃ¹)$_r$C(O)O(CRᵃRᵃ¹)$_s$—Q, —(CRᵃRᵃ¹)$_r$C(O)NRᵃRᵃ¹, —(CRᵃRᵃ¹)$_r$C(O)NRᵃ(CRᵃRᵃ¹)$_s$—Q, —(CRᵃRᵃ¹)$_r$NRᵃC(O)(CRᵃRᵃ¹)$_s$—Q, —(CRᵃRᵃ¹)$_r$S(O)$_p$(CRᵃRᵃ¹)$_s$—Q, —(CRᵃRᵃ¹)$_r$SO$_2$NRᵃ(CRᵃRᵃ¹)$_s$—Q, or —(CRᵃRᵃ¹)$_r$NRᵃSO$_2$(CRᵃRᵃ¹)$_s$—Q;

Q is, independently at each occurrence, H, CHF$_2$, CH$_2$F, CF$_3$, a C$_{3-13}$ carbocycle substituted with 0–5 R$^d$, or a 5–14 membered heterocycle consisting of carbon atoms and 1–4 heteroatoms selected from the group consisting of N, O, and S(O)$_p$, and substituted with 0–5 R$^d$;

Q¹ is, independently at each occurrence, H, a C$_{3-13}$ carbocycle substituted with 0–5 R$^d$, or a 5–14 membered heterocycle consisting of carbon atoms and 1–4 heteroatoms selected from the group consisting of N, NR¹⁰, O, and S(O)$_p$, and substituted with 0–5 R$^d$;

R⁴ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

R⁵ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

R⁶ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

R⁷ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

n is 0 or 1;

n1 is 0 or 1;

alternatively, R² and R³, together with the carbon atom to which they are attached, combine to form a 3–8 membered carbocyclic or heterocyclic ring consisting of carbon atoms and 0–2 ring heteroatoms selected from O, N, NR¹⁰, and S(O)$_p$, and 0–2 double bonds, and substituted with 0–3 R⁹; and the carbocyclic or heterocyclic ring is optionally fused to a 5–6 membered carbocycle or heterocycle consisting of carbon atoms and 0–2 ring heteroatoms selected from O, N, NR¹⁰, and S(O)$_p$, and 0–2 double bonds, and substituted with 0–3 R⁹;

alternatively, when n is 1, R⁴ and R⁵, together with the carbon atom to which they are attached, combine to form a 3–8 membered carbocyclic or heterocyclic ring consisting of carbon atoms and 0–2 ring heteroatoms selected from O, N, NR¹⁰, and S(O)$_p$, and 0–2 double bonds, and substituted with 0–3 R⁹; and the carbocyclic or heterocyclic ring is optionally fused to a 5–6 membered carbocycle or heterocycle consisting of carbon atoms and 0–2 ring heteroatoms selected from O, N, NR¹⁰, and S(O)$_p$, and 0–2 double bonds, and substituted with 0–3 R⁹;

alternatively, when n1 is 1, R⁶ and R⁷, together with the carbon atom to which they are attached, combine to form a 3–8 membered carbocyclic or heterocyclic ring consisting of carbon atoms and 0–2 ring heteroatoms selected from O, N, NR¹⁰, and S(O)$_p$, and 0–2 double bonds, and substituted with 0–3 R⁹; and the carbocyclic or heterocyclic ring is optionally fused to a 5–6 membered carbocycle or heterocycle consisting of carbon atoms and 0–2 ring heteroatoms selected from O, N, NR¹⁰, and S(O)$_p$, and 0–2 double bonds, and substituted with 0–3 R⁹;

ring E is a 3–8 membered carbocyclic or heterocyclic ring consisting of carbon atoms and 0–2 ring heteroatoms selected from O, N, NR¹⁰, and S(O)$_p$, and 0–2 double bonds, and substituted with 0–3 R$^c$; and the carbocyclic or heterocyclic ring is optionally fused to a 5–6 membered carbocycle or heterocycle consisting of carbon atoms and 0–2 ring heteroatoms selected from O, N, NR¹⁰, and S(O)$_p$, and 0–2 double bonds, and substituted with 0–3 R⁹;

ring F is a 4–8 membered carbocyclic or heterocyclic ring consisting of carbon atoms and 0–2 ring heteroatoms selected from O, N, NR¹⁰, and S(O)$_p$, and 0–2 double bonds, and substituted with 0–3 R$^c$; and the carbocyclic or heterocyclic ring is optionally fused to a 5–6 membered carbocycle or heterocycle consisting of carbon atoms and 0–2 ring heteroatoms selected from O, N, NR¹⁰, and S(O)$_p$, and 0–2 double bonds, and substituted with 0–3 R⁹;

R¹¹ is —W—U—X—Y—Z—Uᵃ—Xᵃ—Yᵃ—Zᵃ;

W is (CRᵃRᵃ¹)$_m$, C$_{2-3}$ alkenylene, or C$_{2-3}$ alkynylene;

U is O, C(O), CRᵃ(OH), C(O)O, OC(O), C(O)NRᵃ¹, NRᵃ¹C(O), OC(O)O, OC(O)NRᵃ¹, NRᵃ¹C(O)O, NRᵃ¹C(O)NRᵃ¹, S(O)$_p$, S(O)$_p$NRᵃ¹, NRᵃ¹S(O)$_p$, or NRᵃ¹SO$_2$NRᵃ¹;

X is absent or is C$_{1-3}$ alkylene, C$_{2-3}$ alkenylene, or C$_{2-3}$ alkynylene; Y is absent or is O, NRᵃ¹, S(O)$_p$, or C(O);

Z is a C$_{3-13}$ carbocycle substituted with 0–5 R$^b$, or a 5–14 membered heterocycle consisting of carbon atoms and 1–4 heteroatoms selected from the group consisting of N, O, and S(O)$_p$ and substituted with 0–5 R$^b$;

$U^a$ is absent or is O, $NR^{a1}$, C(O), $CR^a(OH)$, C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, or $NR^{a1}SO_2NR^{a1}$;

$X^a$ is absent or is $C_{1-10}$ alkylene, $C_{2-10}$ alkenylene, or $C_{2-10}$ alkynylene;

$Y^a$ is absent or is O, $NR^{a1}$, $S(O)_p$, or C(O);

$Z^a$ is H, a $C_{3-13}$ carbocycle substituted with 0–5 $R^c$, or a 5–14 membered heterocycle consisting of carbon atoms and 1–4 heteroatoms selected from the group consisting of N, O, and $S(O)_p$ and substituted with 0–5 $R^c$;

provided that U, Y, Z, $U^a$, $Y^a$, and $Z^a$ do not combine to form a N—N, N—O, O—N, —O—O, $S(O)_p$—O, O—$S(O)_p$ or $S(O)_p$—$S(O)_p$ group;

$R^a$ is, independently at each occurrence, H, $C_{1-6}$ alkyl, phenyl, or benzyl;

$R^{a1}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3-8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

$R^{a2}$ is, independently at each occurrence, $C_{1-4}$ alkyl, phenyl, or benzyl;

$R^{a3}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3-8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^b$, at each occurrence, is independently selected from $C_{1-6}$ alkyl substituted with 0–1 $R^{c1}$, $OR^a$, $SR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —OC(O)$NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, —$CF_3$, —$CF_2CF_3$, —$CHF_2$, —$CH_2F$, or phenyl;

$R^c$ is, independently at each occurrence, H, $OR^a$, Cl, F, Br, I, =O, CN, $NO_2$, $CF_3$, —$CF_2CF_3$, $CH_2F$, $CHF_2$, —$(CR^aR^{a1})_rNR^aR^{a1}$, —$(CR^aR^{a1})_rC(=NCN)NR^aR^{a1}$, —$(CR^aR^{a1})_rC(=NR^a)NR^aR^{a1}$, —$(CR^aR^{a1})_rC(=NOR^a)NR^aR^{a1}$, —$(CR^aR^{a1})_rC(O)NR^aOH$, —$(CR^aR^{a1})_rC(O)R^{a1}$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or —$(CR^aR^{a1})_r$-5-14 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^{c1}$ is, independently at each occurrence, H, $C_{1-4}$ alkyl, $OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, $OR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, OC(O)$NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, —$CF_3$, —$CF_2CF_3$, $C_{3-10}$ carbocycle, or a 5–14 membered heterocycle consisting of carbon atoms and 1–4 heteroatoms selected from the group consisting of N, O, and $S(O)_p$;

$R^e$ is, independently at each occurrence, H, $C_{1-6}$ alkyl, $C_{1-6}$ alkoxy, phenoxy, benzoxy, $C_{3-10}$ carbocycle substituted with 0–2 $R^{c1}$, or a 5–10 membered heterocycle consisting of carbon atoms and 1–4 heteroatoms selected from the group consisting of N, O, and $S(O)_p$, and substituted with 0–2 $R_{c1}$;

$R^9$ is, independently at each occurrence, H, —$(CR^aR^{a1})_r$$NR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, $(CR^aR^{a1})_rNR^aC(O)R^{a1}$, —$(CR^aR^{a1})_rC(S)NR^aR^{a1}$, $(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, $(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $(CR^aR^{a1})_rNR^aSO_2NR^aR^{a1}$, $C_{1-6}$ alkyl substituted with 0–2 $R_{c1}$, $C_{2-6}$ alkenyl substituted with 0–2 $R^{c1}$, $C_{2-6}$ alkynyl substituted with 0–2 $R_{c1}$, —$(CR^aR^{a1})_r$—$C_{3-10}$ carbocycle substituted with 0–2 $R^{c1}$, or —$(CR^aR^{a1})_r$-5-10 membered heterocycle consisting of carbon atoms and 1–4 heteroatoms selected from the group consisting of N, O, and $S(O)_p$, and substituted with 0–2 $R^{c1}$;

$R^{10}$ is, independently at each occurrence, H, —$(CR^aR^{a1})_t$$NR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, (—$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, $(CR^aR^{a1})_tOC(O)NR^aR^{a1}$, —$(CR^aR^{a1})_rNR^aC(O)OR^{a1}$, —$(CR^aR^{a1})_rNR^aC(O)NR^aR^{a1}$, $(CR^aR^{a1})_rS(O)_pR^{a3}$, —$(CR^aR^{a1})_rSO_2NR^aR^{a1}$, —$(CR^aR^{a1})_t$$NR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or —$(CR^aR^{a1})_r$-5-10 membered heterocycle consisting of carbon atoms and 1–4 heteroatoms selected from the group consisting of N, O, and $S(O)_p$, and substituted with 0–2 $R^{c1}$;

m, at each occurrence, is selected from 0, 1, 2 and 3;

p, at each occurrence, is selected from 0, 1, and 2;

r, at each occurrence, is selected from 0, 1, 2, 3, and 4;

s, at each occurrence, is selected from 0, 1, 2, 3, and 4; and t, at each occurrence, is selected from 1, 2, 3, and 4;

provided that:

(i) when L is $CR^2R^3$ or $CR^2R^3CH^2$, $Z^a$ is other than H;

(ii) when Z is cyclohexyl, benzodiazepinyl or a nitrogen-containing 10-membered bicyclic heteroaryl, then $Z^a$ is other than phenyl or phenyl fused carbocycle;

(iii) when Z is phenyl, and $Z^a$ is oxazolyl, then $R^c$ is other than phenyl;

(iv) when Z is a $C_{5-7}$ cycloalkyl, then $R^b$ is other than phenyl;

(v) when A is S, and L is 1,2-phenylene, then $Z^a$ is other than thienyl or phenyl substituted with triazolthione;

(vi) when A is S, L is CH$_2$, U—X—Y forms O or S, and Z is a benzopyranyl, quinazolinyl, or triazinyl ring, then Z$^a$ is other than phenyl;

(vii) when A is S, L is 4,5,6-7-tetrahydrobenzothienyl, and U—X—Y forms C(O)NH, Z is other than 5,6,7,8-tetrahydro-benzothieno[2,3-b]pyridinyl; and (viii) when L is 1,2-phenylene or 1,3-phenylene, then U$^a$—X$^a$—Y$^a$ forms other than C$_{1-2}$ alkylene or CH$_2$NR$^{a1}$.

In a second aspect, the present invention includes compounds of Formula (I) or a stereoisomer or pharmaceutically acceptable salt form thereof, wherein:

R$^2$ is Q$^1$, C$_{1-6}$ alkylene-Q$^1$, C$_{2-6}$ alkenylene-Q$^1$, C$_{2-6}$ alkynylene-Q$^1$, —(CR$^a$R$^{a1}$)$_r$O(CR$^a$R$^{a1}$)$_s$—Q$^1$, (CR$^a$R$^{a1}$)$_r$NR$^a$(CR$^a$R$^{a1}$)$_s$—Q$^1$, —(CR$^a$R$^{a1}$)$_r$C(O)(CR$^a$R$^{a1}$)$_s$—Q$^1$, —(CR$^a$R$^{a1}$)$_r$C(O)O(CR$^a$R$^{a1}$)$_s$—Q$^1$, —(CR$^a$R$^{a1}$)$_r$OC(O)(CR$^a$R$^{a1}$)$_s$—Q$^1$, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$—Q$^1$, —(CR$^a$R$^{a1}$)$_r$NR$^a$C(O)(CR$^a$R$^{a1}$)$_s$—Q$^1$, —(CR$^a$R$^{a1}$)$_r$S(O)$_p$(CR$^a$R$^{a1}$)$_s$—Q$^1$, —(CR$^a$R$^{a1}$)$_r$SO$_2$NR$^a$(CR$^a$R$^{a1}$)$_s$—Q$^1$, or —(CR$^a$R$^{a1}$)$_r$NR$^a$SO$_2$(CR$^a$R$^{a1}$)$_s$—Q$^1$;

R$^3$ is Q, C$_{1-6}$ alkylene-Q, C$_{2-6}$ alkenylene-Q, C$_{2-6}$ alkynylene-Q, —(CH$_2$)$_r$O(CH$_2$)$_s$—Q, —(CH$_2$)$_r$NR$^a$(CH$_2$)$_s$—Q, —(CH$_2$)$_r$C(O)(CH$_2$)$_s$—Q, —(CH$_2$)$_r$C(O)O(CH$_2$)$_s$—Q, —(CH$_2$)$_r$C(O)NR$^a$R$^{a1}$, —(CH$_2$)$_r$C(O)NR$^a$(CH$_2$)$_s$—Q, —(CH$_2$)$_r$NR$^a$C(O)(CH$_2$)$_s$—Q, —(CH$_2$)$_r$S(O)$_p$(CH$_2$)$_s$—Q, —(CH$_2$)$_r$SO$_2$NR$^a$(CH$_2$)$_s$—Q, or —(CH$_2$)$_r$NR$^a$SO$_2$(CH$_2$)$_s$—Q;

R$^4$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

R$^5$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

R$^6$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

R$^7$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;

alternatively, R$^2$ and R$^3$, together with the carbon atom to which they are attached, combine to form a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–2 R$^9$;

alternatively, when n is 1, R$^4$ and R$^5$ together with the carbon atom to which they are attached combine to form a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–2 R$^9$;

alternatively, when n1 is 1, R$^6$ and R$^7$ together with the carbon atom to which they are attached combine to form a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–2 R$^9$;

ring E is a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–3 R$^c$;

ring F is a 4–8 membered carbocyclic or heterocyclic ring consisting of carbon atoms and 0–2 ring heteroatoms selected from O, N, NR$^{10}$, and S(O)$_p$, and 0–2 double bonds, and substituted with 0–3 R$_c$;

W is (CR$^a$R$^{a1}$)$_m$;

U is O, C(O), CR$^a$(OH), C(O)O, OC(O), C(O)NR$^{a1}$, NR$^{a1}$C(O), S(O)$_p$, S(O)$_p$NR$^{a1}$, or NR$^{a1}$S(O)$_p$;

X is absent or is C$_{1-3}$ alkylene;

Z is a C$_{3-8}$ cycloalkyl substituted with 0–5 R$^b$, a C$_{3-8}$ cycloalkenyl substituted with 0–5 R$^b$, phenyl substituted with 0–5 R$^b$, naphthyl substituted with 0–5 R$^b$, or a 5–14 membered heterocycle consisting of carbon atoms and 1–4 heteroatoms selected from the group consisting of N, O, and S(O)$_p$ and substituted with 0–5 R$^b$;

U$^a$ is absent or is O, NR$^{a1}$, C(O), CR$^a$(OH), C(O)O, C(O)NR$^{a1}$, NR$^{a1}$C(O), S(O)$_p$, S(O)$_p$NR$^{a1}$, or NR$^{a1}$S(O)$_p$;

X$^a$ is absent or is C$_{1-4}$ alkylene, C$_{2-4}$ alkenylene, or C$_{2-4}$ alkynylene;

Y$^a$ is absent or is O or NR$^{a1}$;

Z$^a$ is a C$_{6-13}$ carbocycle substituted with 0–5 R$^c$, or a 5–14 membered heterocycle consisting of carbon atoms and 1–4 heteroatoms selected from the group consisting of N, O, and S(O)$_p$, and substituted with 0–5 R$^c$;

R$^a$ is, independently at each occurrence, H, C$_{1-6}$ alkyl, phenyl, or benzyl;

R$^{a1}$ is, independently at each occurrence, H, C$_{1-6}$ alkyl, C$_{2-6}$ alkenyl, C$_{2-6}$ alkynyl, and —(CH$_2$)$_r$-3–8 membered carbocyclic or heterocyclic ring consisting of carbon atoms and 0–2 ring heteroatoms selected from N, NR$^{a2}$, O, and S(O)$_p$;

alternatively, R$^a$and R$^{a1}$ when attached to a nitrogen, together with the nitrogen to which they are attached, combine to form a 5 or 6 membered heterocycle consisting of carbon atoms and from 0–1 additional heteroatoms selected from N, NR$^{a2}$, O, and S(O)$_p$;

R$^c$ is, independently at each occurrence, H, OR$^a$, Cl, F, Br, =O, CN, NO$_2$, CF$_3$, CH$_2$F, CHF$_2$, —CF$_2$CF$_3$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, (CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, —(CH$_2$)$_r$—C$_{3-6}$ carbocycle substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^d$ is, independently at each occurrence, C$_{1-6}$ alkyl, OR$^a$, Cl, F, Br, =O, CN, NO$_2$, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, CF$_3$, C$_{3-6}$ carbocycle and a 5–6 membered heterocycle consisting of carbon atoms and 1–4 heteroatoms selected from the group consisting of N, O, and S(O)$_p$;

R$^9$ is, independently at each occurrence, H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^c$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$ and substituted with 0–2 R$^{c1}$; and R$^{10}$ is, independently at each occurrence, H, —(CR$^a$R$^{a1}$)$_t$ NR$^a$R$^{a1}$, —(CR$^a$R$^{a1}$)$_r$C(O)NR$^a$OH, —(CR$^a$R$^{a1}$)$_t$C(O) (CR$^a$R$^{a1}$)$_s$R$^e$, —(CR$^a$R$^{a1}$)$_r$C(O)OR$^{a1}$, —(CR$^a$R$^{a1}$)$_r$C(O) NR$^a$R$^{a1}$, —(CR$^a$R$^{a1}$)$_r$NR$^a$C(O)R$^{a1}$, —(CR$^a$R$^{a1}$)$_r$OC(O) NR$^a$R$^{a1}$, —(CR$^a$R$^{a1}$)$_r$NR$^a$C(O)OR$^{a1}$, —(CR$^a$R$^{a1}$)$_r$S(O)$_p$ R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$ and substituted with 0–2 R$^{c1}$.

In a third aspect, the present invention includes compounds of Formula (I) or a stereoisomer or pharmaceutically acceptable salt form thereof, wherein:

L is —(CR$^2$R$^3$)—, —(CR$^2$R$^3$)—CH$_2$—, —(CR$^2$R$^3$)—(CH$_2$)$_2$—, —CH$_2$—(CR$^4$R$^5$)—, or —CH$_2$—(CR$^4$R$^5$)—CH$_2$—;

alternatively, L is selected from the group:

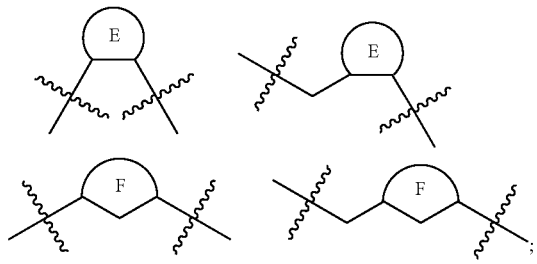

R$^2$ is Q$^1$, C$_{1-6}$ alkylene-Q$^1$, C$_{2-6}$ alkenylene-Q$^1$, C$_{2-6}$ alkynylene-Q$^1$, —(CH$_2$)$_r$O(CH$_2$)$_s$—Q$^1$, —(CH$_2$)$_r$NR$^a$ (CH$_2$)$_s$—Q$^1$, —(CH$_2$)$_r$C(O)(CH$_2$)$_s$—Q$^1$, —(CH$_2$)$_r$C(O)O (CH$_2$)$_s$—Q$^1$, (CH$_2$)$_r$C(O)NR$^a$(CH$_2$)$_s$—Q, —(CH$_2$)$_r$NR$^a$C (O)(CH$_2$)$_s$—Q$^1$, —(CH$_2$)$_r$S(O)$_p$(CH$_2$)$_s$—Q$^1$, —(CH$_2$)$_r$SO$_2$NR$^a$(CH$_2$)$_s$—Q$^1$, or —(CH$_2$)$_r$NR$^a$SO$_2$(CH$_2$)$_s$—Q$^1$;

R$^3$ is Q, C$_{1-6}$ alkylene-Q, C$_{2-6}$ alkenylene-Q, C$_{2-6}$ alkynylene-Q, —(CH$_2$)$_r$O(CH$_2$)$_s$—Q, —(CH$_2$)$_r$NR$^a$(CH$_2$)$_s$—Q, —(CH$_2$)$_r$C(O)(CH$_2$)$_s$—Q, —(CH$_2$)$_r$C(O)O(CH$_2$)$_s$—Q, —(CH$_2$)$_r$C(O)NR$^a$R$^{a1}$, —(CH$_2$)$_r$C(O)NR$^a$(CH$_2$)$_s$—Q, —(CH$_2$)$_r$NR$^a$C(O)(CH$_2$)$_s$—Q, —(CH$_2$)$_r$S(O)$_p$(CH$_2$)$_s$—Q, —(CH$_2$)$_r$SO$_2$NR$^a$(CH$_2$)$_s$—Q, or —(CH$_2$)$_r$NR$^a$SO$_2$(CH$_2$)$_s$—Q;

Q is, independently at each occurrence, H, a C$_{3-10}$ carbocycle substituted with 0–3 R$^d$, or a 5–10 membered heterocycle consisting of carbon atoms and 1–4 heteroatoms selected from the group consisting of N, O, and S(O)$_p$, and substituted with 0–3 R$^d$;

R$^4$ is H or C$_{1-6}$ alkyl;

R$^5$ is H or C$_{1-6}$ alkyl;

alternatively, R$^2$ and R$^3$, together with the carbon atom to which they are attached, combine to form a 3–8 membered carbocyclic or heterocyclic ring consisting of carbon atoms, 0–2 ring heteroatoms selected from O, N, NR$^{10}$, and S(O)$_p$, and 0–2 double bonds, and substituted with 0–2 R$^9$;

alternatively, R$^4$ and R$^5$, together with the carbon atom to which they are attached, combine to form a 3–8 membered carbocyclic or heterocyclic ring consisting of carbon atoms, 0–2 ring heteroatoms selected from O, N, NR$^{10}$, and S(O)$_p$, and 0–2 double bonds, and substituted with 0–2 R$^9$;

ring E is a C$_{3-7}$ cycloalkyl substituted with 0–2 R$^c$, a C$_{4-7}$ cycloalkenyl substituted with 0–2 R$^c$, phenyl substituted with 0–3 R$^c$, or a 5–7 membered heterocyclic ring consisting of carbon atoms and 0–2 ring heteroatoms selected from O, N, NR$^{10}$, and S(O)$_p$, and 0–2 double bonds, and substituted with 0–3 R$^c$;

ring F is a C$_{4-7}$ cycloalkyl substituted with 0–2 R$^c$, a C$_{4-7}$ cycloalkenyl substituted with 0–2 R$^c$, phenyl substituted with 0–3 R$^c$, or a 5–7 membered heterocyclic ring consisting of carbon atoms and 0–2 ring heteroatoms selected from O, N, NR$^{10}$, and S(O)$_p$, and 0–2 double bonds, and substituted with 0–3 R$^c$;

U is O, C(O), C(O)NR$^{a1}$, NR$^{a1}$C(O), S(O)$_p$, S(O)$_p$NR$^{a1}$, or NR$^{a1}$S(O)$_p$;

X is absent, or is methylene or ethylene;

Z is a C$_{4-8}$ cycloalkyl substituted with 0–3 R$^b$, a C$_{4-8}$ cycloalkenyl substituted with 0–3 R$^b$, phenyl substituted with 0–4 R$^b$, naphthyl substituted with 0–5 R$^b$, or a heterocycle substituted with 0–3 R$^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

U$^a$ is absent or is O, NR$^{a1}$, C(O), C(O)NR$^{a1}$, NR$^{a1}$C(O), S(O)$_p$, S(O)$_p$NR$^{a1}$, or NR$^{a1}$S(O)$_p$;

R$^{a3}$ is, independently at each occurrence, H, C$_{1-6}$ alkyl, C$_{2-6}$ alkenyl, or —(CH$_2$)$_r$-3–8 membered carbocyclic or heterocyclic ring consisting of carbon atoms and 0–2 ring heteroatoms selected from N, NR$^{a2}$, O, and S(O)$_p$, and substituted with 0–3 R$^{c1}$;

R$^c$ is, independently at each occurrence, H, OR$^a$, Cl, F, Br, =O, CF$_3$, CH$_2$F, CHF$_2$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O) NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, C$_{3-6}$ cycloalkyl substituted with 0–2 R$^{c1}$, phenyl substituted with 0–2 R$^{c1}$, or a 5–6 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 5–7 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^d$ is, independently at each occurrence, C$_{1-6}$ alkyl, OR$^a$, Cl, F, Br, =O, —NR$^a$R$^{a1}$, —C(O)R$^a$, —C(O)OR$^a$, —C(O) NR$^a$R$^{a1}$, —S(O)$_2$NR$^a$R$^{a1}$, —NR$^a$S(O)$_2$R$^{a3}$, —S(O)$_p$R$^{a3}$, CF$_3$ or phenyl;

R$^9$ is, independently at each occurrence, H, —(CR$^a$R$^{a1}$)$_r$NR$^a$R$^{a1}$, —(CR$^a$R$^{a1}$)$_r$C(O)(CR$^a$R$^{a1}$)$_s$R$^e$, —(CR$^a$R$^{a1}$)$_r$C(O)

OR$^{a1}$, —(CR$^a$R$^{a1}$)$_r$C(O)NR$^a$R$^{a1}$, —(CR$^a$R$^{a1}$)$_r$NR$^a$C(O) R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^c$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

R$^{10}$ is, independently at each occurrence, H, —(CR$^a$R$^{a1}$)$_t$NR$^a$R$^{a1}$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^c$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

r, at each occurrence, is selected from 0, 1, 2, and 3;

s, at each occurrence, is selected from 0, 1, 2, and 3; and t, at each occurrence, is selected from 1, 2, and 3.

In a fourth aspect, the present invention includes compounds of Formula (1) or a stereoisomer or pharmaceutically acceptable salt form thereof, wherein:

Q is, independently at each occurrence, H, a C$_{3-8}$ carbocycle substituted with 0–3 R$^d$, or a 5–10 membered heterocycle consisting of carbon atoms and 1–4 heteroatoms selected from the group consisting of N, O, and S(O)$_p$, and substituted with 0–3 R$^d$;

Q$^1$ is, independently at each occurrence, H, a C$_{3-10}$ carbocycle substituted with 0–5 R$^d$, or a 5–10 membered heterocycle consisting of carbon atoms and 1–4 heteroatoms selected from the group consisting of N, NR$^{10}$, O, and S(O)$_p$, and substituted with 0–3 R$^d$;

Z is phenyl substituted with 0–3 R$^b$, naphthyl substituted with 0–5 R$^b$, pyridyl substituted with 0–3 R$^b$, thienyl substituted with 0–2 R$^b$, thiazolyl substituted with 0–2 R$^b$, oxazolyl substituted with 0–2 R$^b$, isoxazolyl substituted with 0–2 R$^b$, or imidazolyl substituted with 0–2 R$^b$;

Z$^a$ is phenyl substituted with 0–3 R$^c$, naphthyl substituted with 0–3 R$^c$, or a heterocycle substituted with 0–3 R$^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

R$^a$ is, independently at each occurrence, H, C$_{1-6}$ alkyl, phenyl, or benzyl;

R$^{a1}$ is, independently at each occurrence, H, C$_{1-6}$ alkyl, phenyl, or benzyl;

R$^{a3}$ is, independently at each occurrence, H, C$_{1-6}$ alkyl, phenyl, or benzyl;

R$^c$ is, independently at each occurrence, H, OR$^a$, Cl, F, Br, =O, CF$_3$, CH$_2$F, CHF$_2$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, phenyl substituted with 0–2 R$^{c1}$, or a 5–6 membered heterocycle consisting of carbon atoms and 1–4 heteroatoms selected from the group consisting of N, O, and S(O)$_p$ and substituted with 0–2 R$^{c1}$;

alternatively, when two R$^c$ groups are attached to the same carbon atom, they form a 5–6 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–6 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^9$ is, independently at each occurrence, H, —(CR$^a$R$^{a1}$)$_r$NR$^a$R$^{a1}$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, —(CR$^a$R$^{a1}$)$_r$—C$_{3-7}$ carbocycle substituted with 0–2 R$^{c1}$, or —(CR$^a$R$^{a1}$)$_r$-5–6 membered heterocycle consisting of carbon atoms and 1–4 heteroatoms selected from the group consisting of N, O, and S(O)$_p$, and substituted with 0–2 R$^{c1}$; and R$^{10}$ is, independently at each occurrence, H, —(CR$^a$R$^{a1}$)$_t$NR$^a$R$^{a1}$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$.

In a fifth aspect, the present invention includes compounds of Formula (I) or a stereoisomer or pharmaceutically acceptable salt form thereof, wherein:

R$^2$ is Q$^1$, C$_{1-4}$ alkylene-Q$^1$, C$_{2-4}$ alkenylene-Q$^1$, C$_{2-4}$ alkynylene-Q$^1$, —(CH$_2$)$_r$O(CH$_2$)$_s$—Q$^1$, —(CH$_2$)$_r$NR$^a$(CH$_2$)$_s$—Q$^1$, —(CH$_2$)$_r$C(O)(CH$_2$)$_s$—Q$^1$, —(CH$_2$)$_r$C(O)O(CH$_2$)$_s$—Q$^1$, —(CH$_2$)$_r$C(O)NR$^a$(CH$_2$)$_s$—Q$^1$, —(CH$_2$)$_r$NR$^a$C(O)(CH$_2$)$_s$—Q$^1$, —(CH$_2$)$_r$S(O)$_p$(CH$_2$)$_s$—Q$^1$, —(CH$_2$)$_r$SO$_2$NR$^a$(CH$_2$)$_s$—Q$^1$, or —(CH$_2$)$_r$NR$^a$SO$_2$(CH$_2$)$_s$—Q$^1$;

R$^3$ is H, C$_{1-4}$ alkyl, C$_{2-4}$ alkenyl, or C$_{2-4}$ alkynyl;

R$^4$ is H or C$_{1-4}$ alkyl;

R$^5$ is H or C$_{1-4}$ alkyl;

alternatively, R$^2$ and R$^3$, together with the carbon atom to which they are attached, combine to form a 3–8 membered carbocyclic or heterocyclic ring consisting of carbon atoms, 0–2 ring heteroatoms selected from O, N, NR$^{10}$, and S(O)$_p$, and 0–2 double bonds;

alternatively, R$^4$ and R$^5$, together with the carbon atom to which they are attached, combine to form a 3–8 membered carbocyclic or heterocyclic ring consisting of carbon atoms, 0–2 ring heteroatoms selected from O, N, NR$^{10}$, and S(O)$_p$, and 0–2 double bonds;

Q$^1$ is, independently at each occurrence, H, a C$_{3-6}$ carbocycle substituted with 0–2 R$^d$, or a 5–6 membered heterocycle consisting of carbon atoms and 1–4 heteroatoms selected from the group consisting of N, NR$^{10}$, O, and S(O)$_p$, and substituted with 0–2 R$^d$;

ring E is a $C_{4-7}$ cycloalkyl substituted with 0–2 $R^c$, a $C_{4-7}$ cycloalkenyl substituted with 0–2 $R^c$, phenyl substituted with 0–2 $R^c$, or a heterocyclic ring substituted with 0–2 $R^c$ and selected from: furanyl, tetrahydrofuranyl, thienyl, thiazolyl, oxazolyl, imidazolyl, isothiazolyl, isoxazolyl, pyrazolyl, pyrrolyl, pyridyl, pyranyl, tetrahydropyranyl, pyrimidinyl,

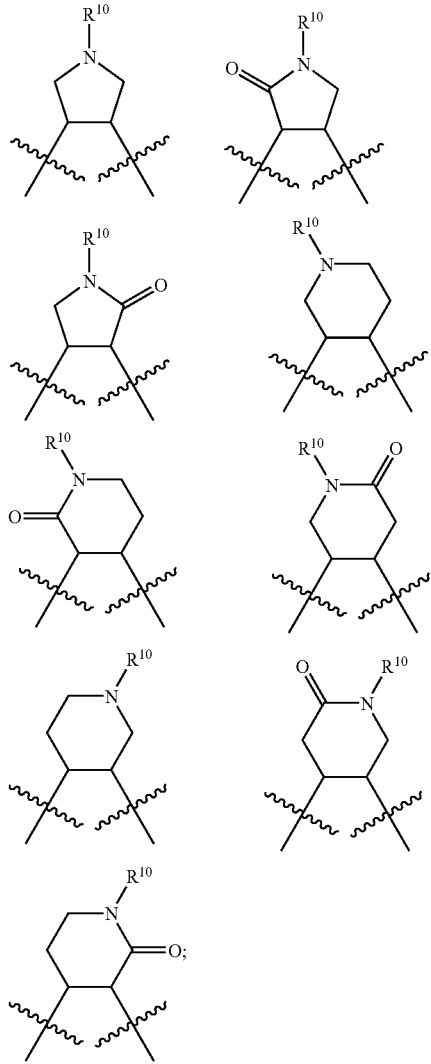

ring F a $C_{4-7}$ cycloalkyl substituted with 0–2 $R^c$, a $C_{4-7}$ cycloalkenyl substituted with 0–2 $R^c$, phenyl substituted with 0–2 $R^c$, or a heterocyclic ring substituted with 0–2 $R^c$ and selected from: pyridyl, pyranyl, tetrahydropyranyl, pyrimidinyl,

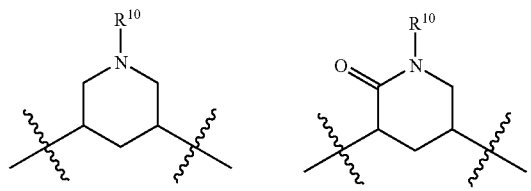

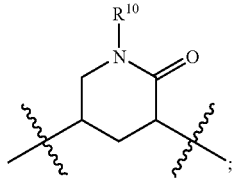

U is C(O), C(O)$NR^{a1}$, $NR^{a1}$C(O), S(O)$_p$, S(O)$_p$$NR^{a1}$, or $NR^{a1}$S(O)$_p$;

X is absent or is methylene;

Y is absent or is O;

Z is phenyl substituted with 0–3 $R^b$;

$U^a$ is absent or is 0;

$Y^a$ is absent or is 0;

$R^a$ is, independently at each occurrence, H, or $C_{1-4}$ alkyl;

$R^{a1}$ is, independently at each occurrence, H, or $C_{1-4}$ alkyl;

$R^{a3}$ is, independently at each occurrence, H, $C_{1-4}$ alkyl, phenyl, or benzyl;

$R^c$ is, independently at each occurrence, $C_{1-6}$ alkyl, $C_{2-6}$ alkenyl, $C_{2-6}$ alkynyl, $OR^a$, Cl, F, Br, =O, $CF_3$, $CH_2F$, $CHF_2$, $NR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, or phenyl;

alternatively, when two $R^c$ groups are attached to the same carbon atom, they form a 5–6 membered carbocyclic or heterocyclic spiro ring C substituted with 0–2 $R^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–6 membered carbocyclic or heterocyclic ring D substituted with 0–1 $R^{c1}$ and consisting of carbon atoms, 0–2 heteroatoms selected from the group consisting of N, O, and S(O)$_p$, and 0–3 double bonds;

$R^e$ is, independently at each occurrence, H, $C_{1-6}$ alkyl, $C_{1-6}$ alkoxy, phenoxy, benzoxy, $C_{3-6}$ carbocycle substituted with 0–2 $R^{c1}$, or a 5–6 membered heterocycle consisting of carbon atoms and 1–4 heteroatoms selected from the group consisting of N, O, and S(O)$_p$, and substituted with 0–2 $R^{c1}$; and $R^{10}$ is, independently at each occurrence, H, —(CH$_2$)$_t$$NR^aR^{a1}$, —(CH$_2$)$_rC(O)(CH$_2$)$_sR^e$, —(CH$_2$)$_rC(O)OR^{a1}$, —(CH$_2$)$_rC(O)NR^aR^{a1}$, —(CH$_2$)$_tNR^aC(O)R^{a1}$, —(CH$_2$)$_sS(O)_pR^{a3}$, —(CH$_2$)$_rSO_2NR^aR^{a1}$, —(CH$_2$)$_tNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —(CH$_2$)$_r$—$C_{3-10}$ carbocycle substituted with 0–2 $R^{c1}$, or —(CH$_2$)$_r$-5–10 membered heterocycle consisting of carbon atoms and 1–4 heteroatoms selected from the group consisting of N, O, and S(O)$_p$, and substituted with 0–2 $R^{c1}$.

In a sixth aspect, the present invention includes compounds of Formula (I) or a stereoisomer or pharmaceutically acceptable salt form thereof, wherein:

$R^2$ is H, $C_{1-4}$ alkyl, $C_{2-6}$ alkenyl, or $C_{2-6}$ alkynyl;

$R^3$ is H or $C_{1-4}$ alkylene;

$R^4$ is H or $C_{1-4}$ alkyl;

$R^5$ is H or $C_{1-4}$ alkyl;

alternatively, $R^2$ and $R^3$, together with the carbon atom to which they are attached, combine to form a $C_{3-7}$ cycloalkyl, a $C_{3-7}$ cycloalkenyl, or a 5–6 membered heterocyclic ring consisting of carbon atoms, 1 ring heteroatom selected from O, N, NR$^{10}$, and S(O)$_p$, and 0–2 double bonds;

alternatively, R$^4$ and R$^5$, together with the carbon atom to which they are attached, combine to form a C$_{3-7}$ cycloalkyl, a C$_{3-7}$ cycloalkenyl, or a 5–6 membered heterocyclic ring consisting of carbon atoms, 1 ring heteroatom selected from O, N, NR$^{10}$, and S(O)$_p$, and 0–2 double bonds;

W is (CH$_2$)$_m$;

Y is absent;

Z is phenyl substituted with 0–1 R$^b$;

Z$^a$ is phenyl substituted with 0–3 R$^c$, naphthyl substituted with 0–3 R$^c$, or a heterocycle substituted with 0–3 R$^c$ and selected from the group: pyridyl, quinolinyl, tetrahydroquinolinyl, isoquinolinyl, tetrahydro-isoquinolinyl, imidazolyl, pyridoimidazolyl, benzimidazolyl, indolyl, indolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

R$^b$ is, independently at each occurrence, C$_{1-6}$ alkyl, OR$^a$, Cl, F, Br, NR$^a$R$^{a1}$, C(O)R$^a$, C(O)OR$^a$, C(O)NR$^a$R$^{a1}$, S(O)$_2$NR$^a$R$^{a1}$, NR$^a$S(O)$_2$R$^{a3}$, S(O)$_p$R$^{a3}$, or CF$_3$;

R$^c$ is, independently at each occurrence, C$_{1-6}$ alkyl, C$_{2-6}$ alkenyl, C$_{2-6}$ alkynyl, OR$^a$, Cl, F, Br, =O, CF$_3$, —NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, or —(CR$^a$R$^{a1}$)$_r$NR$^a$SO$_2$R$^{a3}$;

alternatively, when two R$^c$ groups are attached to the same carbon atom, they form a 5–6 membered carbocyclic or heterocyclic spiro ring C consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–6 membered carbocyclic or heterocyclic ring D consisting of carbon atoms, 0–2 heteroatoms selected from the group consisting of N, O, and S(O)$_p$, and 0–3 double bonds;

R$^e$ is, independently at each occurrence, H, C$_{1-6}$ alkyl, C$_{1-6}$ alkoxy, phenoxy, benzoxy, phenyl substituted with 0–1 R$^{e1}$, or a 5–6 membered heterocycle consisting of carbon atoms and 1–4 heteroatoms selected from the group consisting of N, O, and S(O)$_p$, and substituted with 0–1 R$^{c1}$;

R$^{10}$ is, independently at each occurrence, H, —(CH$_2$)$_r$C(O)(CH$_2$)$_s$R$^e$, —(CH$_2$)$_r$C(O)OR$^a$, —(CH$_2$)$_r$C(O)NR$^a$R$^{a1}$, —(CH$_2$)$_r$S(O)$_p$R$^{a3}$, —(CH$_2$)$_r$SO$_2$NR$^a$R$^{a1}$, C$_{1-4}$ alkyl substituted with 0–1 R$^{c1}$, C$_{2-4}$ alkenyl substituted with 0–1 R$^{c1}$, C$_{2-4}$ alkynyl substituted with 0–1 R$^{c1}$, —(CH$_2$)$_r$—C$_{3-6}$ cycloalkyl substituted with 0–2 R$^{c1}$, —(CH$_2$)$_r$-phenyl substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;

m, at each occurrence, is selected from 0, 1, and 2;

r, at each occurrence, is selected from 0, 1, and 2; and s, at each occurrence, is selected from 0, 1, and 2.

In a seventh aspect, the present invention includes compounds of Formula (I) or a stereoisomer or pharmaceutically acceptable salt form thereof, wherein:

L is selected from: —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—,

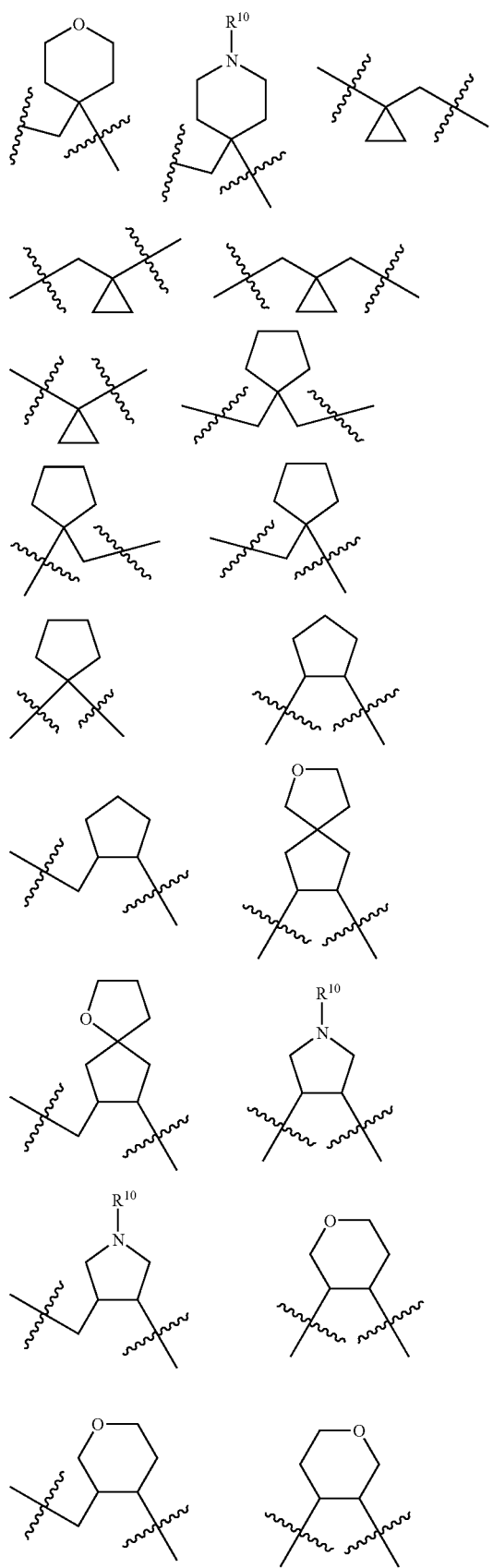

-continued

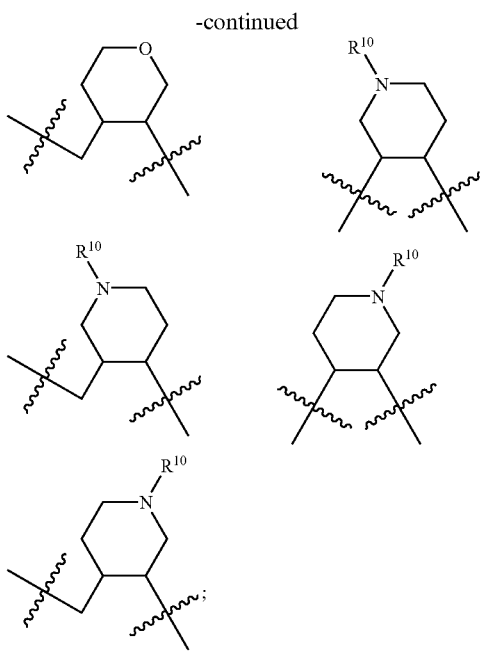

W is $(CH_2)_m$;
Y is absent;
Z is phenyl substituted with 0–1 $R^b$;
$Z^a$ is a heterocycle substituted with 0–3 $R^c$ and selected from the group: quinolinyl, isoquinolinyl, and 1,1-dioxido-2,3-dihydro-4H-1,4-benzothiazin-4-yl; and
$R^{10}$ is H, methyl, ethyl, isopropyl, isobutyl, 2-propynyl, acetyl, 2,2-dimethylpropanoyl, t-butoxycarbonyl, 3-methylbutanoyl, isobutyryl, isonicotinoyl, phenoxyacetyl, methanesulfonyl, 3-pyridinylmethyl, 4-pyridinylmethyl, 3-pyridinylcarbonyl, 4-piperidinylcarbonyl, 4-morpholinylacetyl, 4-morpholinomethyl, or [1-(t-butoxycarbonyl)-4-piperidinyl]carbonyl.

In an eighth aspect, the present invention provides a compound selected from Examples 1–37 or a stereoisomer or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, aggrecanase, or a combination thereof.

In another embodiment, the present invention provides a novel method of treating a disease or condition, wherein the disease or condition is selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyagia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt form thereof; and,
  (c) a package insert stating that the pharmaceutical composition can be used for the treatment of an inflammatory disorder.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt form thereof; and,
  (c) a package insert stating that the pharmaceutical composition can be used in combination with a second therapeutic agent to treat an inflammatory disorder.

In another preferred embodiment, the present invention provides a novel article of manufacture, further comprising:
(d) a second container;
wherein components (a) and (b) are located within the second container and component (c) is located within or outside of the second container.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "independently selected from", "independently, at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$, wherein v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Triazolethione or triazolone heterocycles of formula (I) wherein A is sulfur or oxygen can be prepared by a variety of routes known in the literature. Scheme 1 outlines several of the most prevalent methods.

The first method shown in Scheme 1 has been the most widely used approach, typically providing the best yields (see Ladduwahetty, T. et al. *J. Med. Chem.* 1996, 39, 2907–2914 and Mazzone, G. et al. *Eur. J. Med. Chem. Chim. Ther.* 1986, 21, 277–284). For instance, acid 1 is reacted with either thiosemicarbazide (2a) or semicarbazide (2b) to provide the respective amides 3a or 3b. Treatment of 3a or 3b with aqueous sodium hydroxide solution at reflux temperatures gives the corresponding triazolethione 4a or triazolone 4b. Other basic media such as sodium methoxide or sodium ethoxide will also induce cyclization.

An alternative method involves a two step procedure starting from an ester as shown in route (2) Scheme 1 (see for example: Mullican, M. D. et al. *J. Med. Chem.* 1993, 36, 1090–1099 and Demirayak, S. et al. *Farmaco* 1993, 48, 707–712). The addition of hydrazine to a methyl ester such as 5 would furnish hydrazide 6. Further treatment with either ammonium thiocyanate or sodium cyanate would provide the respective heterocycles 4a or 4b.

Route (3) in Scheme 1 illustrates the use of acid chlorides in the formation of triazolethiones. Addition of ammonium thiocyanate to an acid chloride 7 would provide the nitrene-like compound 8 which can be trapped with hydrazine to give the triazolethione 4a (see Ahmed, A. F. et al. *J. Chem. Res. Miniprint* 1998, 9, 2056–2061).

Route (4) in Scheme 1 utilizes the nitrile functional group to arrive at heterocycles 4a and 4b. This method proceeds through two imidate-type intermediates 10 and 11 (see Malbec, F. et al. *J. Heterocycl. Chem.* 1984, 21, 1689–1698 and Dowell, R. I. et al. *Eur. J. Med. Chem. Chim. Ther.* 1993, 28, 513–516).

Route (5) of Scheme 1 details an oxidative approach to triazolones 4b. Imine formation between aldehyde 12 and semicarbazide 2b followed by oxidative cyclization of intermediate 13 with $S_2Cl_2$ would give triazolone 4b (Milcent, R. and Nguyen, T-H. *J. Heterocycl. Chem.* 1986, 23, 881–883).

Scheme 1

(1) Triazolethiones and triazolones from caboxylic acids

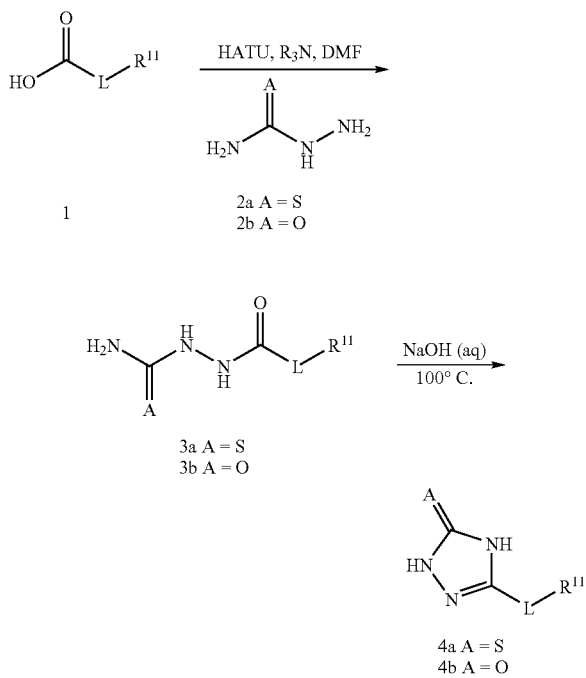

2a A = S
2b A = O

3a A = S
3b A = O

4a A = S
4b A = O

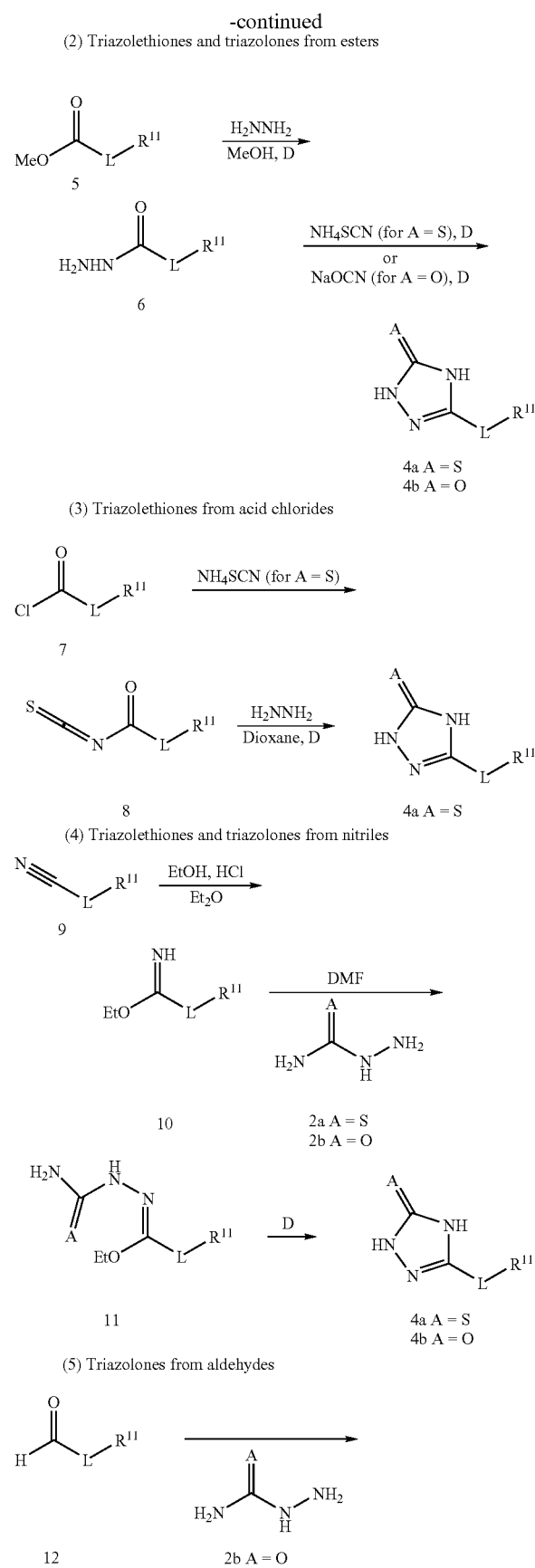

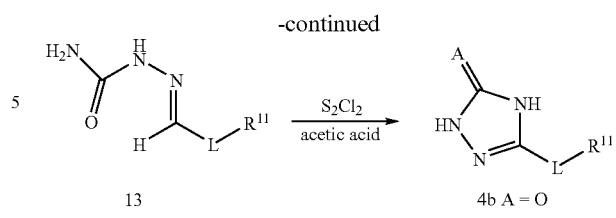

The L moiety in formula (I) can be a wide range of carbocycles or heterocycles. The only structural requirement for L is that it contains a functional group that can be manipulated to an oxidation state similar to a carboxylic acid. This type of functionality provides a necessary handle for constructing the triazolethione or triazolone ring according to the methods presented in Scheme 1. The examples covered under the present invention have been synthesized following route (1) in Scheme 1.

Compounds for which L in formula (I) is a linear alkyl derivative, a carbocycle or a heterocycle can be synthesized following the representative routes described below.

For the preparation of linear alkyl and substituted alkyl derivatives, a route similar to that detailed in Scheme 2 can be used. Ester 14 is coupled with carboxylic acid 15 with a peptide coupling reagent to give amide 16. After saponification, the carboxylic acid 17 can be reacted with thiosemicarbazide 2a or semicarbazide 2b to furnish the amides 18a or 18b respectively. Finally ring formation is facilitated by refluxing a solution of 18a or 18b in aqueous sodium hydroxide solution to provide the corresponding triazolethione 19a or triazolone 19b.

Scheme 2
Substituted Linear Alkyl Triazolethiones and Triazolones

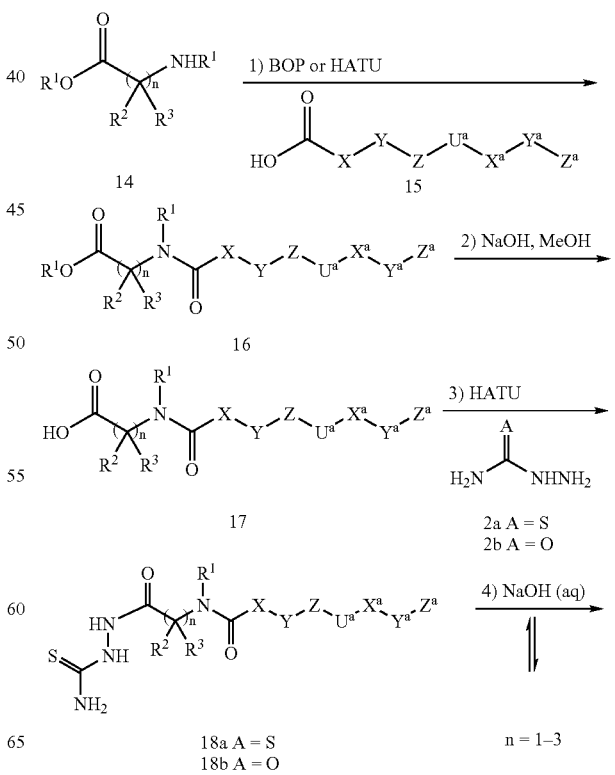

-continued

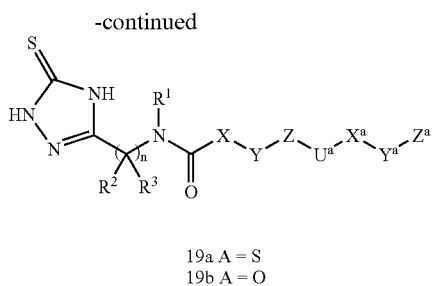

19a A = S
19b A = O

Cyclic-β-amino derivatives are prepared as shown in Schemes 3 and 4. Both α,β-cyclic compounds such as 20 and β,β-cyclic compounds such as 24 readily undergo the four step sequence of 1) coupling to acid 15, 2) saponification, 3) coupling with 2a or 2b, and 4) base induced cyclization to give either the triazolethiones (23a, 27a) or triazolones (23b, 27b). Ring B in each case may be a substituted carbocyclic or heterocyclic ring.

Scheme 3
α,β-Cyclic Triazolethiones and Triazolones

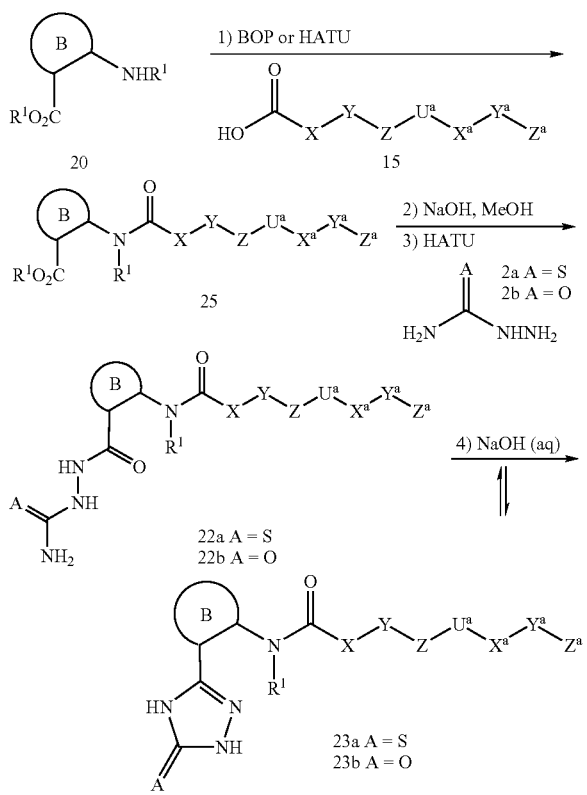

Scheme 4
β,β-Cyclic Triazolethiones and Triazolones

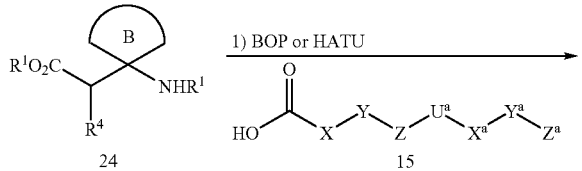

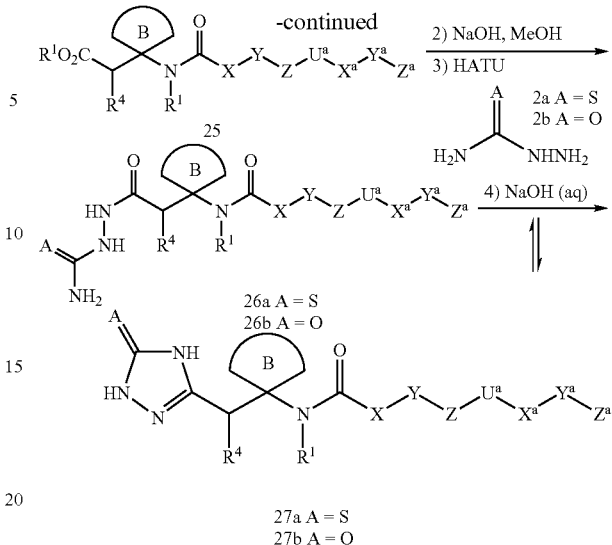

Sulfone derivatives such as 31a–b can also be prepared as shown in Scheme 5. They are readily available from methyl esters 30 respectively through the three step sequence outlined previously.

Scheme 5
Synthesis of Sulfone Derivatives

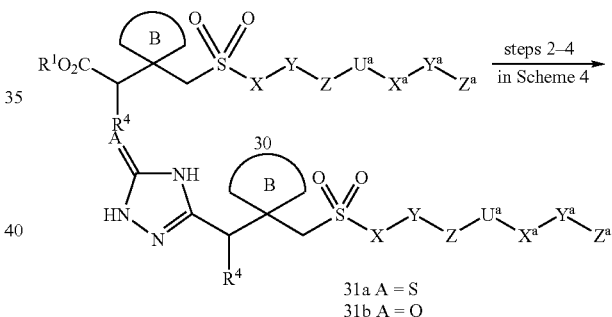

When ring B in compounds 23a or 23b (see Scheme 3) is a Boc-protected pyrrolidine or piperidine, the ring nitrogen may be functionalized as outlined in Scheme 6. Removal of the Boc protecting group of compounds 32a–b or 33a–b with trifluoroacetic acid would give the free amines 34a–b or 35a–b. Acylation of the ring nitrogen can be accomplished using either carboxylic acid anhydrides or standard peptide coupling conditions to provide the amides 36a–b or 37a–b.

Scheme 6
Acylation of Pyrrolidine and Piperidine Systems

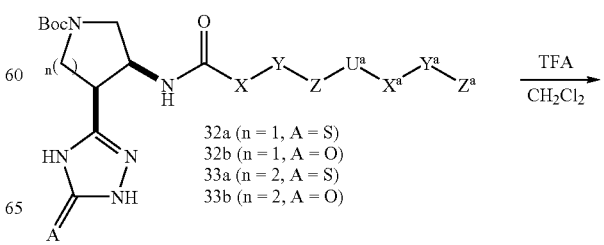

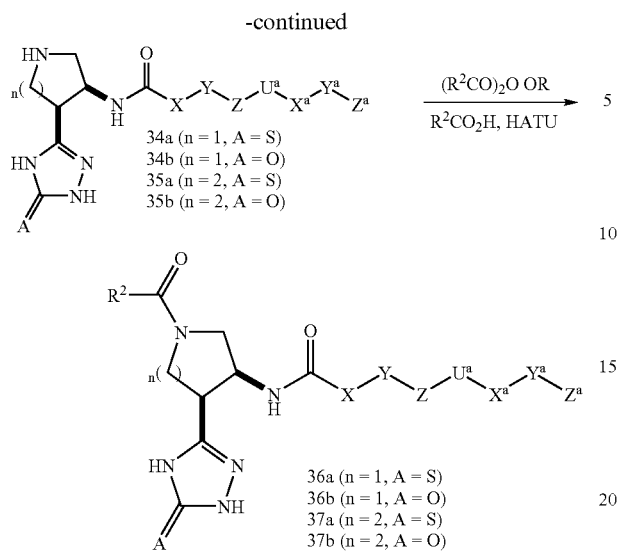

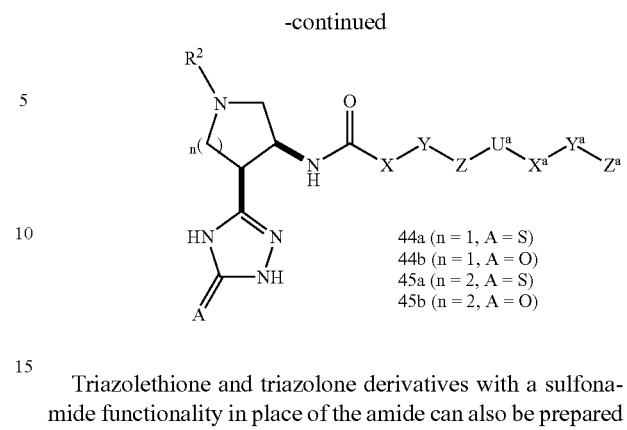

Triazolethione and triazolone derivatives with a sulfonamide functionality in place of the amide can also be prepared as shown in Scheme 8. Reaction of sulfonyl chloride 46 with amine 20 under standard conditions would give the sulfonamide 47. Further conversion to triazolethione 48a or triazolone 48b can be accomplished as previously discussed.

An alternative approach to that outlined in Scheme 6 involves functionalization of the ring nitrogen prior to the formation of the triazolethione or triazolone ring. Treatment of esters 38 or 39 with trifluoroacetic acid would facilitate the removal of the Boc protecting group as shown in Scheme 7. The resulting pyrrolidine 40 or piperidine 41 could then be functionalized to various tertiary amines, amides, carbamides, ureas, sulfonamides, and sulfonyl ureas following procedures well known in the literature. Conversion of esters 42 or 43 to the corresponding triazolethiones (44a or 45a) or triazolones (44b or 45b) can be accomplished using the typical sequence.

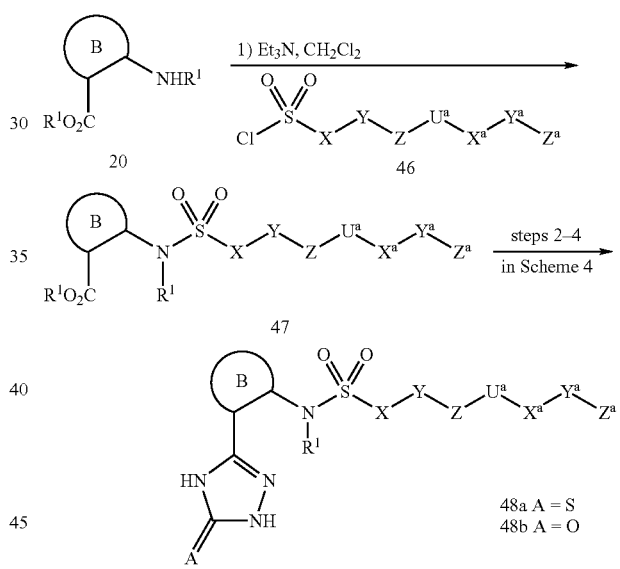

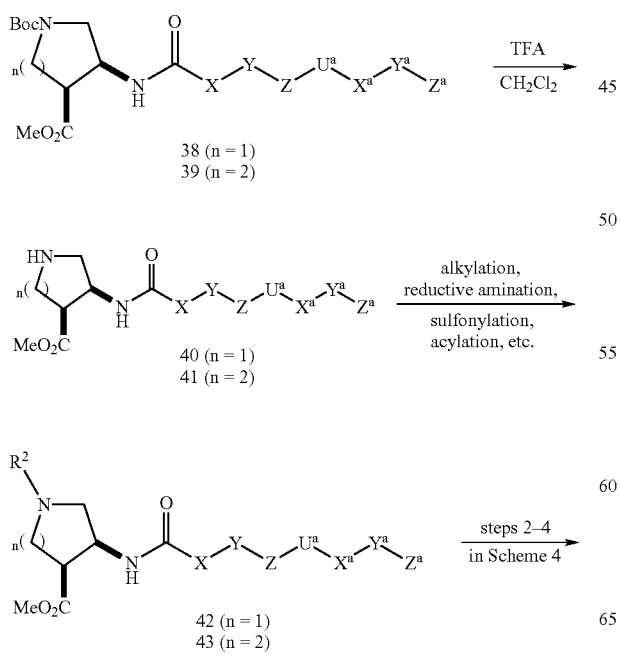

One stereoisomer of a compound of formula (I) may display superior activity compared with others. Thus, all possible stereoisomers are considered to be a part of the present invention.

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "µL" for microliter or microliters, "¹H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R", "S", "cis" and "trans" are stereochemical designations familiar to those skilled in the art.

Example 1

4-(2-Methyl-quinolin-4-ylmethoxy)-N-[3-(5-thioxo-4,5-dihydro-1H-[1,2,4]triazol-3-yl)-propyl]-benzamide (1a)
To a solution of ethyl 4-aminobutyrate hydrochloride (201 mg, 1.2 mmol) and triethylamine (486 mg, 4.8 mmol) in methylene chloride (10 mL) was added 4-(2-methyl-quinolin-4-ylmethoxy)-benzoyl chloride hydrochloride (500 mg, 1.4 mmol; see WO01/70734 for preparation). The reaction was allowed to stir for 2 h at rt. The mixture was partitioned between ethyl acetate and water. The layers were separated and the organic layer washed with saturated sodium bicarbonate solution and brine. After drying over magnesium sulfate, the organic layer was filtered and concentrated. The crude material was purified by silica gel chromatography to provide the desired product (690 mg, >100%). MS found: $(M+H)^+=407$.

(1b)
To a solution of the ester (1.2 mmol) from reaction (1a) in methanol (15 mL) was added aqueous sodium hydroxide solution (10 mL, 1 N). After 90 min, the pH of the solution was adjusted with aqueous hydrochloric acid to pH ~4–5. The precipitate that formed was collected by filtration and dried to give the desired carboxylic acid (300 mg, 66%). MS found: $(M+H)^+=379$.

(1c)
To a solution of the carboxylic acid (197 mg, 0.47 mmol) from reaction (1b), thiosemicarbazide (48 mg, 0.52 mmol), and N-methylmorpholine (144 mg, 1.42 mmol) in dimethylformamide was added O-(7-azabenzotriazol-1-yl)-N,N,N',N'-tetramethyluronium hexafluorophosphate (HATU) (217 mg, 0.57 mmol). The reaction was allowed to stir overnight and subsequently quenched with water. The mixture was extracted with ethyl acetate (20 mL×4). The organic layer was washed with brine, dried, and concentrated. Purification of the crude material by reverse phase HPLC (10–100% acetonitrile/water) furnished the desired compound as a trifluoroacetic acid salt (197 mg, 73%). MS found: $(M+H)^+=452$.

(1d)
A suspension of the thiosemicarbazide amide (85 mg, 0.17 mmol) from reaction (1c) in aqueous sodium hydroxide (3.4 mL, 2 M) was heated at reflux for 2 h. Solution became homogeneous once reflux temperature was reached. Solution was cooled to 0° C. and neutralized with aqueous hydrochloric acid (6.8 mL, 1 N). The precipitate that formed was collected and dried to give the desired triazolethione (60 mg, 82%). MS found: $(M+H)^+=434$.

Example 2

4-(2-Methyl-quinolin-4-ylmethoxy)-N-[2-(5-thioxo-4,5-dihydro-1H-[1,2,4]triazol-3-yl)-ethyl]-benzamide (2a)
To a solution of β-alanine methyl ester (500 mg, 3.58 mmol), 4-(2-methyl-quinolin-4-ylmethoxy)-benzoic acid (1.26 g, 4.30 mmol), and diisopropylethylamine (2.5 mL, 14.3 mmol) in dimethylformamide was added O-(7-azabenzotriazol-1-yl)-N,N,N',N'-tetramethyluronium hexafluorophosphate (HATU) (2.04 g, 5.37 mmol). The reaction was allowed to stir overnight. The mixture was partitioned between ethyl acetate and water. The organic layer was washed with water, saturated sodium bicarbonate solution, and brine. After drying, the ethyl acetate layer was concentrated and the remaining crude material purified by silica gel chromatography to provide the desired amide (1.0 g, 74%). MS found: $(M+H)^+=379$.

(2b)
Following a procedure analogous to that used in reaction (1b), the ester (1.0 g, 2.65 mmol) from reaction (2a) was reacted with aqueous lithium hydroxide solution for 2 h to give the desired carboxylic acid (750 mg, 71%). MS found: $(M+H)^+=365$.

(2c)
Following a procedure analogous to that used in reaction (1c), the carboxylic acid (200 mg, 0.5 mmol) from reaction (2b) was reacted with thiosemicarbazide (50 mg, 0.55 mmol) for 3 h. The reaction was quenched with water and extracted with ethyl acetate (20 mL×2). The precipitate that formed from the organic layer was collected to give the thiosemicarbazide amide (174 mg, 80%). MS found: $(M+H)^+=438$.

(2d)
Following a procedure analogous to that used in reaction (1d), the thiosemicarbazide amide (50 mg, 0.11 mmol) from reaction (2c) was heated at reflux with aqueous sodium hydroxide solution to give the desired triazolethione (40 mg, 83%). MS found: $(M+H)^+=420$.

Example 3

4-(2-Methyl-quinolin-4-ylmethoxy)-N-(5-thioxo-4,5-dihydro-1H-[1,2,4]triazol-3-ylmethyl)-benzamide (3a)
To a solution of glycine ethyl ester hydrochloride (74 mg, 0.53 mmol), 4-(2-methyl-quinolin-4-ylmethoxy)-benzoic acid (155 mg, 0.53 mmol), and triethylamine (160 mg, 1.59 mmol) in dimethylformamide was added benzotriazol-1-yloxytris(dimethylamino)phosphonium hexafluorophosphate (281 mg, 0.63 mmol). After stirring for 30 min, the reaction was quenched with water. The mixture was extracted with ethyl acetate (15 mL×2) and the combined organic layers washed with brine (10 mL), dried over magnesium sulfate, and concentrated. The crude product was purified by silica gel chromatography (4% methanol/methylene chloride) to give the desired product (186 mg, 93%). MS found: $(M+H)^+=379$.

(3b)

Following a procedure analogous to that used in reaction (1b), the ester (180 mg, 0.48 mmol) from reaction (3a) was reacted with aqueous sodium hydroxide solution (2.9 mL, 1 N) for 30 min to furnish the desired carboxylic acid (143 mg, 86%). MS found: $(M+H)^+=351$.

(3c)

Following a procedure analogous to that used in reaction (1c), the carboxylic acid (130 mg, 0.37 mmol) from reaction (3b) was reacted with thiosemicarbazide (37 mg, 0.41 mmol) for 1 h. The reaction was quenched with water and extracted with ethyl acetate (15 mL×2). A solid precipitated from the organic layer and was collected to give the thiosemicarbazide amide (150 mg, 96%).

(3d)

Following a procedure analogous to that used in reaction (1d), the thiosemicarbazide amide (100 mg, 0.24 mmol) from reaction (3c) was heated at reflux with aqueous sodium hydroxide solution to give the desired triazolethione (70 mg, 73%). MS found: $(M+H)^+=406$.

Example 4

N-[1,1-Dimethyl-2-(5-thioxo-4,5-dihydro-1H-[1,2,4]triazol-3-yl)-ethyl]-4-(2-methyl-quinolin-4-yl-methoxy)-benzamide (4a)

A solution of N-(2-Hydroxycarbamoyl-1,1-dimethyl-ethyl)-4-(2-methyl-quinolin-4-ylmethoxy)-benzamide (240 mg, 0.59 mmol; see WO01/70734 for preparation) in methanol (2 mL) and aqueous sodium hydroxide (0.9 mL, 2 M) was heated at reflux for 2 h. The mixture was cooled to 0° C. and neutralized. The solution was evaporated to dryness and the remaining residue used in the next step without further purification/characterization.

(4b)

Following a procedure analogous to that used in reaction (1c), the crude material (0.59 mmol) from reaction (4a) was reacted with thiosemicarbazide (59 mg, 0.65 mmol) overnight. The reaction was quenched with water and extracted with ethyl acetate (100 mL×2). The combined organic layers were washed with brine (50 mL), dried over magnesium sulfate, and concentrated. Purification of the crude material by reverse phase HPLC (10–100% acetonitrile/water) gave the desired thiosemicarbazide amide as a trifluoroacetic acid salt (13 mg, 4%). MS found: $(M+H)^+=466$.

(4c)

Following a procedure analogous to that used in reaction (1d), the thiosemicarbazide amide (11 mg, 0.019 mmol) from reaction (4b) was heated at reflux with aqueous sodium hydroxide solution to give the desired triazolethione (10 mg, 100%). MS found: $(M+H)^+=448$.

Example 5

4-[4-(2-Methyl-quinolin-4-ylmethoxy)-benzoylamino]-4-(5-thioxo-4,5-dihydro-1H-[1,2,4]triazol-3-ylmethyl)-piperidine-1-carboxylic acid tert-butyl ester trifluoroacetate (5a)

Following a procedure analogous to that used in reaction (1b), 4-methoxycarbonylmethyl-4-[4-(2-methyl-quinolin-4-ylmethoxy)-benzoylamino]-piperidine-1-carboxylic acid tert-butyl ester (125 mg, 0.228 mmol; see WO01/70734 for preparation) was reacted with aqueous sodium hydroxide solution (0.34 mL, 2 N) in methanol (1 mL) and tetrahydrofuran (1 mL). After acidifying to pH ~4 with aqueous hydrochloric acid, the solution was evaporated to dryness to give the carboxylic acid. This material was used without further purification or characterization. MS found: $(M+H)^+=534$.

(5b)

Following a procedure analogous to that used in reaction (1c), the carboxylic acid (0.228 mmol) from reaction (5a) was reacted with thiosemicarbazide (23 mg, 0.25 mmol) for 3 h. The reaction was quenched with water and extracted with ethyl acetate. The organic layer was washed with water (3×), and brine, dried over magnesium sulfate, and concentrated to give the crude thiosemicarbazide amide (assumed quantitative recovery). MS found: $(M+H)^+=607$.

(5c)

Following a procedure analogous to that used in reaction (1d), the thiosemicarbazide amide (0.228 mmol) from reaction (5b) was heated at reflux with aqueous sodium hydroxide solution for 1.5 h. After cooling to rt, the reaction was neutralized with aqueous hydrochloric acid. Majority of the water was removed under reduced pressure. Purification of the crude material by reverse phase HPLC (20–60% acetonitrile/water) provided the desired triazolethione (10 mg, 6% for 3 steps). MS found: $(M+H)^+=589$.

Example 6

4-(2-Methyl-quinolin-4-ylmethoxy)-N-[4-(5-thioxo-4,5-dihydro-1H-[1,2,4]triazol-3-ylmethyl)-tetrahydro-pyran-4-yl]-benzamide trifluoroacetate (6a)

Following a procedure analogous to that used in reaction (5a), {4-[4-(2-methyl-quinolin-4-ylmethoxy)-benzoylamino]-tetrahydro-pyran-4-yl}-acetic acid methyl ester (496 mg, 1.11 mmol; see WO01/70734 for preparation) was reacted with aqueous sodium hydroxide (3.3 mL, 1 N) overnight. After acidifying to pH ~4 with aqueous hydrochloric acid, ethyl acetate was added. The precipitate that formed in both layers was collected and dried to give the desired carboxylic acid (482 mg, 100%). MS found: $(M+H)^+=435$.

(6b)

Following a procedure analogous to that used in reaction (1c), the carboxylic acid (482 mg, 1.11 mmol) from reaction (6a) was reacted with thiosemicarbazide (101 mg, 1.11 mmol) for 2 h. The reaction was quenched with water and extracted with ethyl acetate. The precipitate that formed in the organic layer was collected to give the thiosemicarbazide amide (assumed quantitative recovery). MS found: $(M+H)^+=508$.

(6c)

Following a procedure analogous to that used in reaction (1d), the thiosemicarbazide amide (1.11 mmol) from reaction (6b) was heated at reflux with aqueous sodium hydroxide solution for 2 h. Purification of the crude material by reverse phase HPLC (15–55% acetonitrile/water) provided the desired triazolethione (80 mg, 12% for 3 steps). MS found: $(M+H)^+=490$.

Example 7

4-(2-Methyl-quinolin-4-ylmethoxy)-N-[1-(5-thioxo-4,5-dihydro-1H-[1,2,4]triazol-3-yl)-cyclopropylmethyl]-benzamide trifluoroacetate (7a)

Following a procedure analogous to that used in reaction (1c), 1-{[4-(2-methyl-quinolin-4-ylmethoxy)-benzoylamino]-methyl}-cyclopropanecarboxylic acid (184 mg, 0.47 mmol; see WO01/70734 for preparation) was reacted with thiosemicarbazide (43 mg, 0.47 mmol) overnight. The reaction was partitioned between ethyl acetate and water. The precipitate that formed in both layers was collected to give the thiosemicarbazide amide (assumed quantitative recovery). MS found: $(M+H)^+=464$.

(7b)

Following a procedure analogous to that used in reaction (1d), the thiosemicarbazide amide (0.47 mmol) from reaction (7a) was heated at reflux with aqueous sodium hydroxide solution for 1.5 h. Purification of the crude material by reverse phase HPLC (15–55% acetonitrile/water) provided the desired triazolethione (7 mg, 2% for 2 steps). MS found: $(M+H)^+=446$.

Example 8

5-{1-[4-(2-Methyl-quinolin-4-ylmethoxy)-benzenesulfonylmethyl]-cyclopentylmethyl}-2,4-dihydro-[1,2,4]triazole-3-thione trifluoroacetate (8a)

Following a procedure analogous to that used in reaction (1b), {1-[4-(2-methyl-quinolin-4-ylmethoxy)-benzenesulfonylmethyl]-cyclopentyl}-acetic acid methyl ester (400 mg, 0.86 mmol) was reacted with aqueous sodium hydroxide solution overnight to give the desired carboxylic acid (183 mg, 47%). MS found: $(M+H)^+=454$.

(8b)

Following a procedure analogous to that used in reaction (1c), the carboxylic acid (183 mg, 0.40 mmol) from reaction (8a) was reacted with thiosemicarbazide (40 mg, 0.44 mmol) overnight. The reaction was quenched with water and extracted with ethyl acetate. The organic layer was washed with water (3×), and brine, dried over magnesium sulfate, and concentrated to give the crude thiosemicarbazide amide (assumed quantitative recovery). MS found: $(M+H)^+=527$.

(8c)

Following a procedure analogous to that used in reaction (1d), the thiosemicarbazide amide (0.40 mmol) from reaction (8b) was heated at reflux with aqueous sodium hydroxide solution for 3 h. Purification of the crude material by reverse phase HPLC (20–60% acetonitrile/water) provided the desired triazolethione (85 mg, 42% for 2 steps). MS found: $(M+H)^+=509$.

Example 9

4-[4-(2-Isopropyl-benzoimidazol-1-ylmethyl)-benzoylamino]-4-(5-thioxo-4,5-dihydro-1H-[1,2,4]triazol-3-ylmethyl)-piperidine-1-carboxylic acid tert-butyl ester (9a)

Following a procedure analogous to that used in reaction (2a), 4-amino-4-methoxycarbonylmethyl-piperidine-1-carboxylic acid tert-butyl ester (223 mg, 0.82 mmol; see WO01/70734 for preparation) was reacted with 4-(2-isopropyl-benzoimidazol-1-ylmethyl)-benzoic acid (200 mg, 0.68 mmol; see U.S. patent application Ser. No. 10/244,626, filed Sep. 16, 2002) overnight. Purification of the crude material by silica gel chromatography (methylene chloride-10% methanol/methylene chloride) gave the desired amide (400 mg, >100%). MS found: $(M+H)^+=549$.

(9b)

Following a procedure analogous to that used in reaction (1b), the ester (0.68 mmol) from reaction (9a) was reacted with aqueous sodium hydroxide solution overnight. Solution was neutralized with aqueous hydrochloric acid and extracted with ethyl acetate (2×). The combined organic layers were concentrated and the remaining crude material purified by silica gel chromatography (0–5% methanol/methylene chloride) to give the desired carboxylic acid (171 mg, 47%). MS found: $(M+H)^+=535$.

(9c)

Following a procedure analogous to that used in reaction (1c), the carboxylic acid (170 mg, 0.32 mmol) from reaction (9b) was reacted with thiosemicarbazide (32 mg, 0.35 mmol) overnight. The reaction was quenched with water and extracted with ethyl acetate. The organic layer was washed with water, saturated sodium bicarbonate solution, and brine, dried over magnesium sulfate, and concentrated to give the crude thiosemicarbazide amide (164 mg, 84%).

(9d)

Following a procedure analogous to that used in reaction (1d), the thiosemicarbazide amide (160 mg, 0.26 mmol) from reaction (9c) was heated at reflux with aqueous sodium hydroxide solution for 2 h. Purification of the crude material by silica gel chromatography (0–10% methanol/methylene chloride) provided the desired triazolethione (46 mg, 30%). MS found: $(M+H)^+=590$.

Example 10

4-(2-Methyl-quinolin-4-ylmethoxy)-N-[cis 2-(5-thioxo-4,5-dihydro-1H-[1,2,4]triazol-3-yl)-cyclopentyl]-benzamide (10a)

Following a procedure analogous to that used in reaction (3a), cis 2-amino-cyclopentanecarboxylic acid ethyl ester hydrochloride (120 mg, 0.62 mmol) was reacted with 4-(2-methyl-quinolin-4-ylmethoxy)-benzoic acid (182 mg, 0.62 mmol) for 1 h. Purification of the crude material by silica gel chromatography (4% methanol/methylene chloride) furnished the desired amide (250 mg, 93%). MS found: $(M+H)^+=433$.

(10b)

Following a procedure analogous to that used in reaction (1b), the ester (245 mg, 0.57 mmol) from reaction (10a) was reacted with aqueous sodium hydroxide solution for 6 h to give the carboxylic acid (215 mg, 94%). MS found: $(M+H)^+=405$.

(10c)

Following a procedure analogous to that used in reaction (2c), the carboxylic acid (215 mg, 0.53 mmol) from reaction (10b) was reacted with thiosemicarbazide (54 mg, 0.58 mmol) for 1 h to give the crude thiosemicarbazide amide (200 mg, 79%). MS found: $(M+H)^+=478$.

(10d)

Following a procedure analogous to that used in reaction (1d), the thiosemicarbazide amide (100 mg, 0.21 mmol)

from reaction (10c) was heated at reflux with aqueous sodium hydroxide solution for 1 h to provide the desired triazolethione (60 mg, 62%). MS found: (M+H)$^+$=460.

Example 11

4-(2-Isopropyl-benzoimidazol-1-ylmethyl)-N-[2-(5-thioxo-4,5-dihydro-1H-[1,2,4]triazol-3-yl)-cyclopentyl]-benzamide (11a)
Following a procedure analogous to that used in reaction (2a), cis 2-amino-cyclopentanecarboxylic acid ethyl ester hydrochloride (100 mg, 0.52 mmol) was reacted with 4-(2-isopropyl-benzoimidazol-1-ylmethyl)-benzoic acid (137 mg, 0.47 mmol) overnight. Purification of the crude material by silica gel chromatography (0–5% methanol/methylene chloride) furnished the desired amide (157 mg, 78%). MS found: (M+H)$^+$=434.

(11b)
Following a procedure analogous to that used in reaction (1b), the ester (155 mg, 0.36 mmol) from reaction (11a) was reacted with aqueous sodium hydroxide solution for 30 min. Purification of the crude acid by silica gel chromatography (0-5% methanol/methylene chloride) gave the carboxylic acid (114 mg, 79%). MS found: (M+H)$^+$=406.

(11c)
Following a procedure analogous to that used in reaction (1c), the carboxylic acid (114 mg, 0.28 mmol) from reaction (11b) was reacted with thiosemicarbazide (28 mg, 0.31 mmol) for 48 h to give the crude thiosemicarbazide amide (150 mg, >100%). MS found: (M+H)$^+$=479.

(11d)
Following a procedure analogous to that used in reaction (1d), the thiosemicarbazide amide (0.28 mmol) from reaction (11c) was heated at reflux with aqueous sodium hydroxide solution for 1.5 h. Purification of the crude material by silica gel chromatography (0–5% methanol/methylene chloride) provided the desired triazolethione as a 4:1 mixture of cis:trans diastereomers (18 mg, 14% for two steps). MS found: (M+H)$^+$=461.

Example 12

4-(2-Methyl-quinolin-4-ylmethyl)-N-[2-(5-thioxo-4,5-dihydro-1H-[1,2,4]triazol-3-yl)-cyclopentyl]-benzamide trifluoroacetate (12a)
Following a procedure analogous to that used in reaction (2a), cis 2-amino-cyclopentanecarboxylic acid methyl ester hydrochloride (240 mg, 1.34 mmol) was reacted with 4-(2-methyl-quinolin-4-ylmethyl)-benzoic acid (370 mg, 1.34 mmol) overnight. Purification of the crude material by silica gel chromatography (70% ethyl acetate/hexanes-100% ethyl acetate) furnished the desired amide (218 mg, 40%). MS found: (M+H)$^+$=403.

(12b)
Following a procedure analogous to that used in reaction (1b), the ester (218 mg, 0.54 mmol) from reaction (12a) was reacted with aqueous sodium hydroxide solution for 2 h. The solution was neutralized with aqueous hydrochloric acid and concentrated to dryness to provide the crude carboxylic acid (assumed 100% recovery). MS found: (M+H)$^+$=389.

(12c)
Following a procedure analogous to that used in reaction (1c), the carboxylic acid (0.54 mmol) from reaction (12b) was reacted with thiosemicarbazide (49 mg, 0.54 mmol) for 3 h to give the crude thiosemicarbazide amide (assumed 100% recovery). MS found: (M+H)$^+$=462.

(12d)
Following a procedure analogous to that used in reaction (1d), the thiosemicarbazide amide (0.54 mmol) from reaction (12c) was heated at reflux with aqueous sodium hydroxide solution for 3 h. Purification of the crude material by reverse phase HPLC (15–55% acetonitrile/water) provided the desired triazolethione as a 5:1 mixture of cis:trans diastereomers (28 mg, 9% for three steps). MS found: (M+H)$^+$=444.

Example 13

4-(2-Methyl-quinolin-4-ylmethoxy)-N-[2-(5-thioxo-4,5-dihydro-1H-[1,2,4]triazol-3-yl)-cyclopentyl]-benzenesulfonamide trifluoroacetate (13a)
Following a procedure analogous to that used in reaction (1a), cis 2-amino-cyclopentanecarboxylic acid ethyl ester hydrochloride (47 mg, 0.24 mmol) was reacted with 4-(2-methyl-quinolin-4-ylmethoxy)-benzenesulfonyl chloride (83 mg, 0.24 mmol) to give the sulfonamide (80 mg, 71%). (M−H)$^-$=467.

(13b)
Following a procedure analogous to that used in reaction (1b), the ester (70 mg, 0.15 mmol) from reaction (13a) was reacted with aqueous sodium hydroxide solution overnight. The solution was cooled to 0° C. and neutralized with aqueous hydrochloric acid. Ethyl acetate was added and the precipitate that formed was collected and dried to provide the crude carboxylic acid (77 mg, >100%). MS found: (M+H)$^+$=441.

(13c)
Following a procedure analogous to that used in reaction (1c), the carboxylic acid (0.15 mmol) from reaction (13b) was reacted with thiosemicarbazide (18 mg, 0.19 mmol) for 2 h to give the crude thiosemicarbazide amide (45 mg, 58%). MS found: (M+H)$^+$=514.

(13d)
Following a procedure analogous to that used in reaction (1d), the thiosemicarbazide amide (40 mg, 0.078 mmol) from reaction (13c) was heated at reflux with aqueous sodium hydroxide solution for 2 h. Purification of the crude material by reverse phase HPLC (15–55% acetonitrile/water) provided the desired triazolethione (6 mg, 16%). MS found: (M+H)$^+$=496.

Example 14

(3S,4R)-4-(2-Methyl-quinolin-4-ylmethoxy)-N-[3-(5-thioxo-4,5-dihydro-1H-[1,2,4]triazol-3-yl)-tetrahydro-pyran-4-yl]-benzamide (14a)
Following a procedure analogous to that used in reaction (1b), (3R, 4R)-4-[4-(2-methyl-quinolin-4-ylmethoxy)-benzoylamino]-tetrahydro-pyran-3-carboxylic acid methyl ester (186 mg, 0.43 mmol; see WO01/70673 for preparation) was reacted with aqueous sodium hydroxide solution for 2 h to provide the carboxylic acid (117 mg, 65%). MS found: (M+H)$^+$=421.

(14b)

Following a procedure analogous to that used in reaction (1c), the carboxylic acid (112 mg, 0.27 mmol) from reaction (14a) was reacted with thiosemicarbazide (27 mg, 0.29 mmol) for 1 h. Purification of the crude material by reverse phase HPLC (10–100% acetonitrile/water) gave the desired thiosemicarbazide amide (108 mg, 67%). MS found: (M+H)$^+$=494.

(14c)

Following a procedure analogous to that used in reaction (1d), the thiosemicarbazide amide (65 mg, 0.11 mmol) from reaction (14b) was heated at reflux with aqueous sodium hydroxide solution for 1 h to provide the desired triazolethione (50 mg, 98%). MS found: (M+H)$^+$=476.

Example 15

Trans-4-(2-methyl-quinolin-4-ylmethoxy)-N-[3-(5-thioxo-4,5-dihydro-1H-[1,2,4]triazol-3-yl)-tetrahydro-pyran-4-yl]-benzamide trifluoroacetate (15a)

A solution of cis-4-[4-(2-methyl-quinolin-4-ylmethoxy)-benzoylamino]-tetrahydro-pyran-3-carboxylic acid methyl ester (514 mg, 1.18 mmol; see WO01/70673 for preparation) and 1,8-diazabicyclo[5.4.0]undec-7-ene (1.8 g, 11.8 mmol) in toluene (10 mL) was heated at reflux for 4 h. After cooling to rt, the solution was concentrated. The remaining residue was filtered through a pad of silica gel using ethyl acetate as the eluent to give the desired material as a 9:1 mixture of trans:cis diastereomers (498 mg, 97%).

(15b)

Following a procedure analogous to that used in reaction (1b), the ester (498 mg, 1.15 mmol) from reaction (15a) was treated with aqueous sodium hydroxide solution to provide the carboxylic acid (245 mg, 51%; trans:cis=9:1). MS found: (M+H)$^+$=421.

(15c)

Following a procedure analogous to that used in reaction (1c), the carboxylic acid (235 mg, 0.56 mmol) from reaction (15b) was reacted with thiosemicarbazide (51 mg, 0.56 mmol) overnight. The reaction was partitioned between ethyl acetate and water. The precipitate that formed in both layers was collected to give the thiosemicarbazide amide (assumed quantitative recovery). MS found: (M+H)$^+$=494.

(15d)

Following a procedure analogous to that used in reaction (1d), the thiosemicarbazide amide (0.56 mmol) from reaction (15c) was heated at reflux with aqueous sodium hydroxide solution for 1 h. Purification of the crude material by reverse phase HPLC (5–55% acetonitrile/water) provided the desired triazolethione (43 mg, 13%; trans:cis=9:1). MS found: (M+H)$^+$=476.

Example 16

(5R,7R,8S)-4-(2-Methyl-quinolin-4-ylmethoxy)-N-[8-(5-thioxo-4,5-dihydro-1H-[1,2,4]triazol-3-yl)-1-oxa-spiro[4.4]non-7-yl]-benzamide (16a)

Following a procedure analogous to that used in reaction (1b), (5R,7R,8S)-8-[4-(2-methyl-quinolin-4-ylmethoxy)-benzoylamino]-1-oxa-spiro[4.4]nonane-7-carboxylic acid methyl ester (640 mg, 1.35 mmol) was reacted with aqueous sodium hydroxide solution overnight to furnish the carboxylic acid (350 mg, 56%). MS found: (M+H)$^+$=461.

(16b)

Following a procedure analogous to that used in reaction (1c), the carboxylic acid (300 mg, 0.65 mmol) from reaction (16a) was reacted with thiosemicarbazide (65 mg, 0.72 mmol) overnight. Purification of the crude material by silica gel chromatography (0–10% methanol/methylene chloride) gave the thiosemicarbazide amide (200 mg, 58%). MS found: (M+H)$^+$=534.

(16c)

Following a procedure analogous to that used in reaction (1d), the thiosemicarbazide amide (200 mg, 0.38 mmol) from reaction (16b) was heated at reflux with aqueous sodium hydroxide solution for 1.5 h. The solid that was obtained was recrystallized from methanol/methylene chloride/hexanes mixture to provide the desired triazolethione (110 mg, 57%). MS found: (M+H)$^+$=516.

Example 19

3-[4-(2-Methyl-quinolin-4-ylmethoxy)-benzoylamino]-4-(5-thioxo-4,5-dihydro-1H-[1,2,4]triazol-3-yl)-pyrrolidine-1-carboxylic acid tert-butyl ester trifluoroacetate (19a)

Following a procedure analogous to that used in reaction (1b), (3S,4S)-4-[4-(2-methyl-quinolin-4-ylmethoxy)-benzoylamino]-pyrrolidine-1,3-dicarboxylic acid 1-tert-butyl ester 3-methyl ester (1.16 g, 2.23 mmol) was reacted with aqueous lithium hydroxide solution (5 mL, 1 M) for 1 h. The solution was neutralized with aqueous hydrochloric acid and extracted with ethyl acetate. The organic layer was dried over magnesium sulfate and concentrated to give the carboxylic acid as a 2:1 mixture of cis:trans isomers (1.0 g, 91%). MS found: (M+H)$^+$=506.

(19b)

Following a procedure analogous to that used in reaction (1c), the acid (200 mg, 0.396 mmol) from reaction (19a) was reacted with thiosemicarbazide (40 mg, 0.435 mmol) for 1 h. Purification of the crude material by reverse phase HPLC (10–100% acetonitrile/water) furnished the desired compound (150 mg, 55%; 2:1 cis:trans). MS found: (M+H)$^+$=579.

(19c)

Following a procedure analogous to that used in reaction (1d), the thiosemicarbazide amide (50 mg, 0.072 mmol) from reaction (19b) was heated at reflux with aqueous sodium hydroxide solution for 30 min. Purification of the material by reverse phase HPLC (10–100% acetonitrile/water) gave the desired triazolethione as a 2:1 mixture of cis:trans isomers (30 mg, 63%). MS found: (M+H)$^+$=561.

Example 20

4-(2-Methyl-quinolin-4-ylmethoxy)-N-[4-(5-thioxo-4,5-dihydro-1H-[1,2,4]triazol-3-yl)-pyrrolidin-3-yl]-benzamide trifluoroacetate (20a)

To a solution of the triazolethione (20 mg, 0.03 mmol) from reaction (19c) in methylene chloride (2 mL) was added trifluoroacetic acid (2 mL). The mixture was stirred for 1 h and then concentrated under reduced pressure. Lyophilization of the material provided the desired product as a 2:1 mixture of cis:trans isomers (8 mg, 40%). MS found: $(M+H)^+=461$.

Example 21

3-[4-(1,1-Dioxo-2,3-dihydro-1H-1$\lambda^6$-benzo[1,4]thiazin-4-ylmethyl)-benzoylamino]-4-(5-thioxo-4,5-dihydro-1H-[1,2,4]triazol-3-yl)-pyrrolidine-1-carboxylic acid tert-butyl ester trifluoroacetate (21a)

Following a procedure analogous to that used in reaction (2a), (3S,4S)-4-amino-pyrrolidine-1,3-dicarboxylic acid 1-tert-butyl ester 3-methyl ester (288 mg, 1.18 mmol) was reacted with 4-(1,1-dioxo-2,3-dihydro-1H-1□$^6$-benzo[1,4]thiazin-4-ylmethyl)-benzoic acid (374 mg, 1.18 mmol) overnight. Purification of the crude material by silica gel chromatography (60–85% ethyl acetate/hexanes) gave the desired compound (319 mg, 49%).

(21b)

To a solution of the ester (319 mg, 0.59 mmol) from reaction (21a) in tetrahydrofuran (3 mL) at 0° C. was added aqueous sodium hydroxide solution (1.76 mL, 1 N). After stirring for 1 h at 0° C., the solution was allowed to warm to rt and stir for an additional hour. The solution was acidified to pH~4 with aqueous hydrochloric acid. The precipitate that forms was collected and dried to provide the carboxylic acid (216 mg, 69%). MS found: $(M+Na)^+=552$.

(21c)

Following a procedure analogous to that used in reaction (1c), the acid (208 mg, 0.39 mmol) from reaction (21b) was reacted with thiosemicarbazide (39 mg, 0.43 mmol) for 4 h. The reaction was partitioned between ethyl acetate/water and the layers separated. A precipitate began to form in the organic layer. The organic layer was concentrated to give the thiosemicarbazide amide (assumed quantitative recovery). MS found: $(M+H)^+=603$.

(21d)

Following a procedure analogous to that used in reaction (1d), the thiosemicarbazide amide (0.39 mmol) from reaction (21c) was heated at reflux with aqueous sodium hydroxide solution for 2 h. The solution was acidified to pH~5–6 with aqueous hydrochloric acid and extracted with ethyl acetate. The organic layer was washed with brine and concentrated. Purification of the crude material by reverse phase HPLC (15–55% acetonitrile/water) furnished the desired triazolethione as a 5:1 mixture of cis:trans isomers (111 mg, 40%). MS found: $(M+H)^+=585$.

Example 22

4-(1,1-Dioxo-2,3-dihydro-1H-1$\lambda^6$-benzo[1,4]thiazin-4-ylmethyl)-N-[4-(5-thioxo-4,5-dihydro-1H-[1,2,4]triazol-3-yl)-pyrrolidin-3-yl]-benzamide trifluoroacetate (22a)

Following a procedure analogous to that used in reaction (20a), the triazolethione (54 mg, 0.077 mmol) from reaction (21d) was reacted wit trifluoroacetic acid for 1 h. Purification of the crude material by reverse phase HPLC (15–55% acetonitrile/water) gave the desired compound as a 10:1 mixture of cis:trans isomers (33 mg, 61%). MS found: $(M+H)^+=485$.

Example 23

(3S,4S)-4-(2-Methyl-quinolin-4-ylmethoxy)-N-[4-(5-thioxo-4,5-dihydro-1H-[1,2,4]triazol-3-yl)-pyrrolidin-3-yl]-benzamide trifluoroacetate (23a)

Following a procedure analogous to that used in reaction (21b), (3S,4S)-4-[4-(2-methyl-quinolin-4-ylmethoxy)-benzoylamino]-pyrrolidine-1,3-dicarboxylic acid 1-tert-butyl ester 3-methyl ester (864 mg, 1.66 mmol) was reacted with aqueous sodium hydroxide solution (5 mL, 1 N). After adjusting the pH to 6, the organic solvent was removed under reduced pressure. The precipitate that formed was collected by filtration to give the carboxylic acid as a single isomer (470 mg, 56%). MS found: $(M+H)^+=506$.

(23b)

Following a procedure analogous to that used in reaction (1c), the acid (280 mg, 0.554 mmol) from reaction (23a) was reacted with thiosemicarbazide (56 mg, 0.61 mmol) for 1 h. The reaction was quenched with water and extracted with ethyl acetate (100 mL). A solid precipitated from the organic layer and was collected to give the thiosemicarbazide amide (290 mg, 91%). MS found: $(M+H)^+=579$.

(23c)

Following a procedure analogous to that used in reaction (1d), the thiosemicarbazide amide (110 mg, 0.19 mmol) from reaction (23b) was heated at reflux with aqueous sodium hydroxide solution for 1 h to provide the Boc-triazolethione as a single isomer (67 mg, 63%). MS found: $(M+H)^+=561$.

(23d)

Following a procedure analogous to that used in reaction (20a), the triazolethione (60 mg, 0.107 mmol) from reaction (23c) was reacted with trifluoroacetic acid for 1 h. Purification of the crude material by reverse phase HPLC (5–55% acetonitrile/water) furnished the desired triazolethione as a single isomer (22 mg, 30%). MS found: $(M+H)^+=461$.

Example 24

(3S,4S)-N-[1-Acetyl-4-(5-thioxo-4,5-dihydro-1H-[1,2,4]triazol-3-yl)-pyrrolidin-3-yl]-4-(2-methyl-quinolin-4-ylmethoxy)-benzamide trifluoroacetate (24a)

To a solution of the Boc-pyrrolidine trifluoroacetate (50 mg, 0.089 mmol) from reaction (23c) in methanol (2 mL)

was added 4 N hydrochloric acid in dioxane (1 mL, 4 N). After stirring for 2 h at rt, the solution was concentrated under reduced pressure to give the pyrrolidine as a hydrochloride salt (assumed quantitative recovery). MS found: $(M+H)^+=461$.

(24b)
Following a procedure analogous to that used in reaction (3a), the pyrrolidine (0.089 mmol) from reaction (24a) was reacted with acetic acid (5.3 mg, 0.089 mmol) for 1 h. The reaction was quenched with ice water and filtered. Purification of the crude material by reverse phase HPLC (10–100% acetonitrile/water) provided the desired acetyl compound (12 mg, 24%). MS found: $(M+H)^+=503$.

Example 25

(3S,4S)-4-(2-Methyl-quinolin-4-ylmethoxy)-N-[1-propyl-4-(5-thioxo-4,5-dihydro-1H-[1,2,4]triazol-3-yl)-pyrrolidin-3-yl]-benzamide trifluoroacetate (25a)
Following a procedure analogous to that used in reaction (20a), (3S,4S)-4-[4-(2-methyl-quinolin-4-ylmethoxy)-benzoylamino]-pyrrolidine-1,3-dicarboxylic acid 1-tert-butyl ester 3-methyl ester (484 mg, 0.93 mmol) was reacted with trifluoroacetic acid for 1 h. Purification of the crude material by reverse phase HPLC (10–100% acetonitrile/water) gave the desired compound (450 mg, 75%). MS found: $(M+H)^+=420$.

(25b)
To a solution of the pyrrolidine (150 mg, 0.23 mmol) from reaction (25a), propionaldehyde (16 mg, 0.28 mmol), and triethylamine (94 mg, 0.93 mmol) in methylene chloride (3 mL) was added sodium triacetoxyborohydride (147 mg, 0.69 mmol). After stirring for 2 h, the reaction was quenched with water and extracted with ethyl acetate (20 mL×2). The combined organic layers were washed with brine (10 mL), dried over magnesium sulfate, and concentrated. Purification of the crude material by silica gel chromatography (4% methanol/methylene chloride) provided the N-propyl derivative (57 mg, 53%). MS found: $(M+H)^+=462$.

(25c)
Following a procedure analogous to that used in reaction (1b), the methyl ester (57 mg, 0.12 mmol) from reaction (25b) was treated with aqueous sodium hydroxide solution for 1 h at 0° C. The solution was neutralized with aqueous hydrochloric acid and concentrated under reduced pressure to give the carboxylic acid (assumed quantitative recovery). MS found: $(M+H)^+=448$.

(25d)
Following a procedure analogous to that used in reaction (1c), the acid (0.12 mmol) from reaction (25c) was reacted with thiosemicarbazide (12 mg, 0.136 mmol) for 1 h. The reaction was quenched with water and filtered. Purification of the crude material by reverse phase HPLC (10–100% acetonitrile/water) provided the desired thiosemicarbazide amide (17 mg, 18%). MS found: $(M+H)^+=521$.

(25e)
Following a procedure analogous to that used in reaction (1d), the thiosemicarbazide amide (17 mg, 0.023 mmol) from reaction (25d) was heated at reflux with aqueous sodium hydroxide solution for 1 h. The reaction was neutralized with aqueous hydrochloric acid at 0° C. and diluted with methanol. Purification of the crude material by reverse phase HPLC (10–100% acetonitrile/water) furnished the desired triazolethione (8.4 mg, 53%). MS found: $(M+H)^+=503$.

Example 26

Trans-4-(2-Methyl-quinolin-4-ylmethoxy)-N-[4-(5-thioxo-4,5-dihydro-1H-[1,2,4]triazol-3-yl)-pyrrolidin-3-yl]-benzamide trifluoroacetate (26a)
Following a procedure analogous to that used in reaction (1b), trans-4-[4-(2-methyl-quinolin-4-ylmethoxy)-benzoylamino]-pyrrolidine-1,3-dicarboxylic acid 1-tert-butyl ester 3-ethyl ester (200 mg, 0.375 mmol) was treated with aqueous sodium hydroxide solution for 1 h to give the carboxylic acid (163 mg, 86%). MS found: $(M+H)^+=506$.

(26b)
Following a procedure analogous to that used in reaction (1c), the acid (163 mg, 0.32 mmol) from reaction (26a) was reacted with thiosemicarbazide (32 mg, 0.35 mmol) for 1 h. The reaction was quenched with water and filtered. Purification of the crude material by reverse phase HPLC (10–100% acetonitrile/water) provided the thiosemicarbazide amide (80 mg, 43%). MS found: $(M+H)^+=579$.

(26c)
Following a procedure analogous to that used in reaction (1d), the thiosemicarbazide amide (80 mg, 0.14 mmol) from reaction (26b) was heated at reflux with aqueous sodium hydroxide solution for 1 h. The reaction was neutralized with aqueous hydrochloric acid and diluted with methanol. Purification of the crude material by reverse phase HPLC (10–100% acetonitrile/water) furnished the desired triazolethione as a 3:2 mixture of trans:cis isomers (30 mg, 38%). MS found: $(M+H)^+=561$.

(26d)
Following a procedure analogous to that used in reaction (20a), the Boc-pyrrolidine (25 mg, 0.037 mmol) from reaction (26c) was reacted with trifluoroacetic acid for 2 h. Purification of the crude material by reverse phase HPLC (10–100% acetonitrile/water) provided the desired compound as a single isomer (14 mg, 54%). MS found: $(M+H)^+=461$.

Example 27

(3S,4S)-3-[4-(2-Methyl-quinolin-4-ylmethoxy)-benzoylamino]-4-(5-thioxo-4,5-dihydro-1H-[1,2,4]triazol-3-yl)-piperidine-1-carboxylic acid tert-butyl ester (27a)
Following a procedure analogous to that used in reaction (1b), (3S,4S)-3-[4-(2-methyl-quinolin-4-ylmethoxy)-benzoylamino]-piperidine-1,4-dicarboxylic acid 1-tert-butyl ester 4-methyl ester (1.0 g, 1.88 mmol) was reacted with aqueous sodium hydroxide solution for 2 h to give the desired carboxylic acid (1.2 g, >100%). MS found: $(M+H)^+=520$.

(27b)
Following a procedure analogous to that used in reaction (1c), the acid (300 mg, 0.58 mmol) from reaction (27a) was reacted with thiosemicarbazide (58 mg, 0.64 mmol) overnight. Purification of the crude material by silica gel chromatography (0–5% methanol/methylene chloride) provided the thiosemicarbazide amide (135 mg, 39%). MS found: $(M+H)^+=593$.

(27c)
Following a procedure analogous to that used in reaction (1d), the thiosemicarbazide amide (135 mg, 0.23 mmol) from reaction (27b) was heated at reflux with aqueous sodium hydroxide solution for 1 h. Solution was cooled to 0° C. and neutralized with aqueous hydrochloric acid. The precipitate that formed was collected. Purification of the crude material by silica gel chromatography (5–10% methanol/methylene chloride) gave the triazolethione (40 mg, 26%). MS found: $(M+H)^+=575$.

Example 28

(3S,4S)-4-(2-Methyl-quinolin-4-ylmethoxy)-N-[4-(5-thioxo-4,5-dihydro-1H-[1,2,4]triazol-3-yl)-piperidin-3-yl]-benzamide trifluoroacetate (28a)
Following a procedure analogous to that used in reaction (20a), the Boc-piperidine (20 mg, 0.029 mmol) from reaction (27c) was treated with trifluoroacetic acid for 1 h to provide the desired product (18 mg, 86%). MS found: $(M+H)^+=475$.

Example 29

(3S,4S)-N-[1-Acetyl-4-(5-thioxo-4,5-dihydro-1H-[1,2,4]triazol-3-yl)-piperidin-3-yl]-4-(2-methyl-quinolin-4-ylmethoxy)-benzamide trifluoroacetate (29a)
To a solution of the piperidine (58 mg, 0.083 mmol) from reaction (28a) and triethylamine (33 mg, 0.33 mmol) in methylene chloride (2 mL) was added acetic anhydride (8.4 mg, 0.083 mmol). The reaction was allowed to stir overnight and then was concentrated. Purification of the crude material (2×) by reverse phase HPLC (10–100% acetonitrile/water) gave the desired acetyl compound (8 mg, 15%). MS found: $(M+H)^+=517$.

Example 30

(3S,4S)-4-(2-Methyl-quinolin-4-ylmethoxy)-N-[1-propyl-4-(5-thioxo-4,5-dihydro-1H-[1,2,4]triazol-3-yl)-piperidin-3-yl]-benzamide trifluoroacetate (30a)
Following a procedure analogous to that used in reaction (20a), (3S,4S)-3-[4-(2-methyl-quinolin-4-ylmethoxy)-benzoylamino]-piperidine-1,4-dicarboxylic acid 1-tert-butyl ester 4-ethyl ester (1.0 g, 1.83 mmol) was reacted with trifluoroacetic acid for 1 h to give the desired piperidine (1.4 g, >100%). MS found: $(M+H)^+=448$.

(30b)
Following a procedure analogous to that used in reaction (25b), the piperidine (300 mg, 0.44 mmol) from reaction (30a) was reacted with propionaldehyde (31 mg, 0.53 mmol) for 3 h. Purification of the crude material by silica gel chromatography (0–15% methanol/methylene chloride) provided the alkylated piperidine (258 mg, >100%). MS found: $(M+H)^+=490$.

(30c)
Following a procedure analogous to that used in reaction (1b), the ester (0.44 mmol) from reaction (30b) was reacted with aqueous sodium hydroxide solution for 2.5 h. The solution was acidified to pH ~4–5 with aqueous hydrochloric acid and extracted with ethyl acetate. The organic layers were concentrated to furnish the crude carboxylic acid (250 mg, >100%). MS found: $(M+H)^+=462$.

(30d)
Following a procedure analogous to that used in reaction (1c), the acid (0.44 mmol) from reaction (30c) was reacted with thiosemicarbazide (44 mg, 0.48 mmol) overnight to provide the thiosemicarbazide amide (assumed quantitative recovery). $(M-H)^-=533$.

(30e)
Following a procedure analogous to that used in reaction (1d), the thiosemicarbazide amide (0.44 mmol) from reaction (30d) was heated at reflux with aqueous sodium hydroxide solution for 3 h. Purification of the crude solid by reverse phase HPLC (10–100% acetonitrile/water) gave the desired triazolethione (145 mg, 44%). MS found: $(M+H)^+=517$.

Example 31

(3S,4S)-N-[1-Methanesulfonyl-4-(5-thioxo-4,5-dihydro-1H-[1,2,4]triazol-3-yl)-piperidin-3-yl]-4-(2-methyl-quinolin-4-ylmethoxy)-benzamide trifluoroacetate (31a)
To a solution of the piperidine (300 mg, 0.44 mmol) from reaction (30a) and triethylamine (180 mg, 1.78 mmol) in methylene chloride (10 mL) was added methanesulfonyl chloride (61 mg, 0.53 mmol). After 1 h at rt, the reaction was partitioned between ethyl acetate/water. The layers were separated and the organic layer washed with saturated sodium bicarbonate solution and brine, dried over magnesium sulfate, and concentrated to give the desired compound (200 mg, 86%). MS found: $(M+H)^+=526$.

(31b)
Following a procedure analogous to that used in reaction (1b), the ester (200 mg, 0.38 mmol) from reaction (31a) was reacted with sodium hydroxide solution overnight to provide the desired carboxylic acid (155 mg, 76%). MS found: $(M+H)^+=498$.

(31c)
Following a procedure analogous to that used in reaction (1c), the acid (150 mg, 0.28 mmol) from reaction (31b) was reacted with thiosemicarbazide (28 mg, 0.31 mmol) overnight. The crude thiosemicarbazide amide (200 mg, >100%) that was recovered was taken into the next reaction without further purification. MS found: $(M+H)^+=571$.

(31d)
Following a procedure analogous to that used in reaction (1d), the thiosemicarbazide amide (0.28 mmol) from reaction (31c) was heated at reflux with aqueous sodium hydroxide solution for 3 h. The reaction was acidified to pH ~4 with aqueous hydrochloric acid and extracted with ethyl acetate. The organic layer was concentrated and the remaining residue purified by reverse phase HPLC (10–100% acetonitrile/water) to furnish the desired triazolethione (12 mg, 6% for two steps). MS found: $(M+H)^+=553$.

Example 32

(3S,4S)-N-[1-Isopropyl-4-(5-thioxo-4,5-dihydro-1H-[1,2,4]triazol-3-yl)-piperidin-3-yl]-4-(2-methyl-quinolin-4-ylmethoxy)-benzamide trifluoroacetate (32a)
Following a procedure analogous to that used in reaction (25b), the piperidine (380 mg, 0.562 mmol) from reaction (30a) was reacted with acetone (979 mg, 16.9 mmol) overnight. The reaction was quenched with aqueous sodium hydroxide solution (1 N). The layers were separated and the organic layer washed with brine, dried, and concentrated. Purification of the crude material by silica gel chromatography (0–10% methanol/methylene chloride) gave the desired compound (161 mg, 59%). MS found: $(M+H)^+=490$.

(32b)
Following a procedure analogous to that used in reaction (1b), the ester (161 mg, 0.33 mmol) from reaction (32a) was reacted with aqueous sodium hydroxide solution for 2 h. The reaction was neutralized with aqueous saturated potassium dihydrogenphosphate solution. The mixture was lyophilized and the remaining material used in the next reaction without further purification (assumed quantitative recovery). MS found: $(M+H)^+=462$.

(32c)
Following a procedure analogous to that used in reaction (1c), the acid (0.33 mmol) from reaction (32b) was reacted with thiosemicarbazide (30 mg, 0.33 mmol) for 1 h to give the thiosemicarbazide amide (assumed quantitative recovery). MS found: $(M+H)^+=535$.

(32d)
Following a procedure analogous to that used in reaction (1d), the thiosemicarbazide amide (0.33 mmol) from reaction (32c) was heated at reflux with aqueous sodium hydroxide solution for 45 min. Purification of the crude material by reverse phase HPLC (5–55% acetonitrile/water) provided the desired triazolethione (79 mg, 32% for three steps). MS found: $(M+H)^+=517$.

Example 33

(3S,4S)-4-(2-Methyl-quinolin-4-ylmethoxy)-N-[1-methyl-4-(5-thioxo-4,5-dihydro-1H-[1,2,4]triazol-3-yl)-piperidin-3-yl]-benzamide (33a)
Following a procedure analogous to that used in reaction (25b), the piperidine (300 mg, 0.44 mmol) from reaction (30a) was reacted with formaldehyde (43 mg, 0.53 mmol, 37% in water) for 3 h. Purification of the crude material by silica gel chromatography (0–15% methanol/methylene chloride) provided the methylated piperidine (230 mg, >100%). MS found: $(M+H)^+=462$.

(33b)
Following a procedure analogous to that used in reaction (1b), the ester (0.44 mmol) from reaction (33a) was reacted with aqueous sodium hydroxide solution for 2 h. The solution was acidified to pH ~4–5 with aqueous hydrochloric acid and concentrated. The mixture was diluted with methanol and filtered to remove any inorganic salts. The methanol layer was concentrated to give the carboxylic acid (250 mg, >100%). MS found: $(M+H)^+=434$.

(33c)
Following a procedure analogous to that used in reaction (1c), the acid (0.44 mmol) from reaction (33b) was reacted with thiosemicarbazide (45 mg, 0.49 mmol) overnight. Upon addition of ethyl acetate, a precipitate formed. The solid was collected by filtration to provide the thiosemicarbazide amide (298 mg, >100%). MS found: $(M+H)^+=507$.

(33d)
Following a procedure analogous to that used in reaction (1d), the thiosemicarbazide amide (0.44 mmol) from reaction (33c) was heated at reflux with aqueous sodium hydroxide solution for 2 h. The reaction was acidified to pH ~4 with aqueous hydrochloric acid. The precipitate that formed was collected and re-crystallized from methanol to provide the desired triazolethione (48 mg, 22% for three steps). MS found: $(M+H)^+=489$.

Example 34

(3S,4R)-4-(2-Methyl-quinolin-4-ylmethoxy)-N-[3-(5-thioxo-4,5-dihydro-1H-[1,2,4]triazol-3-yl)-piperidin-4-yl]-benzamide trifluoroacetate (34a)
Following a procedure analogous to that used in reaction (1b), (3S,4R)-4-[4-(2-methyl-quinolin-4-ylmethoxy)-benzoylamino]-piperidine-1,3-dicarboxylic acid 1-tert-butyl ester 3-methyl ester (84 mg, 0.16 mmol) was reacted with aqueous sodium hydroxide solution overnight. The reaction was acidified to pH ~4–5 with aqueous hydrochloric acid and extracted with ethyl acetate. The organic layer was washed with brine, dried, and concentrated to provide the carboxylic acid (assumed quantitative recovery). MS found: $(M+H)^+=520$.

(34b)
Following a procedure analogous to that used in reaction (1c), the acid (0.16 mmol) from reaction (34a) was reacted with thiosemicarbazide (14 mg, 0.16 mmol) for 2 h. The crude product was used in the next reaction without further purification (assumed quantitative recovery). MS found: $(M+H)^+=593$.

(34c)
Following a procedure analogous to that used in reaction (1d), the thiosemicarbazide amide (0.16 mmol) from reaction (34b) was heated at reflux with aqueous sodium hydroxide solution for 3 h. Purification of the crude material by reverse phase HPLC (5–55% acetonitrile/water) furnished the de-Boc triazolethione (15 mg, 14% for three steps). MS found: $(M+H)^+=475$.

Example 35

4-(2-Methyl-quinolin-4-ylmethoxy)-N-[2-(5-oxo-4,5-dihydro-1H-[1,2,4]triazol-3-yl)-cyclopentyl]-benzamide trifluoroacetate (35a)
Following a procedure analogous to that used in reaction (1c), the acid (268 mg, 0.66 mmol) from reaction (10b) was reacted with semicarbazide hydrochloride (111 mg, 1.0 mmol) overnight. The reaction was diluted with ethyl acetate and washed with saturated potassium dihydrogenphosphate and brine. The organic layer was dried and concentrated to give the desired semicarbazide amide (78 mg, 26%). MS found: $(M+H)^+=462$.

(35b)

Following a procedure analogous to that used in reaction (1d), the semicarbazide amide (78 mg, 0.17 mmol) from reaction (35a) was heated at reflux with aqueous sodium hydroxide solution overnight. After cooling to rt, the reaction was acidified with trifluoroacetic acid. Purification of the crude material by reverse phase HPLC (15–50% acetonitrile/water) provided the desire triazolone as a 1:1 mixture of cis:trans diastereomers (12 mg, 13%). MS found: $(M+H)^+$ =444.

Example 36

3-[4-(2-Methyl-quinolin-4-ylmethoxy)-benzoylamino]-4-(5-oxo-4,5-dihydro-1H-[1,2,4]triazol-3-yl)-pyrrolidine-1-carboxylic Acid tert-butyl Ester Trifluoroacetate (36a)

Following a procedure analogous to that used in reaction (1c), the acid (270 mg, 0.53 mmol) from reaction (19a) was reacted with semicarbazide hydrochloride (80 mg, 0.72 mmol) overnight. The reaction was diluted with ethyl acetate and washed with saturated potassium dihydrogenphosphate and brine. The organic layer was dried and concentrated. Purification of the crude material by reverse phase HPLC (15–50% acetonitrile/water) gave the desired semicarbazide amide (150 mg, 50%). MS found: $(M+H)^+$=563.

(36b)

Following a procedure analogous to that used in reaction (1d), the semicarbazide amide (150 mg, 0.27 mmol) from reaction (36a) was heated at reflux with aqueous sodium hydroxide solution overnight. After cooling to rt, the solution was extracted with ethyl acetate (3×). The organic layer was dried and concentrated. Purification of the crude material by reverse phase HPLC (20–40% acetonitrile/water) furnished the desired triazolone as a mixture of diastereomers (8 mg, 4%). MS found: $(M+H)^+$=545.

Example 37

4-(2-Methyl-quinolin-4-ylmethoxy)-N-[3-(5-oxo-4,5-dihydro-1H-[1,2,4]triazol-3-yl)-tetrahydro-pyran-4-yl]-benzamide trifluoroacetate (37a)

Following a procedure analogous to that used in reaction (1c), the acid (460 mg, 1.09 mmol) from reaction (14a) was reacted with semicarbazide hydrochloride overnight. The reaction was diluted with ethyl acetate and washed with saturated sodium bicarbonate solution and brine. The organic layer was dried and concentrated to give the desired semicarbazide amide (255 mg, 49%). MS found: $(M+H)^+$=478.

(37b)

Following a procedure analogous to that used in reaction (1d), the semicarbazide amide (255 mg, 0.53 mmol) from reaction (37a) was heated at reflux with aqueous sodium hydroxide solution overnight. After cooling to rt, the reaction was acidified with trifluoroacetic acid. Purification of the crude material by reverse phase HPLC (15–50% acetonitrile/water) provided the desired triazolone as a mixture of diastereomers (7 mg, 3%). MS found: $(M+H)^+$=460.

Table 1 below provides representative Examples, the synthesis of which is described above, of the compounds of the present invention.

TABLE 1

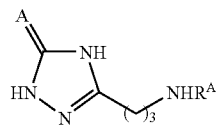

Ex. 1

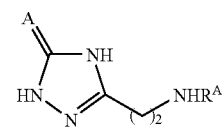

Ex. 2

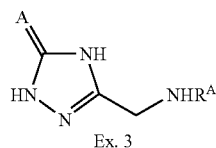

Ex. 3

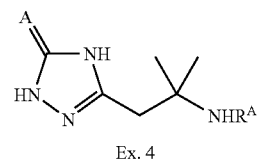

Ex. 4

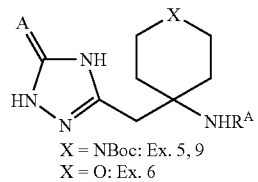

X = NBoc: Ex. 5, 9
X = O: Ex. 6

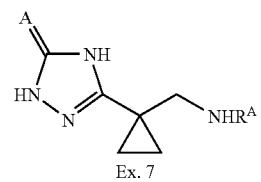

Ex. 7

TABLE 1-continued

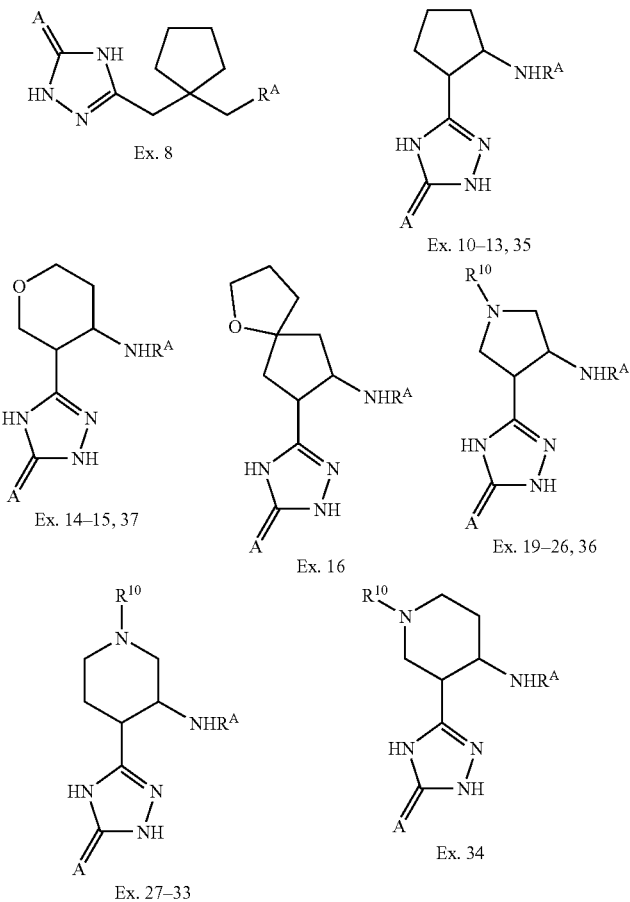

| Ex. | A | R$^A$ | R$^{10}$ | MS (M + H)$^+$ |
|---|---|---|---|---|
| 1 | S | 4-[(2-methyl-4-quinolinyl)methoxy]benzoyl | — | 434 |
| 2 | S | 4-[(2-methyl-4-quinolinyl)methoxy]benzoyl | — | 420 |
| 3 | S | 4-[(2-methyl-4-quinolinyl)methoxy]benzoyl | — | 406 |
| 4 | S | 4-[(2-methyl-4-quinolinyl)methoxy]benzoyl | — | 448 |
| 5 | S | 4-[(2-methyl-4-quinolinyl)methoxy]benzoyl | — | 589 |
| 6 | S | 4-[(2-methyl-4-quinolinyl)methoxy]benzoyl | — | 490 |
| 7 | S | 4-[(2-methyl-4-quinolinyl)methoxy]benzoyl | — | 446 |
| 8 | S | 4-(2-methyl-quinolin-4-ylmethoxy)-benzenesulfonyl | — | 509 |
| 9 | S | 4-(2-isopropyl-benzoimidazol-1-ylmethyl)-benzoyl | — | 590 |
| 10 | S | 4-[(2-methyl-4-quinolinyl)methoxy]benzoyl | — | 460 |
| 11 | S | 4-(2-isopropyl-benzoimidazol-1-ylmethyl)-benzoyl | — | 461 |
| 12 | S | 4-(2-methyl-quinolin-4-ylmethyl)benzoyl | — | 444 |
| 13 | S | 4-(2-methyl-quinolin-4-ylmethoxy)benzenesulfonyl | — | 496 |
| 14 | S | 4-[(2-methyl-4-quinolinyl)methoxy]benzoyl | — | 476 |
| 15 | S | 4-[(2-methyl-4-quinolinyl)methoxy]benzoyl | — | 476 |
| 16 | S | 4-[(2-methyl-4-quinolinyl)methoxy]benzoyl | — | 516 |

TABLE 1-continued

| 19 | S | 4-[(2-methyl-4-quino-linyl)methoxy]benzoyl | t-butoxycarbonyl | 561 |
| --- | --- | --- | --- | --- |
| 20 | S | 4-[(2-methyl-4-quino-linyl)methoxy]benzoyl | H | 461 |
| 21 | S | 4-(1,1-dioxo-2,3-dihydro-1H-1☐⁶-benzo[1,4]thiazin-4-ylmethyl)-benzoyl | t-butoxycarbonyl | 585 |
| 22 | S | 4-(1,1-dioxo-2,3-dihydro-1H-1☐⁶-benzo[1,4]thiazin-4-ylmethyl)-benzoyl | H | 485 |
| 23 | S | 4-[(2-methyl-4-quino-linyl)methoxy]benzoyl | H | 461 |
| 24 | S | 4-[(2-methyl-4-quino-linyl)methoxy]benzoyl | acetyl | 503 |
| 25 | S | 4-[(2-methyl-4-quino-linyl)methoxy]benzoyl | n-propyl | 503 |
| 26 | S | 4-[(2-methyl-4-quino-linyl)methoxy]benzoyl | H | 461 |
| 27 | S | 4-[(2-methyl-4-quino-linyl)methoxy]benzoyl | t-butoxycarbonyl | 575 |
| 28 | S | 4-[(2-methyl-4-quino-linyl)methoxy]benzoyl | H | 475 |
| 29 | S | 4-[(2-methyl-4-quino-linyl)methoxy]benzoyl | acetyl | 517 |
| 30 | S | 4-[(2-methyl-4-quino-linyl)methoxy]benzoyl | n-propyl | 517 |
| 31 | S | 4-[(2-methyl-4-quino-linyl)methoxy]benzoyl | methanesulfonyl | 553 |
| 32 | S | 4-[(2-methyl-4-quino-linyl)methoxy]benzoyl | isopropyl | 517 |
| 33 | S | 4-[(2-methyl-4-quino-linyl)methoxy]benzoyl | methyl | 489 |
| 34 | S | 4-[(2-methyl-4-quino-linyl)methoxy]benzoyl | H | 475 |
| 35 | O | 4-[(2-methyl-4-quino-linyl)methoxy]benzoyl | — | 444 |
| 36 | O | 4-[(2-methyl-4-quino-linyl)methoxy]benzoyl | t-butoxycarbonyl | 545 |
| 37 | O | 4-[(2-methyl-4-quino-linyl)methoxy]benzoyl | — | 460 |

Table 2 demonstrates additional representative examples of the present invention. Each entry $R^B$ in the table is intended to be paired independently with each formula at the start of the table. For example, example 1 in Table 2 is intended to be paired with each of the following formulae A—AG. From formulae A—AG, if a formula contains variables $R^{10}$ and/or n, each entry $R^B$ is intended to be paired with individual designation of $R^{10}$ and/or m, independently at each occurrence, listed below.

$R^{10}$ is H, methyl, ethyl, isopropyl, isobutyl, 2-propynyl, acetyl, 2,2-dimethylpropanoyl, t-butoxycarbonyl, 3-methylbutanoyl, isobutyryl, isonicotinoyl, phenoxyacetyl, methanesulfonyl, 3-pyridinylmethyl, 4-pyridinylmethyl, 3-pyridinylcarbonyl, 4-piperidinylcarbonyl, 4-morpholinylacetyl, 4-morpholinomethyl, or [1-(t-butoxycarbonyl)-4-piperidinyl]carbonyl;

m is 0 or 1. A is oxygen or sulfur.

TABLE 2

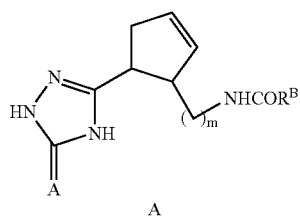

A

TABLE 2-continued

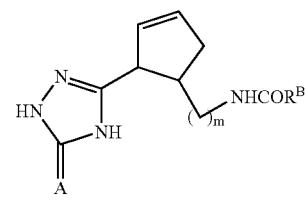

B

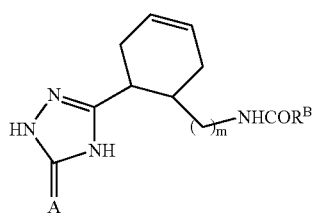

C

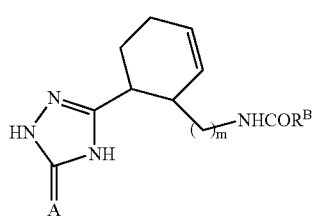

D

TABLE 2-continued
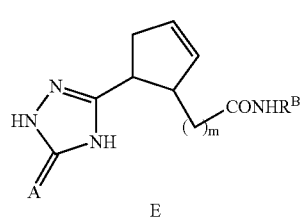
E
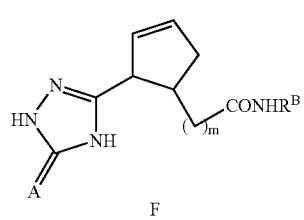
F
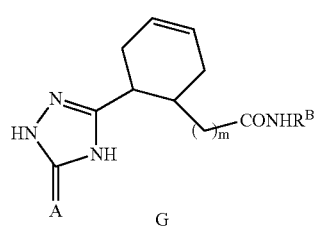
G
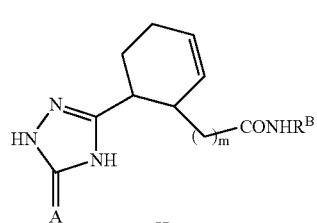
H
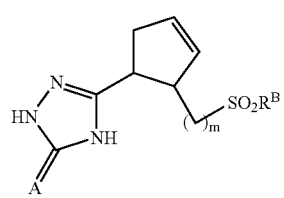
I
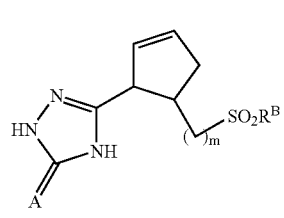
J
TABLE 2-continued
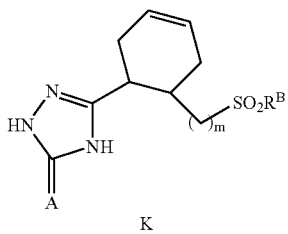
K
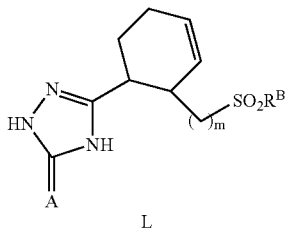
L
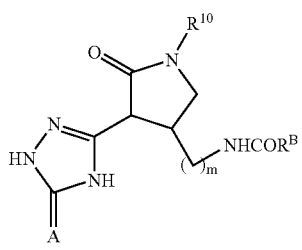
M
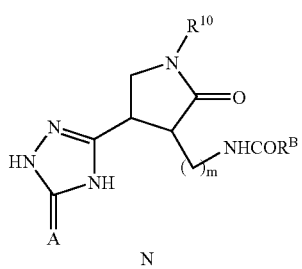
N
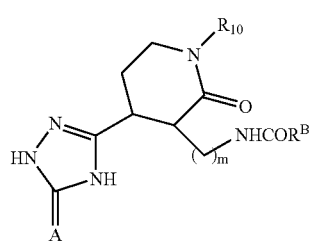
O
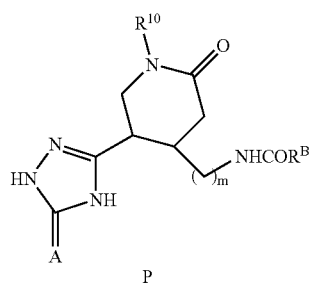
P TABLE 2-continued
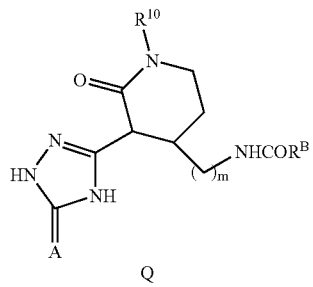
Q
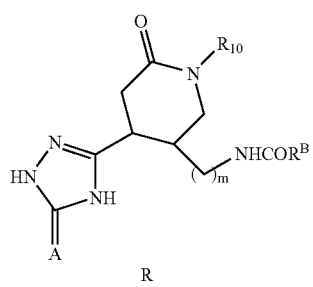
R
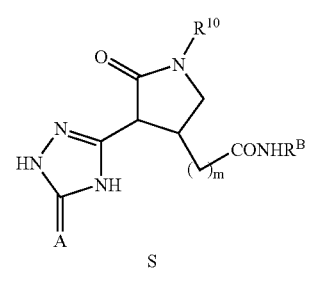
S
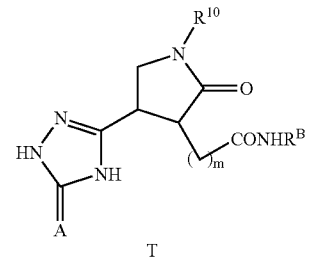
T
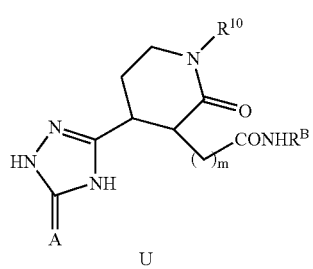
U
TABLE 2-continued
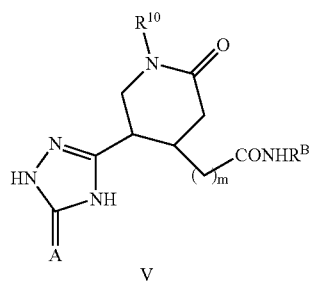
V
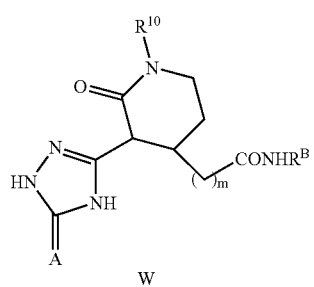
W
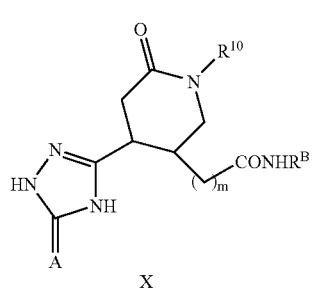
X
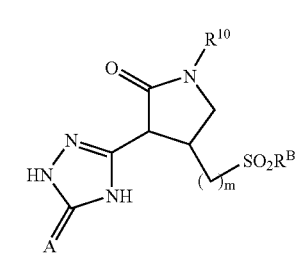
Y
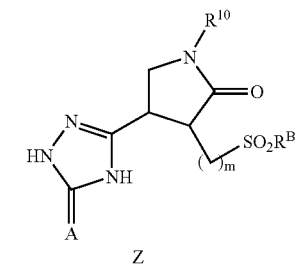
Z TABLE 2-continued

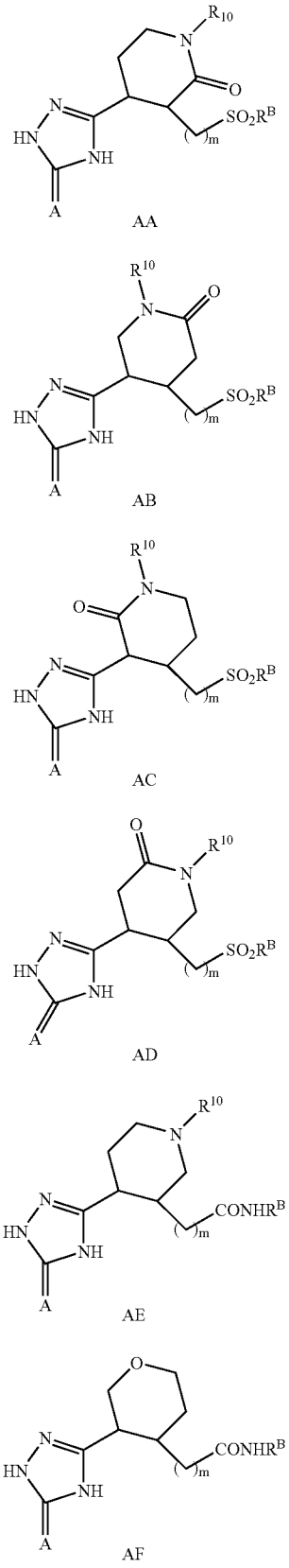

| Ex | $R^B$ |
|---|---|
| 1 | 4-phenylphenyl |
| 2 | 4-phenoxyphenyl |
| 3 | 4-benzyloxyphenyl |
| 4 | 4-(2-methylphenyl)phenyl |
| 5 | 4-(2-methoxyphenyl)phenyl |
| 6 | 4-(3-methylphenyl)phenyl |
| 7 | 4-(3-methoxyphenyl)phenyl |
| 8 | 4-(2-methylphenoxy)phenyl |
| 9 | 4-(2-methoxyphenoxy)phenyl |
| 10 | 4-(2-trifluoromethylphenyl)phenyl |
| 11 | 4-(2-trifluoromethylphenoxy)phenyl |
| 12 | 4-(3,5-dimethylphenyl)phenyl |
| 13 | 4-[(2,5-dimethylbenzyl)oxy]phenyl |
| 14 | 4-(4-pyridyl)phenyl |
| 15 | 4-(3-methyl-2-pyridyl)phenyl |
| 16 | 4-[(2-methyl-3-pyridyl)methyl]phenyl |
| 17 | 4-[(2-methyl-3-pyridyl)methoxy]phenyl |
| 18 | 4-[(2,3,5-trimethyl-4-pyridinyl)methyl]phenyl |
| 19 | 4-[(2,3,5-trimethyl-4-pyridinyl)methoxy]phenyl |
| 20 | 2-[2-(2-methylphenyl)]pyridyl |
| 21 | 5-[2-(2-methoxyphenyl)]pyridyl |
| 22 | 4-[(3,5-dimethyl-1H-pyrazol-4-yl)methyl]phenyl |
| 23 | 4-[(3,5-dimethyl-1H-pyrazol-4-yl)methoxy]phenyl |
| 24 | 4-[(1,3,5-trimethyl-1H-pyrazol-4-yl)methyl]phenyl |
| 25 | 4-[(1,3,5-trimethyl-1H-pyrazol-4-yl)methoxy]phenyl |
| 26 | 4-(1-naphthylmethyl)phenyl |
| 27 | 4-(1-naphthylmethoxy)phenyl |
| 28 | 4-(4-quinolinyl)phenyl |
| 29 | 4-[(2-methyl-4-quinolinyl)methyl]phenyl |
| 30 | 4-(2-methyl-4-quinolinylmethoxy)phenyl |
| 31 | 4-(2-methyl-1-oxo-4-quinolinylmethyl)phenyl |
| 32 | 4-(2-methyl-1-oxo-4-quinolinylmethoxy)phenyl |
| 33 | 4-{[(2-methyl-4-quinolinyl)methyl]amino}phenyl |
| 34 | {4-[(2-methyl-4-quinolinyl)methyl]phenyl}methyl |
| 35 | 4-[(2-ethyl-4-quinolinyl)methyl]phenyl |
| 36 | 4-[(2-ethyl-4-quinolinyl)methoxy]phenyl |
| 37 | 4-{[2-(trifluoromethyl)-4-quinolinyl]methyl}phenyl |
| 38 | 4-{[2-(trifluoromethyl)-4-quinolinyl]methoxy}phenyl |
| 39 | 4-[(5-quinolinyloxy)methyl]phenyl |
| 40 | 4-[(5-quinolinyloxy)methoxy]phenyl |
| 41 | 4-{[(2-methyl-8-quinolinyl)oxy]methyl}phenyl |
| 42 | 4-{[(2-methyl-8-quinolinyl)oxy]methoxy}phenyl |
| 43 | 4-[(5-isoquinolinyloxy)methyl]phenyl |
| 44 | 4-[(5-isoquinolinyloxy)methoxy]phenyl |
| 45 | 4-(3-phenyl-4,5-dihydro-5-isoxazolyl)phenyl |
| 46 | 4-[3-(4-pyridyl)-4,5-dihydro-5-isoxazolyl]phenyl |
| 47 | 4-[3-(3-pyridyl)-4,5-dihydro-5-isoxazolyl]phenyl |
| 48 | 4-[3-(2-pyridyl)-4,5-dihydro-5-isoxazolyl]phenyl |
| 49 | 4-[3-(4-quinolinyl)-4,5-dihydro-5-isoxazolyl]phenyl |
| 50 | 4-[3-(2,6-dimethyl-4-pyridyl)-4,5-dihydro-5-isoxazolyl]phenyl |
| 51 | 3-methoxy-4-[3-(4-pyridyl)-4,5-dihydro-5-isoxazolyl]phenyl |
| 52 | 4-[5-(4-pyridyl)-4,5-dihydro-3-isoxazolyl]phenyl |
| 53 | 4-[5-(3-pyridyl)-4,5-dihydro-3-isoxazolyl]phenyl |
| 54 | 4-[5-(2-pyridyl)-4,5-dihydro-3-isoxazolyl]phenyl |
| 55 | 1-[(2-methyl-4-quinolinyl)methyl]-1H-indol-5-yl |
| 56 | 1-[(2-methyl-4-quinolinyl)methoxy]-1H-indol-5-yl |
| 57 | 4-(1H-indol-3-ylmethyl)phenyl |
| 58 | 4-(1H-indol-3-ylmethoxy)phenyl |
| 59 | 4-[(2-methyl-1H-indol-3-yl)methyl]phenyl |
| 60 | 4-[(2-methyl-1H-indol-3-yl)methoxy]phenyl |
| 61 | 4-[(2-methyl-1H-indol-1-yl)-methyl]phenyl |
| 62 | 4-[(2-methyl-1H-indol-1-yl)-methoxy]phenyl |
| 63 | 6-[(2-methyl-4-quinolinyl)methyl]-1-naphthyl |

TABLE 2-continued

| | |
|---|---|
| 64 | 6-[(2-methyl-4-quinolinyl)methoxy]-1-naphthyl |
| 65 | 6-[(2-methyl-4-quinolinyl)methyl]-1,2,3,4-tetrahydro-1-isoquinolinyl |
| 66 | 6-[(2-methyl-4-quinolinyl)methoxy]-1,2,3,4-tetrahydro-1-isoquinolinyl |
| 67 | 4-[(1H-benzimidazol-1-yl)methyl]phenyl |
| 68 | 4-[(1H-benzimidazol-1-yl)methoxy]phenyl |
| 69 | 4-[(2-methyl-1H-benzimidazol-1-yl)methyl]phenyl |
| 70 | 4-[(2-methyl-1H-benzimidazol-1-yl)methoxy]phenyl |
| 71 | 4-[(2-isopropyl-1H-benzimidazol-1-yl)methyl]phenyl |
| 72 | 4-[(2-isopropyl-1H-benzimidazol-1-yl)methoxy]phenyl |
| 73 | 4-{[(2-trifluoromethyl-1H-benzimidazol-1-yl)]methyl}phenyl |
| 74 | 4-{[(2-trifluoromethyl-1H-benzimidazol-1-yl)]methoxy}phenyl |
| 75 | 4-{[(2-(methylthio)-1H-benzimidazol-1-yl)]methyl}phenyl |
| 76 | 4-{[(2-(methylthio)-1H-benzimidazol-1-yl)]methoxy}phenyl |
| 77 | 4-[(5-phenyl-1H-imidazol-1-yl)methyl]phenyl |
| 78 | 4-[(5-phenyl-1H-imidazol-1-yl)methoxy]phenyl |
| 79 | 4-[(1,1-dioxido-2,3-dihydro-4H-1,4-benzothiazin-4-yl)methyl]phenyl |
| 80 | 4-[(1,1-dioxido-2,3-dihydro-4H-1,4-benzothiazin-4-yl)methoxy]phenyl |
| 81 | 4-[2,2-dimethyl-1,1-dioxido-2,3-dihydro-4H-1,4-benzothiazin-4-yl)methyl]phenyl |
| 82 | 4-[2,2-dimethyl-1,1-dioxido-2,3-dihydro-4H-1,4-benzothiazin-4-yl)methoxy]phenyl |
| 83 | 4-[(2-ethylpyrazolo[1,5-a]pyridin-3-yl)-methyl]phenyl |
| 84 | 4-[(2-ethylpyrazolo[1,5-a]pyridin-3-yl)-methoxy]phenyl |
| 85 | 4-(1,3-dihydrofuro[3,4-b]quinolin-9-ylmethyl)phenyl |
| 86 | 4-(1,3-dihydrofuro[3,4-b]quinolin-9-ylmethoxy)phenyl |
| 87 | 4-[(2-methyl-1-oxido-4-quinolinyl)methyl]phenyl |
| 88 | 4-[(2-methyl-1-oxido-4-quinolinyl)methoxy]phenyl |

Utility

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TACE and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyagia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denotes agents that selectively inhibit COX-2 function. Such agents include, but are not limited to, celecoxib (Celebrex®), rofecoxib (Vioxx®), meloxicam (Movicox®), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel®), infliximab (Remicade®), adalimumab (D2E7), CDP-571 (Humicade®), and CDP-870.

Other anti-inflammatory agents that may be used in combination with the compounds of this invention, include, but are not limited to, methotrexate, interleukin-1 antagonists (e.g., anakinra (Kineret®)), dihydroorotate synthase inhibitors (e.g., leflunomide (Arava®)), and p38 MAP kinase inhibitors.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 µM for the inhibition of a desired MP. Preferred compounds of the present invention have $K_i$'s or $IC_{50}$'s of $\leq 1$ µM. More preferred compounds of the present invention have $K_i$'s or $IC_{50}$'s of $\leq 0.1$ µM. Even more preferred compounds of the present invention have $K_i$'s or $IC_{50}$'s of $\leq 0.01$ µM. Still more preferred compounds of the present invention have $K_i$'s or $IC_{50}$'s of $\leq 0.001$ µM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. Trans. Ortho. Res. Soc. 1995, 20, 341). Therefore, in order to accumulate BNC aggrecanase in culture media, cartilage is first depleted of endogenous aggrecan by stimulation with 500 mg/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al. Biochem J. 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a $K_m$ of 1.5+/–0.35 µM for aggrecanase.

To evaluate inhibition of aggrecanase, compounds are prepared as 10 mM stocks in DMSO, water or other solvents and diluted to appropriate concentrations in water. Drug (50 µL) is added to 50 µL of aggrecanase-containing media and 50 µL of 2 mg/mL aggrecan substrate and brought to a final volume of 200 µL in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 µg GAG) for 2 hr at 37° C. and then with keratanase (0.1 units/10 µg GAG) and keratanase II (0.002 units/10 µg GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 µL of Tris glycine SDS sample buffer (Novex®) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2 \times 10^6$ cells/mL in 96 well polystyrene plates. Cells were preincubated 10 minutes with compound, then stimulated with 1 µg/mL LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 µL of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 µg/mL LPS. Plates are incubated for 5 hours in an atmosphere of 5% $CO_2$ in air. At the end of 5 hours, 750 µL of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction in Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 µM in all assays. Initial velocities, in the presence or absence of inhibitor, were measured as slopes of the linear portion of the product progress curves. $IC_{50}$ values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, N.Y., 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibition, the $IC_{50}$ values were converted to $K_i$ values as previously described.

Compounds tested in the above assay are considered to be active if they exhibit a $K_i$ of $\leq 10$ µM. Preferred compounds of the present invention have $K_i$'s of $\leq 1$ µM. More preferred compounds of the present invention have $K_i$'s of $\leq 0.1$ µM. Even more preferred compounds of the present invention have $K_i$'s of $\leq 0.01$ µM. Still more preferred compounds of the present invention have $K_i$'s of $\leq 0.001$ µM.

Using the methodology described above, a number of compounds of the present invention were found to exhibit $K_i$'s of $\leq 10$ µM, thereby confirming the utility of the compounds of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder (as defined previously). In another embodiment, the package insert states that the pharmaceutical composition can be used in combination (as defined previously) with a second therapeutic agent to treat an inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 mg to about 100 mg of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:
1. A compound of formula (I):

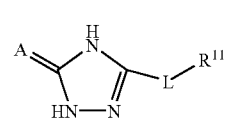

or a stereoisomer or pharmaceutically acceptable salt form thereof, wherein;
A is O or S;
L is —$(CR^2R^3)$—$(CR^4R^5)_n$—$(CR^6R^7)_{n1}$—;
alternatively, L is selected from the group:

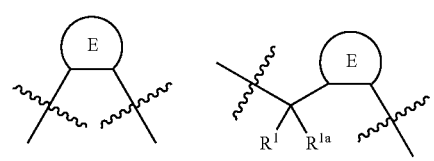

-continued

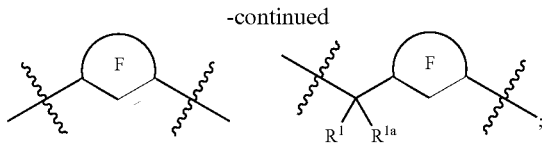

$R^1$ is, independently at each occurrence, H, $C_{1-6}$ alkyl, $C_{2-6}$ alkenyl, or $C_{2-6}$ alkynyl;

$R^{1a}$ is, independently at each occurrence, H, $C_{1-6}$ alkyl, $C_{2-6}$ alkenyl, or $C_{2-6}$ alkynyl;

$R^2$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$—$Q^1$, —$(CR^aR^{a1})_rNR^a(CR^aR^{a1})_s$—$Q^1$, —$(CR^aR^{a1})_rC(O)(CR^aR^{a1})_s$—$Q^1$, —$(CR^aR^{a1})_rC(O)O(CR^aR^{a1})_s$—$Q^1$, —$(CR^aR^{a1})_rOC(O)(CR^aR^{a1})_s$—$Q^1$, —$(CR^aR^{a1})_rC(O)NR^aR^{a1}$, —$(CR^aR^{a1})_rC(O)NR^a(CR^aR^{a1})_s$—$Q^1$, —$(CR^aR^{a1})_rNR^aC(O)(CR^aR^{a1})_s$—$Q^1$, —$(CR^aR^{a1})_rOC(O)O(CR^aR^{a1})_s$—$Q^1$, —$(CR^aR^{a1})_rOC(O)NR^a(CR^aR^{a1})_s$—$Q^1$, —$(CR^aR^{a1})_rNR^aC(O)NR^a(CR^aR^{a1})_s$—$Q^1$, —$(CR^aR^{a1})_rS(O)_p(CR^aR^{a1})_s$—$Q^1$, —$(CR^aR^{a1})_rSO_2NR^a(CR^aR^{a1})_s$—$Q^1$, —$(CR^aR^{a1})_rNR^aSO_2(CR^aR^{a1})_s$—$Q^1$, or —$(CR^aR^{a1})_rNR^aSO_2NR^a(CR^aR^{a1})_s$—$Q^1$;

$R^3$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$—Q, —$(CR^aR^{a1})_rNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_rS(O)_p(CR^aR^{a1})_s$—Q, —$(CR^aR^{a1})_rSO_2NR^a(CR^aR^{a1})_s$—Q, or —$(CR^aR^{a1})_rNR^aSO_2(CR^aR^{a1})_s$—Q;

Q is, independently at each occurrence, H, $CHF_2$, $CH_2F$, $CF_3$, a $C_{3-13}$ carbocycle substituted with 0–5 $R^d$, or a 5–14 membered heterocycle consisting of carbon atoms and 1–4 heteroatoms selected from the group consisting of N, O, and $S(O)_p$, and substituted with 0–5 $R^d$;

$Q^1$ is, independently at each occurrence, H, a $C_{3-13}$ carbocycle substituted with 0–5 $R^d$, or a 5–14 membered heterocycle consisting of carbon atoms and 1–4 heteroatoms selected from the group consisting of N, $NR^{10}$, O, and $S(O)_p$, and substituted with 0–5 $R^d$;

$R^4$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

$R^5$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

$R^6$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

$R^7$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

n is 0 or 1;

n1 is 0 or 1;

alternatively, $R^2$ and $R^3$, together with the carbon atom to which they are attached, combine to form a 3–8 membered carbocyclic or heterocyclic ring consisting of carbon atoms and 0–2 ring heteroatoms selected from O, N, $NR^{10}$, and $S(O)_p$, and 0–2 double bonds, and substituted with 0–3 $R^9$; and the carbocyclic or heterocyclic ring is optionally fused to a 5–6 membered carbocycle or heterocycle consisting of carbon atoms and 0–2 ring heteroatoms selected from O, N, $NR^{10}$, and $S(O)_p$, and 0–2 double bonds, and substituted with 0–3 $R^9$;

alternatively, when n is 1, $R^4$ and $R^5$, together with the carbon atom to which they are attached, combine to form a 3–8 membered carbocyclic or heterocyclic ring consisting of carbon atoms and 0–2 ring heteroatoms selected from O, N, $NR^{10}$, and $S(O)_p$, and 0–2 double bonds, and substituted with 0–3 $R^9$; and the carbocyclic or heterocyclic ring is optionally fused to a 5–6 membered carbocycle or heterocycle consisting of carbon atoms and 0–2 ring heteroatoms selected from O, N, $NR^{10}$, and $S(O)_p$, and 0–2 double bonds, and substituted with 0–3 $R^9$;

alternatively, when n1 is 1, $R^6$ and $R^7$, together with the carbon atom to which they are attached, combine to form a 3–8 membered carbocyclic or heterocyclic ring consisting of carbon atoms and 0–2 ring heteroatoms selected from O, N, $NR^{10}$, and $S(O)_p$, and 0–2 double bonds, and substituted with 0–3 $R^9$; and the carbocyclic or heterocyclic ring is optionally fused to a 5–6 membered carbocycle or heterocycle consisting of carbon atoms and 0–2 ring heteroatoms selected from O, N, $NR^{10}$, and $S(O)_p$, and 0–2 double bonds, and substituted with 0–3 $R^9$;

ring E is a 3–8 membered carbocyclic or heterocyclic ring consisting of carbon atoms and 0–2 ring heteroatoms selected from O, N, $NR^{10}$, and $S(O)_p$, and 0–2 double bonds, and substituted with 0–3 $R^c$; and the carbocyclic or heterocyclic ring is optionally fused to a 5–6 membered carbocycle or heterocycle consisting of carbon atoms and 0–2 ring heteroatoms selected from O, N, $NR^{10}$, and $S(O)_p$, and 0–2 double bonds, and substituted with 0–3 $R^9$;

ring F is a 4–8 membered carbocyclic or heterocyclic ring consisting of carbon atoms and 0–2 ring heteroatoms selected from O, N, $NR^{10}$, and $S(O)_p$, and 0–2 double bonds, and substituted with 0–3 $R^c$; and the carbocyclic or heterocyclic ring is optionally fused to a 5–6 membered carbocycle or heterocycle consisting of carbon atoms and 0–2 ring heteroatoms selected from O, N, $NR^{10}$, and $S(O)_p$, and 0–2 double bonds, and substituted with 0–3 $R^9$;

$R^{11}$ is —W—U—X—Y—Z—$U^a$—$X^a$—$Y^a$—$Z^a$;

W is $(CR^aR^{a1})_m$, $C_{2-3}$ alkenylene, or $C_{2-3}$ alkynylene;

U is O, C(O), $CR^a(OH)$, C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, or $NR^{a1}SO_2NR^{a1}$;

X is absent or is $C_{1-3}$ alkylene, $C_{2-3}$ alkenylene, or $C_{2-3}$ alkynylene;

Y is absent or is O, $NR^{a1}$, $S(O)_p$, or C(O);

Z is a $C_{3-13}$ carbocycle substituted with 0–5 $R^b$, or a 5–14 membered heterocycle consisting of carbon atoms and 1–4 heteroatoms selected from the group consisting of N, O, and $S(O)_p$ and substituted with 0–5 $R^b$;

$U^a$ is absent or is O, $NR^{a1}$, C(O), $CR^a(OH)$, C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, or $NR^{a1}SO_2NR^{a1}$;

$X^a$ is absent or is $C_{1-10}$ alkylene, $C_{2-10}$ alkenylene, or $C_{2-10}$ alkynylene;

$Y^a$ is absent or is O, $NR^{a1}$, $S(O)_p$, or C(O);

$Z^a$ is H, a $C_{3-13}$ carbocycle substituted with 0–5 $R^c$, or a 5–14 membered heterocycle consisting of carbon atoms and 1–4 heteroatoms selected from the group consisting of N, O, and $S(O)_p$ and substituted with 0–5 $R^c$;

provided that U, Y, Z, $U^a$, $Y^a$, and $Z^a$ do not combine to form a N—N, N—O, O—N, O—O, $S(O)_p$—O, O—S$(O)_p$ or $S(O)_p$—$S(O)_p$ group;

$R^a$ is, independently at each occurrence, H, $C_{1-6}$ alkyl, phenyl, or benzyl;

$R^{a1}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

$R^{a2}$ is, independently at each occurrence, $C_{1-4}$ alkyl, phenyl, or benzyl;

$R^{a3}$ is, independently at each occurrence, H, $C_{1-6}$ alkyl substituted with $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^b$, at each occurrence, is independently selected from $C_{1-6}$ alkyl substituted with 0–1 $R^{c1}$, $OR^a$, $SR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, —$CF_3$, —$CF_2CF_3$, —$CHF_2$, —$CH_2F$, or phenyl;

$R^c$ is, independently at each occurrence, H, $OR^a$, Cl, F, Br, I, =O, CN, $NO_2$, $CF_3$, —$CF_2CF_3$, $CH_2F$, $CHF_2$, —$(CR^aR^{a1})_rNR^aR^{a1}$, —$(CR^aR^{a1})_rC(=NCN)NR^aR^{a1}$, —$(CR^aR^{a1})_rC(=NR^a)NR^aR^{a1}$, —$(CR^aR^{a1})_rC(=NOR^a)NR^aR^{a1}$, —$(CR^aR^{a1})_rC(O)NR^aOH$, —$(CR^aR^{a1})_rC(O)R^{a1}$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR_aR^{a1})_r$—$C_{3-10}$ carbocycle substituted with 0–2 $R^{c1}$, or —$(CR^aR^{a1})_r$-5–14 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^{c1}$ is, independently at each occurrence, H, $C_{1-4}$ alkyl, $OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, $OR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, —$CF_3$, —$CF_2CF_3$, $C_{3-10}$ carbocycle, or a 5–14 membered heterocycle consisting of carbon atoms and 1–4 heteroatoms selected from the group consisting of N, O, and $S(O)_p$;

$R^e$ is, independently at each occurrence, H, $C_{1-6}$ alkyl, $C_{1-6}$ alkoxy, phenoxy, benzoxy, $C_{3-10}$ carbocycle substituted with 0–2 $R^{c1}$, or a 5–10 membered heterocycle consisting of carbon atoms and 1–4 heteroatoms selected from the group consisting of N, O, and $S(O)_p$, and substituted with 0–2 $R^{c1}$;

$R^9$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR_aR^{a1})_r$—$C_{3-10}$ carbocycle substituted with 0–2 $R^{c1}$, or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

$R^{10}$ is, independently at each occurrence, H, —$(CR^aR^{a1})_tNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, (—$(CR^aR^{a1})_rC(O)NR^aR^{a1}$, —$(CR^aR^{a1})_tNR^aC(O)R^{a1}$, —$(CR^aR^{a1})_rC(S)NR^aR^{a1}$, $(CR^aR^{a1})_tOC(O)NR^aR^{a1}$, —$(CR^aR^{a1})_tNR^aC(O)OR^{a1}$, —$(CR^aR^{a1})_tNR^aC(O)NR^aR^{a1}$, —$(CR^aR^{a1})_rS(O)_pR^{a3}$, —$(CR^aR^{a1})_r$ $SO_2NR^aR^{a1}$, —$(CR^aR^{a1})_tNR^aSO_2R^{a3}$, —$(CR^aR^{a1})_t$ $NR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR_aR^{a1})_r$—$C_{3-10}$ carbocycle substituted with 0–2 $R^{c1}$, or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

m, at each occurrence, is selected from 0, 1, 2 and 3;
p, at each occurrence, is selected from 0, 1, and 2;
r, at each occurrence, is selected from 0, 1, 2, 3, and 4;
s, at each occurrence, is selected from 0, 1, 2, 3, and 4; and
t, at each occurrence, is selected from 1, 2, 3, and 4;
provided that:
(i) when L is $CR^2R^3$ or $CR^2R^3CH_2$, $Z^a$ is other than H;
(ii) when Z is cyclohexyl, benzodiazepinyl or a nitrogen-containing 10-membered bicyclic heteroaryl, then $Z^a$ is other than phenyl or phenyl fused carbocycle;
(iii) when Z is phenyl, and $Z^a$ is oxazolyl, then $R^c$ is other than phenyl;

(iv) when Z is a C$_{5-7}$ cycloalkyl, then R$^b$ is other than phenyl;
(v) when A is S, and L is 1,2-phenylene, then Z$^a$ is other than thienyl or phenyl substituted with triazolthione;
(vi) when A is S, L is CH$_2$, U—X—Y forms O or S, and Z is a benzopyranyl, quinazolinyl, or triazinyl ring, then Z$^a$ is other than phenyl;
(vii) when A is S, L is 4,5,6-7-tetrahydrobenzothienyl, and U—X—Y forms C(O)NH, Z is other than 5,6,7,8-tetrahydro-benzothieno[2,3-b]pyridinyl; and
(viii) when L is 1,2-phenylene or 1,3-phenylene, then U$^a$—X$^a$—Y$^a$ forms other than C$_{1-2}$ alkylene or CH$_2$NR$^{a1}$.

2. A compound according to claim 1, wherein:
R$^2$ is Q$^1$, C$_{1-6}$ alkylene-Q$^1$, C$_{2-6}$ alkenylene-Q$^1$, C$_{2-6}$ alkynylene-Q$^1$, —(CR$^a$R$^{a1}$)$_r$O(CR$^a$R$^{a1}$)$_s$—Q$^1$, —(CR$^a$R$^{a1}$)$_r$NR$^a$(CR$^a$R$^{a1}$)$_s$—Q$^1$, —(CR$^a$R$^{a1}$)$_r$C(O)(CR$^a$R$^{a1}$)$_s$—Q$^1$, —(CR$^a$R$^{a1}$)$_r$C(O)O(CR$^a$R$^{a1}$)$_s$—Q$^1$, —(CR$^a$R$^{a1}$)$_r$OC(O)(CR$^a$R$^{a1}$)$_s$—Q$^1$, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$—Q$^1$, —(CR$^a$R$^{a1}$)$_r$NR$^a$C(O)(CR$^a$R$^{a1}$)$_s$—Q$^1$, —(CR$^a$R$^{a1}$)$_r$S(O)$_p$(CR$^a$R$^{a1}$)$_s$—Q$^1$, —(CR$^a$R$^{a1}$)$_r$SO$_2$NR$^a$(CR$^a$R$^{a1}$)$_s$—Q$^1$, or —(CR$^a$R$^{a1}$)$_r$NR$^a$SO$_2$(CR$^a$R$^{a1}$)$_s$—Q$^1$;
R$^3$ is Q, C$_{1-6}$ alkylene-Q, C$_{2-6}$ alkenylene-Q, C$_{2-6}$ alkynylene-Q, —(CH$_2$)$_r$O(CH$_2$)$_s$—Q, —(CH$_2$)$_r$NR$^a$(CH$_2$)$_s$—Q, —(CH$_2$)$_r$C(O)(CH$_2$)$_s$—Q, —(CH$_2$)$_r$C(O)O(CH$_2$)$_s$—Q, —(CH$_2$)$_r$C(O)NR$^a$R$^{a1}$, —(CH$_2$)$_r$C(O)NR$^a$(CH$_2$)$_s$—Q, —(CH$_2$)$_r$NR$^a$C(O)(CH$_2$)$_s$—Q, —(CH$_2$)$_r$S(O)$_p$(CH$_2$)$_s$—Q, —(CH$_2$)$_r$SO$_2$NR$^a$(CH$_2$)$_s$—Q, or —(CH$_2$)$_r$NR$^a$SO$_2$(CH$_2$)$_s$—Q;
R$^4$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;
R$^5$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;
R$^6$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;
R$^7$ is H, C$_{1-6}$ alkyl substituted with 0–1 R$^b$, C$_{2-6}$ alkenyl substituted with 0–1 R$^b$, or C$_{2-6}$ alkynyl substituted with 0–1 R$^b$;
alternatively, R$^2$ and R$^3$, together with the carbon atom to which they are attached, combine to form a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–2 R$^9$;
alternatively, when n is 1, R$^4$ and R$^5$ together with the carbon atom to which they are attached combine to form a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–2 R$^9$;
alternatively, when n1 is 1, R$^6$ and R$^7$ together with the carbon atom to which they are attached combine to form a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–2 R$^9$;
ring E is a 3–8 membered carbocyclic or heterocyclic ring consisting of carbon atoms and 0–2 ring heteroatoms selected from O, N, NR$^{10}$, and S(O)$_p$, and 0–2 double bonds, and substituted with 0–3 R$^c$;
ring F is a 4–8 membered carbocyclic or heterocyclic ring consisting of carbon atoms and 0–2 ring heteroatoms selected from O, N, NR$^{10}$, and S(O)$_p$, and 0–2 double bonds, and substituted with 0–3 R$^c$;
W is (CR$^a$R$^{a1}$)$_m$;
U is O, C(O), CR$^a$(OH), C(O)O, OC(O), C(O)NR$^{a1}$, NR$^{a1}$C(O), S(O)$_p$, S(O)$_p$NR$^{a1}$, or NR$^{a1}$S(O)$_p$;
X is absent or is C$_{1-3}$ alkylene;
Z is a C$_{3-8}$ cycloalkyl substituted with 0–5 R$^b$, a C$_{3-8}$ cycloalkenyl substituted with 0–5 R$^b$, phenyl substituted with 0–5 R$^b$, naphthyl substituted with 0–5 R$^b$, or a 5–14 membered heterocycle consisting of carbon atoms and 1–4 heteroatoms selected from the group consisting of N, O, and S(O)$_p$ and substituted with 0–5 R$^b$;
U$^a$ is absent or is O, NR$^{a1}$, C(O), CR$^a$(OH), C(O)O, C(O)NR$^{a1}$, NR$^{a1}$C(O), S(O)$_p$, S(O)$_p$NR$^{a1}$, or NR$^{a1}$S(O)$_p$;
X$^a$ is absent or is C$_{1-4}$ alkylene, C$_{2-4}$ alkenylene, or C$_{2-4}$ alkynylene;
Y$^a$ is absent or is O or NR$^{a1}$;
Z$^a$ is a C$_{6-13}$ carbocycle substituted with 0–5 R$^c$, or a 5–14 membered heterocycle consisting of carbon atoms and 1–4 heteroatoms selected from the group consisting of N, O, and S(O)$_p$, and substituted with 0–5 R$^c$;
R$^a$ is, independently at each occurrence, H, C$_{1-6}$ alkyl, phenyl, or benzyl;
R$^{a1}$ is, independently at each occurrence, H, C$_{1-6}$ alkyl, C$_{2-6}$ alkenyl, C$_{2-6}$ alkynyl, and —(CH$_2$)$_r$-3–8 membered carbocyclic or heterocyclic ring consisting of carbon atoms and 0–2 ring heteroatoms selected from N, NR$^{a2}$, O, and S(O)$_p$;
alternatively, R$^a$ and R$^{a1}$ when attached to a nitrogen, together with the nitrogen to which they are attached, combine to form a 5 or 6 membered heterocycle consisting of carbon atoms and from 0–1 additional heteroatoms selected from N, NR$^{a2}$, O, and S(O)$_p$;
R$^c$ is, independently at each occurrence, H, OR$^a$, Cl, F, Br, =O, CN, NO$_2$, CF$_3$, CH$_2$F, CHF$_2$, —CF$_2$CF$_3$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, —(CH$_2$)$_r$—C$_{3-6}$ carbocycle substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;
alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;
alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;
R$^d$ is, independently at each occurrence, C$_{1-6}$ alkyl, OR$^a$, Cl, F, Br, =O, CN, NO$_2$, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, CF$_3$, C$_{3-6}$ carbocycle and a 5–6 membered heterocycle consisting of carbon atoms and 1–4 heteroatoms selected from the group consisting of N, O, and $S(O)_p$;

$R^9$ is, independently at each occurrence, H, $-(CR^aR^{a1})_r$ $NR^aR^{a1}$, $-(CR^aR^{a1})_rC(O)NR^aOH$, $-(CR^aR^{a1})_rC(O)(CR^aR^{a1})_sR^e$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rOC(O)NR^aR^{a1}$, $-(CR^aR^{a1})_rNR^aC(O)OR^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, $-(CR^aR^{a1})_r-C_{3-10}$ carbocycle substituted with 0–2 $R^{c1}$, or $-(CR^aR^{a1})_r-$5–10 membered heterocycle consisting of carbon atoms and 1–4 heteroatoms selected from the group consisting of N, O, and $S(O)_p$ and substituted with 0–2 $R^{c1}$; and $R^{10}$ is, independently at each occurrence, H, $-(CR^aR^{a1})_t$ $NR^aR^{a1}$, $-(CR^aR^{a1})_rC(O)NR^aOH$, $-(CR^aR^{a1})_rC(O)(CR^aR^{a1})_sR^e$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_tOC(O)NR^aR^{a1}$, $-(CR^aR^{a1})_rNR^aC(O)OR^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, $-(CR^aR^{a1})_r-C_{3-10}$ carbocycle substituted with 0–2 $R^{c1}$, or $-(CR^aR^{a1})_r-$5–10 membered heterocycle consisting of carbon atoms and 1–4 heteroatoms selected from the group consisting of N, O, and $S(O)_p$ and substituted with 0–2 $R^{c1}$.

3. A compound according to claim 2, wherein:

L is $-(CR^2R^3)-$, $-(CR^2R^3)-CH_2-$, $-(CR^2R^3)-(CH_2)_2-$, $-CH_2-(CR^4R^5)-$, or $-CH_2-(CR^4R^5)-CH_2-$;

alternatively, L is selected from the group:

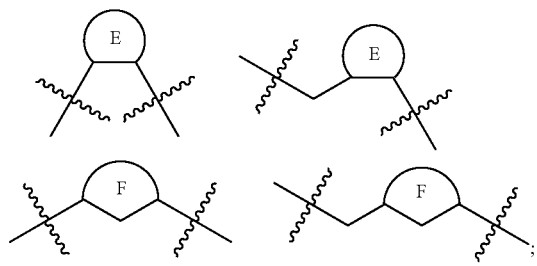

$R^2$ is $Q^1$, $C_{1-6}$ alkylene-$Q^1$, $C_{2-6}$ alkenylene-$Q^1$, $C_{2-6}$ alkynylene-$Q^1$, $-(CH_2)_rO(CH_2)_s-Q^1$, $-(CH_2)_rNR^a(CH_2)_s-Q^1$, $-(CH_2)_rC(O)(CH_2)_s-Q^1$, $-(CH_2)_rC(O)O(CH_2)_s-Q^1$, $-(CH_2)_rC(O)NR^a(CH_2)_s-Q^1$, $-(CH_2)_rNR^aC(O)(CH_2)_s-Q^1$, $-(CH_2)_rS(O)_p(CH_2)_s-Q^1$, $-(CH_2)_rSO_2NR^a(CH_2)_s-Q^1$, or $-(CH_2)_rN-R^aSO_2(CH_2)_s-Q^1$;

$R^3$ is Q, $C_{1-6}$ alkylene-Q, $C_{2-6}$ alkenylene-Q, $C_{2-6}$ alkynylene-Q, $-(CH_2)_rO(CH_2)_s-Q$, $-(CH_2)_rNR^a(CH_2)_s-Q$, $-(CH_2)_rC(O)(CH_2)_s-Q$, $-(CH_2)_rC(O)O(CH_2)_s-Q$, $-(CH_2)_rC(O)NR^aR^{a1}$, $-(CH_2)_rNR^aC(O)(CH_2)_s-Q$, $-(CH_2)_rS(O)_p(CH_2)_s-Q$, $-(CH_2)_rSO_2NR^a(CH_2)_s-Q$, or $-(CH_2)_rNR^aSO_2(CH_2)_s-Q$;

Q is, independently at each occurrence, H, a $C_{3-10}$ carbocycle substituted with 0–3 $R^d$, or a 5–10 membered heterocycle consisting of carbon atoms and 1–4 heteroatoms selected from the group consisting of N, O, and $S(O)_p$, and substituted with 0–3 $R^d$;

$R^4$ is H or $C_{1-6}$alkyl;

$R^5$ is H or $C_{1-6}$ alkyl;

alternatively, $R^2$ and $R^3$, together with the carbon atom to which they are attached, combine to form a 3–8 membered carbocyclic or heterocyclic ring consisting of carbon atoms, 0–2 ring heteroatoms selected from O, N, $NR^{10}$, and $S(O)_p$, and 0–2 double bonds, and substituted with 0–2 $R^9$;

alternatively, $R^4$ and $R^5$, together with the carbon atom to which they are attached, combine to form a 3–8 membered carbocyclic or heterocyclic ring consisting of carbon atoms, 0–2 ring heteroatoms selected from O, N, $NR^{10}$, and $S(O)_p$, and 0–2 double bonds, and substituted with 0–2 $R^9$;

ring E is a $C_{3-7}$ cycloalkyl substituted with 0–2 $R^c$, a $C_{4-7}$ cycloalkenyl substituted with 0–2 $R^c$, phenyl substituted with 0–3 $R^c$, or a 5–7 membered heterocyclic ring consisting of carbon atoms and 0–2 ring heteroatoms selected from O, N, $NR^{10}$, and $S(O)_p$, and 0–2 double bonds, and substituted with 0–3 $R^c$;

ring F is a $C_{4-7}$ cycloalkyl substituted with 0–2 $R^c$, a $C_{4-7}$ cycloalkenyl substituted with 0–2 $R^c$, phenyl substituted with 0–3 $R^c$, or a 5–7 membered heterocyclic ring consisting of carbon atoms and 0–2 ring heteroatoms selected from O, N, $NR^{10}$, and $S(O)_p$, and 0–2 double bonds, and substituted with 0–3 $R^c$;

U is O, C(O), $C(O)NR^{a1}$, $NR^{a1}C(O)$, $S(O)_p$, $S(O)_pNR^{a1}$, or $NR^{a1}S(O)_p$;

X is absent, or is methylene or ethylene;

Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

$U^a$ is absent or is O, $NR^{a1}$, C(O), $C(O)NR^{a1}$, $NR^{a1}C(O)$, $S(O)_p$, $S(O)_pNR^{a1}$, or $NR^{a1}S(O)_p$;

$R^{a3}$ is, independently at each occurrence, H, $C_{1-6}$ alkyl, $C_{2-6}$ alkenyl, or $-(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^c$ is, independently at each occurrence, H, $OR^a$, Cl, F, Br, =O, $CF_3$, $CH_2F$, $CHF_2$, $-(CR^aR^{a1})_rNR^aR^{a1}$, $-(CR^aR^{a1})_rC(O)R^{a1}$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, $C_{1-6}$ alkyl, $C_{2-6}$ alkenyl, $C_{2-6}$ alkynyl, $C_{3-6}$ cycloalkyl substituted with 0–2 $R^{c1}$, phenyl substituted with 0–2 $R^{c1}$, or a 5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a 5–7 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^d$ is, independently at each occurrence, $C_{1-6}$ alkyl, $OR^a$, Cl, F, Br, =O, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, $CF_3$ or phenyl;

$R^9$ is, independently at each occurrence, H, —$(CR^aR^{a1})_r$ $NR^aR^{a1}$, —$(CR^aR^{a1})_rC(O)(CR^aR^{a1})_sR^e$, —$(CR^aR^{a1})_r$ $C(O)OR^{a1}$, —$(CR^aR^{a1})_rC(O)NR^aR^{a1}$, —$(CR^aR^{a1})_r$ $NR^aC(O)R^{a1}$, —$(CR^aR^{a1})_rS(O)_pR^{a3}$, —$(CR^aR^{a1})_r$ $SO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^c$, —$(CR^aR^{a1})_r$—$C_{3-10}$ carbocycle substituted with 0–2 $R^{c1}$, or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

$R^{10}$ is, independently at each occurrence, H, —$(CR^aR^{a1})_t$ $NR^aR^{a1}$, —$(CR^aR^{a1})_rC(O)(CR^aR^{a1})_sR^e$, —$(CR^aR^{a1})_r$ $C(O)OR^{a1}$, —$(CR^aR^{a1})_rC(O)NR^aR^{a1}$, —$(CR^aR^{a1})_t$ $NR^aC(O)R^{a1}$, —$(CR^aR^{a1})_rS(O)_pR^{a3}$, —$(CR^aR^{a1})_r$ $SO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or —$CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

r, at each occurrence, is selected from 0, 1, 2, and 3;
s, at each occurrence, is selected from 0, 1, 2, and 3; and
t, at each occurrence, is selected from 1, 2, and 3.

4. A compound according to claim 3, wherein:

Q is, independently at each occurrence, H, a $C_{3-8}$ carbocycle substituted with 0–3 $R^d$, or a 5–10 membered heterocycle consisting of carbon atoms and 1–4 heteroatoms selected from the group consisting of N, O, and $S(O)_p$, and substituted with 0–3 $R^d$;

$Q^1$ is, independently at each occurrence, H, a $C_{3-10}$ carbocycle substituted with 0–5 $R^d$, or a 5–10 membered heterocycle consisting of carbon atoms and 1–4 heteroatoms selected from the group consisting of N, $NR^{10}$, O, and $S(O)_p$, and substituted with 0–3 $R^d$;

Z is phenyl substituted with 0–3 $R^b$, naphthyl substituted with 0–5 $R^b$, pyridyl substituted with 0–3 $R^b$, thienyl substituted with 0–2 $R^b$, thiazolyl substituted with 0–2 $R^b$, oxazolyl substituted with 0–2 $R^b$, isoxazolyl substituted with 0–2 $R^b$, or imidazolyl substituted with 0–2 $R^b$;

$Z^a$ is phenyl substituted with 0–3 $R^c$, naphthyl substituted with 0–3 $R^c$, or a heterocycle substituted with 0–3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydroisoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

$R^a$ is, independently at each occurrence, H, $C_{1-6}$ alkyl, phenyl, or benzyl;

$R^{a1}$ is, independently at each occurrence, H, $C_{1-6}$ alkyl, phenyl, or benzyl;

$R^{a3}$ is, independently at each occurrence, H, $C_{1-6}$ alkyl, phenyl, or benzyl;

$R^c$ is, independently at each occurrence, H, $OR^a$, Cl, F, Br, =O, $CF_3$, $CH_2F$, $CHF_2$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or a 5–6 membered heterocycle consisting of carbon atoms and 1–4 heteroatoms selected from the group consisting of N, O, and $S(O)_p$ and substituted with 0–2 $R^{c1}$;

alternatively, when two $R^c$ groups are attached to the same carbon atom, they form a 5–6 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^9$ is, independently at each occurrence, H, —$(CR^aR^{a1})_r$ $NR^aR^{a1}$, —$(CR^aR^{a1})_rC(O)(CR^aR^{a1})_sR^e$, —$(CR^aR^{a1})_r$ $C(O)OR^{a1}$, —$(CR^aR^{a1})_rC(O)NR^aR^{a1}$, —$(CR^aR^{a1})_r$ $NR^aC(O)R^{a1}$, —$(CR^aR^{a1})_rS(O)_pR^{a3}$, —$(CR^aR^{a1})_r$ $SO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, —$(CR^aR^{a1})_r$—$C_{3-7}$ carbocycle substituted with 0–2 $R^{c1}$, or —$(CR^aR^{a1})_r$-5–6 membered heterocycle consisting of carbon atoms and 1–4 heteroatoms selected from the group consisting of N, O, and $S(O)_p$, and substituted with 0–2 $R^{c1}$; and $R^{10}$ is, independently at each occurrence, H, —$(CR^aR^{a1})_t$ $NR^aR^{a1}$, —$(CR^aR^{a1})_rC(O)(CR^aR^{a1})_sR^e$, —$(CR^aR^{a1})_r$ $C(O)OR^{a1}$, —$(CR^aR^{a1})_rC(O)NR^aR^{a1}$, —$(CR^aR^{a1})_t$ $NR^aC(O)R^{a1}$, —$(CR^aR^{a1})_rS(O)_pR^{a3}$, —$(CR^aR^{a1})_r$ $SO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$.

5. A compound according to claim 4, wherein:

$R^2$ is $Q^1$, $C_{1-4}$ alkylene-$Q^1$, $C_{2-4}$ alkenylene-$Q^1$, $C_{2-4}$ alkynylene-$Q^1$, —$(CH_2)_rO(CH_2)_s$—$Q^1$, —$(CH_2)_rNR^a$ $(CH_2)_s$—$Q^1$, —$(CH_2)_rC(O)(CH_2)_s$—$Q^1$, —$(CH_2)_rC$ (O)O(CH$_2$)$_s$—Q$^1$, —(CH$_2$)$_r$C(O)NR$^a$(CH$_2$)$_s$—Q$^1$, —(CH$_2$)$_r$NR$^a$C(O)(CH$_2$)$_s$—Q$^1$, —(CH$_2$)$_r$S(O)$_p$(CH$_2$)$_s$—Q$^1$, —(CH$_2$)$_r$SO$_2$NR$^a$(CH$_2$)$_s$—Q$^1$, or —(CH$_2$)$_r$NR$^a$SO$_2$(CH$_2$)$_s$—Q$^1$;

R$^3$ is H, C$_{1-4}$ alkyl, C$_{2-4}$ alkenyl, or C$_{2-4}$ alkynyl;

R$^4$ is H or C$_{1-4}$ alkyl;

R$^5$ is H or C$_{1-4}$ alkyl;

alternatively, R$^2$ and R$^3$, together with the carbon atom to which they are attached, combine to form a 3–8 membered carbocyclic or heterocyclic ring consisting of carbon atoms, 0–2 ring heteroatoms selected from O, N, NR$^{10}$, and S(O)$_p$, and 0–2 double bonds;

alternatively, R$^4$ and R$^5$, together with the carbon atom to which they are attached, combine to form a 3–8 membered carbocyclic or heterocyclic ring consisting of carbon atoms, 0–2 ring heteroatoms selected from O, N, NR$^{10}$, and S(O)$_p$, and 0–2 double bonds;

Q$^1$ is, independently at each occurrence, H, a C$_{3-6}$ carbocycle substituted with 0–2 R$^d$, or a 5–6 membered heterocycle consisting of carbon atoms and 1–4 heteroatoms selected from the group consisting of N, NR$^{10}$, O, and S(O)$_p$, and substituted with 0–2 R$^d$;

ring E is a C$_{4-7}$ cycloalkyl substituted with 0–2 R$^c$, a C$_{4-7}$ cycloalkenyl substituted with 0–2 R$^c$, phenyl substituted with 0–2 R$^c$, or a heterocyclic ring substituted with 0–2 R$^c$ and selected from: furanyl, tetrahydrofuranyl, thienyl, thiazolyl, oxazolyl, imidazolyl, isothiazolyl, isoxazolyl, pyrazolyl, pyrrolyl, pyridyl, pyranyl, tetrahydropyranyl, pyrimidinyl,

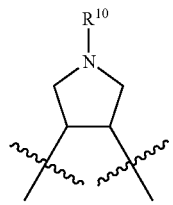 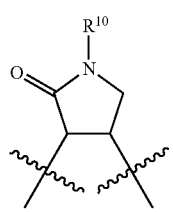

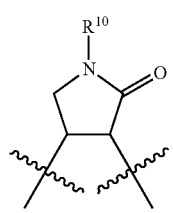 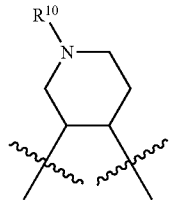

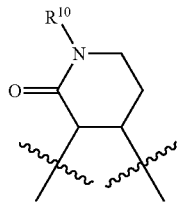 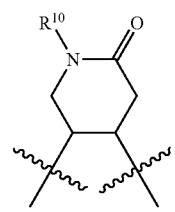

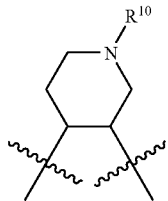 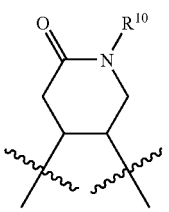

-continued

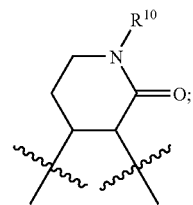

ring F a C$_{4-7}$ cycloalkyl substituted with 0–2 R$^c$, a C$_{4-7}$ cycloalkenyl substituted with 0–2 R$^c$, phenyl substituted with 0–2 R$^c$, or a heterocyclic ring substituted with 0–2 R$^c$ and selected from: pyridyl, pyranyl, tetrahydropyranyl, pyrimidinyl,

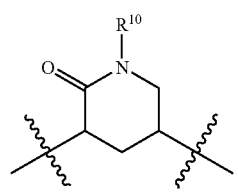

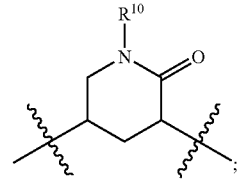

U is C(O), C(O)NR$^{a1}$, NR$^{a1}$C(O), S(O)$_p$, S(O)$_p$NR$^{a1}$, or NR$^{a1}$S(O)$_p$;

X is absent or is methylene;

Y is absent or is o;

Z is phenyl substituted with 0–3 R$^b$;

U$^a$ is absent or is o;

Y$^a$ is absent or is o;

R$^a$ is, independently at each occurrence, H, or C$_{1-4}$ alkyl;

R$^{a1}$ is, independently at each occurrence, H, or C$_{1-4}$ alkyl;

R$^{a3}$ is, independently at each occurrence, H, C$_{1-4}$ alkyl, phenyl, or benzyl;

R$^c$ is, independently at each occurrence, C$_{1-6}$ alkyl, C$_{2-6}$ alkenyl, C$_{2-6}$ alkynyl, OR$^a$, Cl, F, Br, =O, CF$_3$, CH$_2$F, CHF$_2$, NR$^aR^{a1}$, (CR$^aR^{a1}$)$_r$C(O)R$^{a1}$, (CR$^aR^{a1}$)$_r$C(O)OR$^{a1}$, (CR$^aR^{a1}$)$_r$C(O)NR$^aR^{a1}$, (CR$^aR^{a1}$)$_r$NR$^aC(O)R$^{a1}$, (CR$^aR^{a1}$)$_r$S(O)$_p$R$^{a3}$, (CR$^aR^{a1}$)$_r$SO$_2$NR$^aR^{a1}$, (CR$^aR^{a1}$)$_r$NR$^aSO_2$R$^{a3}$, or phenyl;

alternatively, when two R$^c$ groups are attached to the same carbon atom, they form a 5–6 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–6 membered carbocyclic or heterocyclic ring D substituted with 0–1 R$^{c1}$ and consisting of carbon atoms, 0–2 heteroatoms selected from the group consisting of N, O, and S(O)$_p$, and 0–3 double bonds;

R$^e$ is, independently at each occurrence, H, C$_{1-6}$ alkyl, C$_{1-6}$ alkoxy, phenoxy, benzoxy, C$_{3-6}$ carbocycle substituted with 0–2 R$^{c1}$, or a 5–6 membered heterocycle consisting of carbon atoms and 1–4 heteroatoms selected from the group consisting of N, O, and S(O)$_p$, and substituted with 0–2 R$^{c1}$; and R$^{10}$ is, independently at each occurrence, H, —(CH$_2$)$_t$NR$^a$R$^{a1}$, —(CH$_2$)$_r$C(O)(CH$_2$)$_s$R$^e$, (CH$_2$)$_r$C(O)OR$^{a1}$, —(CH$_2$)$_r$C(O)NR$^a$R$^{a1}$, —(CH$_2$)$_r$NR$^a$C(O)R$^{a1}$, —(CH$_2$)$_r$S(O)$_p$R$^{a3}$, —(CH$_2$)$_r$SO$_2$NR$^a$R$^{a1}$, —(CH$_2$)$_t$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CH$_2$)$_r$—C$_{3-10}$ carbocycle substituted with 0–2 R$^{c1}$, or —(CH$_2$)$_r$-5–10 membered heterocycle consisting of carbon atoms and 1–4 heteroatoms selected from the group consisting of N, O, and S(O)$_p$, and substituted with 0–2 R$^{c1}$.

6. A compound according to claim 5, wherein:

R$^2$ is H, C$_{1-4}$ alkyl, C$_{2-6}$ alkenyl, or C$_{2-6}$ alkynyl;

R$^3$ is H or C$_{1-4}$ alkylene;

R$^4$ is H or C$_{1-4}$ alkyl;

R$^5$ is H or C$_{1-4}$ alkyl;

alternatively, R$^2$ and R$^3$, together with the carbon atom to which they are attached, combine to form a C$_{3-7}$ cycloalkyl, a C$_{3-7}$ cycloalkenyl, or a 5–6 membered heterocyclic ring consisting of carbon atoms, 1 ring heteroatom selected from O, N, NR$^{10}$, and S(O)$_p$, and 0–2 double bonds;

alternatively, R$^4$ and R$^5$, together with the carbon atom to which they are attached, combine to form a C$_{3-7}$ cycloalkyl, a C$_{3-7}$ cycloalkenyl, or a 5–6 membered heterocyclic ring consisting of carbon atoms, 1 ring heteroatom selected from O, N, NR$^{10}$, and S(O)$_p$, and 0–2 double bonds;

W is (CH$_2$)$_m$;

Y is absent;

Z is phenyl substituted with 0–1 R$^b$;

Z$^a$ is phenyl substituted with 0–3 R$^c$, naphthyl substituted with 0–3 R$^c$, or a heterocycle substituted with 0–3 R$^c$ and selected from the group: pyridyl, quinolinyl, tetrahydroquinolinyl, isoquinolinyl, tetrahydro-isoquinolinyl, imidazolyl, pyridoimidazolyl, benzimidazolyl, indolyl, indolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

R$^b$ is, independently at each occurrence, C$_{1-6}$ alkyl, OR$^a$, Cl, F, Br, NR$^a$R$^{a1}$, C(O)R$^a$, C(O)OR$^a$, C(O)NR$^a$R$^{a1}$, S(O)$_2$NR$^a$R$^{a1}$, NR$^a$S(O)$_2$R$^{a3}$, S(O)$_p$R$^{a3}$, or CF$_3$;

R$^c$ is, independently at each occurrence, C$_{1-6}$ alkyl, C$_{2-6}$ alkenyl, C$_{2-6}$ alkynyl, OR$^a$, Cl, F, Br, =O, CF$_3$, —NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, or —(CR$^a$R$^{a1}$)$_r$NR$^a$SO$_2$R$^{a3}$;

alternatively, when two R$^c$ groups are attached to the same carbon atom, they form a 5–6 membered carbocyclic or heterocyclic spiro ring C consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–6 membered carbocyclic or heterocyclic ring D consisting of carbon atoms, 0–2 heteroatoms selected from the group consisting of N, O, and S(O)$_p$, and 0–3 double bonds;

R$^e$ is, independently at each occurrence, H, C$_{1-6}$ alkyl, C$_{1-6}$ alkoxy, phenoxy, benzoxy, phenyl substituted with 0–1 R$^{c1}$, or a 5–6 membered heterocycle consisting of carbon atoms and 1–4 heteroatoms selected from the group consisting of N, O, and S(O)$_p$, and substituted with 0–1 R$^{c1}$;

R$^{10}$ is, independently at each occurrence, H, —(CH$_2$)$_r$C(O)(CH$_2$)$_s$R$^e$, —(CH$_2$)$_r$C(O)OR$^{a1}$, —(CH$_2$)$_r$C(O)NR$^a$R$^{a1}$, —(CH$_2$)$_r$S(O)$_p$R$^{a3}$, —(CH$_2$)$_r$SO$_2$NR$^a$R$^{a1}$, C$_{1-4}$ alkyl substituted with 0–1 R$^{c1}$, C$_{2-4}$ alkenyl substituted with 0–1 R$^{c1}$, C$_{2-4}$ alkynyl substituted with 0–1 R$^{c1}$, —(CH$_2$)$_r$—C$_{3-6}$ cycloalkyl substituted with 0–2 R$^{c1}$, —(CH$_2$)$_r$-phenyl substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;

m, at each occurrence, is selected from 0, 1, and 2;

r, at each occurrence, is selected from 0, 1, and 2; and s, at each occurrence, is selected from 0, 1, and 2.

7. A compound according to claim 6, wherein:

L is selected from: —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—,

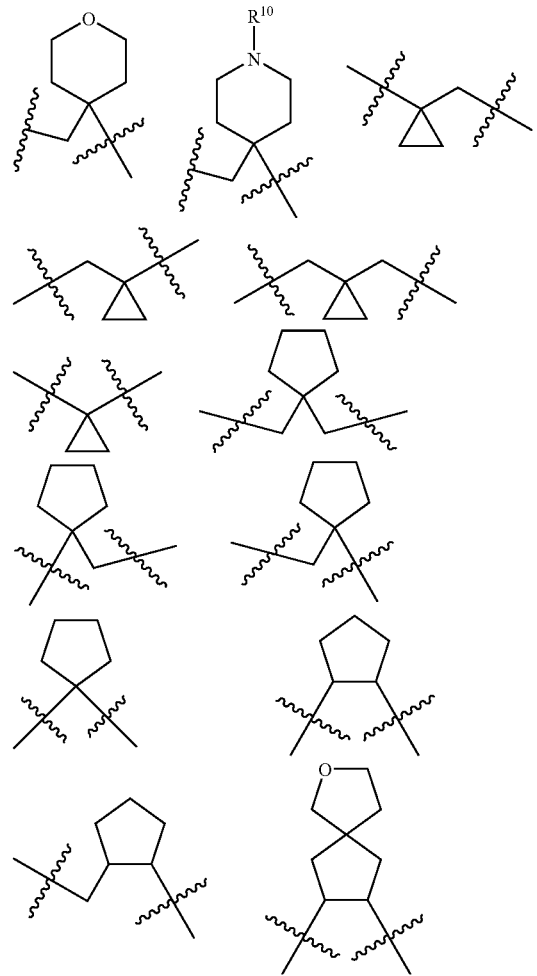

-continued

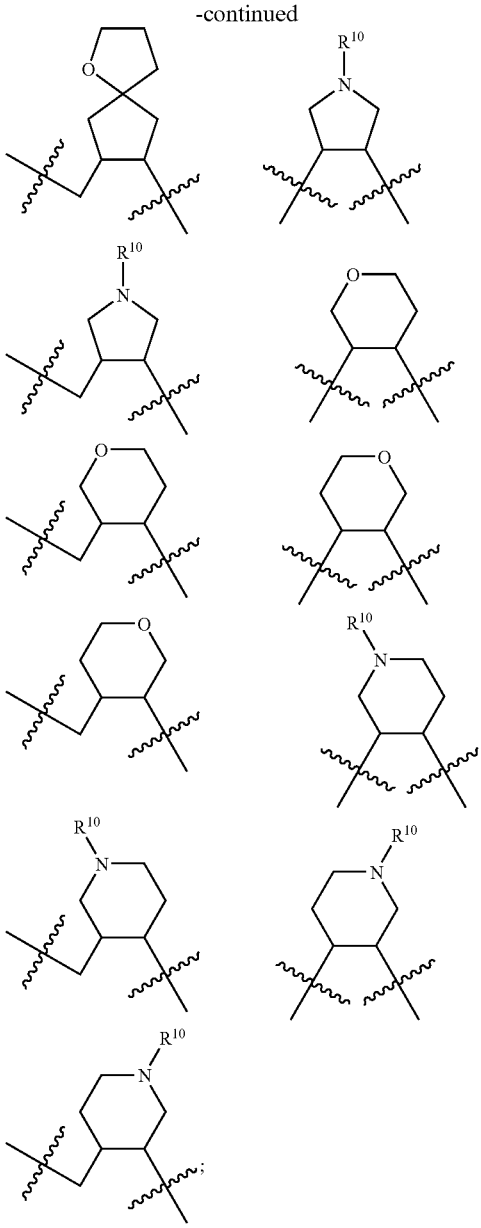

W is $(CH_2)_m$;
Y is absent;
Z is phenyl substituted with 0–1 $R^b$;
$Z^a$ is a heterocycle substituted with 0–3 $R^c$ and selected from the group: quinolinyl, isoquinolinyl, and 1,1-dioxido-2,3-dihydro-4H-1,4-benzothiazin-4-yl; and
$R^{10}$ is H, methyl, ethyl, isopropyl, isobutyl, 2-propynyl, acetyl, 2,2-dimethylpropanoyl, t-butoxycarbonyl, 3-methylbutanoyl, isobutyryl, isonicotinoyl, phenoxyacetyl, methanesulfonyl, 3-pyridinylmethyl, 4-pyridinylmethyl, 3-pyridinylcarbonyl, 4-piperidinylcarbonyl, 4-morpholinylacetyl, 4-morpholinomethyl, or [1-(t-butoxycarbonyl)-4-piperidinyl]carbonyl.

8. A compound according to claim 1, wherein the compound is selected from the group:
4-(2-methyl-quinolin-4-ylmethoxy)-N-[3-(5-thioxo-4,5-dihydro-1H-[1,2,4]triazol-3-yl)-propyl]-benzamide;
4-(2-methyl-quinolin-4-ylmethoxy)-N-[2-(5-thioxo-4,5-dihydro-1H-[1,2,4]triazol-3-yl)-ethyl]-benzamide;
4-(2-methyl-quinolin-4-ylmethoxy)-N-(5-thioxo-4,5-dihydro-1H-[1,2,4]triazol-3-ylmethyl)-benzamide;
N-[1,1-dimethyl-2-(5-thioxo-4,5-dihydro-1H-[1,2,4]triazol-3-yl)-ethyl]-4-(2-methyl-quinolin-4-ylmethoxy)-benzamide;
4-[4-(2-methyl-quinolin-4-ylmethoxy)-benzoylamino]-4-(5-thioxo-4,5-dihydro-1H-[1,2,4]triazol-3-ylmethyl)-piperidine-1-carboxylic acid tert-butyl ester;
4-(2-methyl-quinolin-4-ylmethoxy)-N-[4-(5-thioxo-4,5-dihydro-1H-[1,2,4]triazol-3-ylmethyl)-tetrahydro-pyran-4-yl]-benzamide;
4-(2-methyl-quinolin-4-ylmethoxy)-N-[1-(5-thioxo-4,5-dihydro-1H-[1,2,4]triazol-3-yl)-cyclopropylmethyl]-benzamide;
5-{1-[4-(2-methyl-quinolin-4-ylmethoxy)-benzenesulfonylmethyl]-cyclopentylmethyl}-2,4-dihydro-[1,2,4]triazole-3-thione;
4-[4-(2-isopropyl-benzoimidazol-1-ylmethyl)-benzoylamino]-4-(5-thioxo-4,5-dihydro-1H-[1,2,4]triazol-3-ylmethyl)-piperidine-1-carboxylic acid tert-butyl ester;
4-(2-methyl-quinolin-4-ylmethoxy)-N-[cis 2-(5-thioxo-4,5-dihydro-1H-[1,2,4]triazol-3-yl)-cyclopentyl]-benzamide;
4-(2-isopropyl-benzoimidazol-1-ylmethyl)-N-[2-(5-thioxo-4,5-dihydro-1H-[1,2,4]triazol-3-yl)-cyclopentyl]-benzamide;
4-(2-methyl-quinolin-4-ylmethyl)-N-[2-(5-thioxo-4,5-dihydro-1H-[1,2,4]triazol-3-yl)-cyclopentyl]-benzamide;
4-(2-methyl-quinolin-4-ylmethoxy)-N-[2-(5-thioxo-4,5-dihydro-1H-[1,2,4]triazol-3-yl)-cyclopentyl]-benzenesulfonamide;
(3S,4R)-4-(2-methyl-quinolin-4-ylmethoxy)-N-[3-(5-thioxo-4,5-dihydro-1H-[1,2,4]triazol-3-yl)-tetrahydro-pyran-4-yl]-benzamide;
trans-4-(2-methyl-quinolin-4-ylmethoxy)-N-[3-(5-thioxo-4,5-dihydro-1H-[1,2,4]triazol-3-yl)-tetrahydro-pyran-4-yl]-benzamide;
(5R,7R,8S)-4-(2-methyl-quinolin-4-ylmethoxy)-N-[8-(5-thioxo-4,5-dihydro-1H-[1,2,4]triazol-3-yl)-1-oxa-spiro[4.4]non-7-yl]-benzamide;
3-[4-(2-methyl-quinolin-4-ylmethoxy)-benzoylamino]-4-(5-thioxo-4,5-dihydro-1H-[1,2,4]triazol-3-yl)-pyrrolidine-1-carboxylic acid tert-butyl ester;
4-(2-methyl-quinolin-4-ylmethoxy)-N-[4-(5-thioxo-4,5-dihydro-1H-[1,2,4]triazol-3-yl)-pyrrolidin-3-yl]-benzamide;
3-[4-(1,1-dioxo-2,3-dihydro-1H-1$\lambda^6$-benzo[1,4]thiazin-4-ylmethyl)-benzoylamino]-4-(5-thioxo-4,5-dihydro-1H-[1,2,4]triazol-3-yl)-pyrrolidine-1-carboxylic acid tert-butyl ester;
4-(1,1-dioxo-2,3-dihydro-1H-1$\lambda^6$-benzo[1,4]thiazin-4-ylmethyl)-N-[4-(5-thioxo-4,5-dihydro-1H-[1,2,4]triazol-3-yl)-pyrrolidin-3-yl]-benzamide;
(3S,4S)-4-(2-methyl-quinolin-4-ylmethoxy)-N-[4-(5-thioxo-4,5-dihydro-1H-[1,2,4]triazol-3-yl)-pyrrolidin-3-yl]-benzamide;
(3S,4S)-N-[1-acetyl-4-(5-thioxo-4,5-dihydro-1H-[1,2,4]triazol-3-yl)-pyrrolidin-3-yl]-4-(2-methyl-quinolin-4-ylmethoxy)-benzamide;
(3S,4S)-4-(2-methyl-quinolin-4-ylmethoxy)-N-[1-propyl-4-(5-thioxo-4,5-dihydro-1H-[1,2,4]triazol-3-yl)-pyrrolidin-3-yl]-benzamide;
trans-4-(2-methyl-quinolin-4-ylmethoxy)-N-[4-(5-thioxo-4,5-dihydro-1H-[1,2,4]triazol-3-yl)-pyrrolidin-3-yl]-benzamide;
(3S,4S)-3-[4-(2-methyl-quinolin-4-ylmethoxy)-benzoylamino]-4-(5-thioxo-4,5-dihydro-1H-[1,2,4]triazol-3-yl)-piperidine-1-carboxylic acid tert-butyl ester;

(3S,4S)-4-(2-methyl-quinolin-4-ylmethoxy)-N-[4-(5-thioxo-4,5-dihydro-1H-[1,2,4]triazol-3-yl)-piperidin-3-yl]-benzamide;

(3S,4S)-N-[1-acetyl-4-(5-thioxo-4,5-dihydro-1H-[1,2,4]triazol-3-yl)-piperidin-3-yl]-4-(2-methyl-quinolin-4-ylmethoxy)-benzamide;

(3S,4S)-4-(2-methyl-quinolin-4-ylmethoxy)-N-[1-propyl-4-(5-thioxo-4,5-dihydro-1H-[1,2,4]triazol-3-yl)-piperidin-3-yl]-benzamide;

(3S,4S)-N-[1-methanesulfonyl-4-(5-thioxo-4,5-dihydro-1H-[1,2,4]triazol-3-yl)-piperidin-3-yl]-4-(2-methyl-quinolin-4-ylmethoxy)-benzamide;

(3S,4S)-N-[1-isopropyl-4-(5-thioxo-4,5-dihydro-1H-[1,2,4]triazol-3-yl)-piperidin-3-yl]-4-(2-methyl-quinolin-4-ylmethoxy)-benzamide;

(3S,4S)-4-(2-methyl-quinolin-4-ylmethoxy)-N-[1-methyl-4-(5-thioxo-4,5-dihydro-1H-[1,2,4]triazol-3-yl)-piperidin-3-yl]-benzamide;

(3S,4R)-4-(2-methyl-quinolin-4-ylmethoxy)-N-[3-(5-thioxo-4,5-dihydro-1H-[1,2,4]triazol-3-yl)-piperidin-4-yl]-benzamide;

4-(2-methyl-quinolin-4-ylmethoxy)-N-[2-(5-oxo-4,5-dihydro-1H-[1,2,4]triazol-3-yl)-cyclopentyl]-benzamide;

3-[4-(2-methyl-quinolin-4-ylmethoxy)-benzoylamino]-4-(5-oxo-4,5-dihydro-1H-[1,2,4]triazol-3-yl)-pyrrolidine-1-carboxylic acid tert-butyl ester; and 4-(2-methyl-quinolin-4-ylmethoxy)-N-[3-(5-oxo-4,5-dihydro-1H-[1,2,4]triazol-3-yl)-tetrahydro-pyran-4-yl]-benzamide;

or a pharmaceutically acceptable salt form thereof.

9. A pharmaceutical composition, comprising: a pharmaceutically acceptable carrier and a therapeutically effective amount of a compound according to claim 1 or a pharmaceutically acceptable salt form thereof.

10. A method for treating an inflammatory disorder, comprising: administering to a patient in need thereof a therapeutically effective amount of a compound according to claim 1 or a pharmaceutically acceptable salt form thereof.

11. A method of treating according to claim 10, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyagia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

12. A method for treating inflammatory disorders, comprising: administering, to a host in need of such treatment, a therapeutically effective amount of a compound of claim 1 or a pharmaceutically acceptable salt form thereof, in combination with one or more additional anti-inflammatory agents selected from selective COX-2 inhibitors, interleukin-1 antagonists, dihydroorotate synthase inhibitors, p38 MAP kinase inhibitors, TNF-α inhibitors and TNF-α antibody or protein sequestration agents.

13. An article of manufacture, comprising:
(a) a first container;
(b) a pharmaceutical composition located within the first container, wherein the composition, comprises: a first therapeutic agent, comprising: a compound of claim 1 or a pharmaceutically acceptable salt form thereof; and,
(c) a package insert stating that the pharmaceutical composition can be used for the treatment of an inflammatory disorder.

14. An article of manufacture according to claim 13, further comprising:
(d) a second container;
wherein components (a) and (b) are located within the second container and component (c) is located within or outside of the second container.

15. An article of manufacture, comprising:
(a) a first container;
(b) a pharmaceutical composition located within the first container, wherein the composition, comprises: a first therapeutic agent, comprising: a compound of claim 1, or a pharmaceutically acceptable salt form thereof; and,
(c) a package insert stating that the pharmaceutical composition can be used in combination with a second therapeutic agent to treat an inflammatory disorder.

16. An article of manufacture according to claim 13, further comprising:
(d) a second container;
wherein components (a) and (b) are located within the second container and component (c) is located within or outside of the second container.

17. A pharmaceutical composition, comprising: a pharmaceutically acceptable carrier and a therapeutically effective amount of a compound according to claim 2 or a pharmaceutically acceptable salt form thereof.

18. A pharmaceutical composition, comprising: a pharmaceutically acceptable carrier and a therapeutically effective amount of a compound according to claim 3 or a pharmaceutically acceptable salt form thereof.

19. A pharmaceutical composition, comprising: a pharmaceutically acceptable carrier and a therapeutically effective amount of a compound according to claim 4 or a pharmaceutically acceptable salt form thereof.

20. A pharmaceutical composition, comprising: a pharmaceutically acceptable carrier and a therapeutically effective amount of a compound according to claim 5 or a pharmaceutically acceptable salt form thereof.

21. A pharmaceutical composition, comprising: a pharmaceutically acceptable carrier and a therapeutically effective amount of a compound according to claim 6 or a pharmaceutically acceptable salt form thereof.

22. A pharmaceutical composition, comprising: a pharmaceutically acceptable carrier and a therapeutically effective amount of a compound according to claim 7 or a pharmaceutically acceptable salt form thereof.

23. A pharmaceutical composition, comprising: a pharmaceutically acceptable carrier and a therapeutically effective amount of a compound according to claim 8 or a pharmaceutically acceptable salt form thereof.

* * * * *